US007700544B2

(12) United States Patent
Kisilevsky et al.

(10) Patent No.: US 7,700,544 B2
(45) Date of Patent: Apr. 20, 2010

(54) COMPOSITIONS AND METHODS FOR TREATING ATHEROSCLEROSIS

(75) Inventors: Robert Kisilevsky, Kingston (CA); Shui-Pang Tam, Kingston (CA); John B. Ancsin, Kingston (CA); Zongchao Jia, Kingston (CA)

(73) Assignee: Queens's University at Kingston, Kingston, Ontario (CA)

( * ) Notice: Subject to any disclaimer, the term of this patent is extended or adjusted under 35 U.S.C. 154(b) by 428 days.

(21) Appl. No.: 11/268,690

(22) Filed: Nov. 7, 2005

(65) Prior Publication Data
US 2006/0111299 A1 May 25, 2006

Related U.S. Application Data

(63) Continuation-in-part of application No. 10/866,330, filed on Jun. 10, 2004, now Pat. No. 7,291,590.

(60) Provisional application No. 60/544,565, filed on Feb. 13, 2004, provisional application No. 60/478,131, filed on Jun. 12, 2003.

(51) Int. Cl.
*A61K 38/10* (2006.01)
*C07K 7/08* (2006.01)

(52) U.S. Cl. ............... 514/2; 514/12; 514/13; 530/300; 530/326

(58) Field of Classification Search .............. 530/300, 530/326; 514/2, 12, 13
See application file for complete search history.

(56) References Cited

U.S. PATENT DOCUMENTS

| 5,318,958 A | 6/1994 | Kisilevsky | ............. 514/21 |
| 6,004,936 A | 12/1999 | Kisilevsky | ............. 514/21 |

FOREIGN PATENT DOCUMENTS

| WO | WO 96/38166 | 12/1996 |
| WO | WO 01/21188 A1 | 3/2001 |
| WO | WO 2004/111084 A2 | 12/2004 |

OTHER PUBLICATIONS

Rudinger (1976) chracteristics of the amino acids as components of a peptide hormone, Peptide Hormones, University Park Press, Baltimore, MD., pp. 1-7.*
Bowie, et al. Deciphering the message in protein seqeunces: tolerance to amino acid substitutions (1990) Science, 247 : 1306-1310.*
Ancsin et al., "Basic residues in the Carboxy-Terminus of Mouse apoSAA are Involved in Heparin Binding", Proceedings of the VIIIth International Symposium on Amyloidosis, Rochester, Minnesota, USA Aug. 7-11, 1998 published in *Amyloid and Amyloidosis* 1998, Kyle, R.A. and Gertz, M.A., (eds.) Parthenon Publishing Group Limited, New York (1999), p. 17-19.
Ancsin et al., "Studies Defining the Serum Amyloid A:Heparin Binding Sites" FASEB Summer Conference, Copper Mountain Colorado, Jun. 11-16, 2000 (Abstract).

Ancsin et al., "The Heparin/Heparan Sulfate-binding Site on Apo-serum Amyloid A", J. Biol. Chem 1999 274:7172-7181.
Ancsin et al., "Laminin interactions with the apoproteins of acute-phase HDL:preliminary mapping of the laminin binding site on serum amyloid A", Amyloid: Int. J. Exp. Clin. Invest. 1999 6:37-47.
Bagshaw et al., "Characteristics of SAA-Phosphatidylcholine (PC) Liposome Binding to Mouse Macrophages", Canadian Federation of Biological Sciences, Montreal, Quebec, Jun. 1994 (Abstract).
Banka et al., "Serum amyloid A (SAA) :influence on HDL-mediated cellular cholesterol efflux", J. Lipid Res. 1995 36:1058-1065.
Bays et al., "Pharmacotherapy for dyslipidaemia -current therapies and future agents", Expert Opinion on Pharmacotherapy 2003 4(11):1901-1938.
Delsing et al., "Differential Effects of Amlodipine and Atorvastatin Treatment and Their Combination on Atherosclerosis in ApoE*3-Leiden Transgenic Mice", J. Cardiovasc. Pharmacol. 2003 42(1):63-70.
Ely et al., "The *in-vitro* influence of serum amyloid A isoforms on enzymes that regulate the balance between esterified and un-esterified cholesterol", Amyloid J. Protein Folding Disord. 2001 8:169-181.
Ely et al., "Influence of Serum Amyloid A (SAA) on Macrophage AcylCoA:Cholesterol Acyltransferase (ACAT) activity", VIIIth International Amyloid Symposium, Rochester, Minnesota, U.S.A., Aug. 7-11, 1998 published in *Amyloid and Amyloidosis 1998*, Kyle, R.A. and Gertz, M.A. (eds.) Parthenon Publishing Group Limited, New York (1999), p. 366-368.
Ganji et al., "Niacin and cholesterol:role in cardiovascular disease (Review)", J. Nutritional Biochemistry 2003 14:298-305.
Jousilahti et al., "The association of c-reactive protein, serum amyloid A and fibrinogen with prevalent coronary heart disease-baseline findings of the PAIS project", Atherosclerosis 2001 156:451-456.
Kajinami et al., "Cholesterol absorption inhibitors in development as potential therapeutics", Expert Opinion Investig. Drugs 2002 11(6):831-835.
Kinkley et al. "An EM autoradiography and Immunofluorescence Study Examining the Pathway of Serum Amyloid A Through the Macrophage", Xth International Amyloid Symposium, Tours, France, Apr. 18-22, 2004 (Abstract).
Kinkley et al. "An EM Autoradiography and Immunofluorescence Study Examining the Pathway of Serum Amyloid A Through the Macrophage", Xth International Amyloid Symposium, Tours, France, Apr. 18-22, 2004.
Kisilevsky et al. "Macrophage cholesterol efflux and the active domains of serum amyloid A 2.1", J. Lipid Res. 2003 44: 2257-2269.
Kisilevsky et al. "Serum Amyloid A (SAA) Changes HDL's Cellular Affinity: A Clue to SAA's Principal Function". 81st Annual Meeting U.S.-Canadian Academy of Pathology, Atlanta, Georgia, U.S.A. Mar. 1992, Abstract published in Lab. Invest. 1992 66:107A, (Abstract).

(Continued)

*Primary Examiner*—Chih-Min Kam
(74) *Attorney, Agent, or Firm*—Licata & Tyrrell P.C.

(57) ABSTRACT

Peptides and mimetics of selected domains of mammalian serum amyloid A isoform 2.1 (SAA2.1) and compounds and compositions thereof are provided that enhance the effect on macrophage cholesterol ester hydrolase activity and/or inhibit acyl CoA:cholesterol acyl transferase activity. Methods of using these compositions in the treatment and/or prevention of atherosclerosis as well as coronary heart disease and cardiovascular disease are also provided.

18 Claims, 23 Drawing Sheets

OTHER PUBLICATIONS

Kisilevsky et al. "Serum Amyloid A Influences the Efflux of Cholesterol from Macrophages", VIIth International Symposium on Amyloidosis, Kingston, Ontario, Canada, Jul. 1993.

Kisilevsky et al., "Influence of Serum Amyloid A (SAA) on Macrophage Acyl-CoA:Cholesterol Acyltransferase (ACAT) Activity". $52^{nd}$ Annual Meeting of the Canadian Cardiovascular Society, Quebec City, Quebec, Canada, Oct. 19-23, 1999 published in *Can. J. Cardiol. 1999* 15(Suppl D): 209D (Abstract).

Kisilevsky et al., "The Mechanism of Serum Amyloid A's (SAA) Stimulation of Neutral Cholesterol Ester Hydrolase (NCEH) Activity". $52^{nd}$ Annual Meeting of the Canadian Cardiovascular Society, Quebec City, Quebec, Canada, Oct. 19-23, 1999 published in *Can. J. Cardiol. 1999* 15(Suppl D): 180D (Abstract).

Kisilevsky et al., "Promoting Cholesterol Export from Macrophage Foam Cells—the Mechanism of Action of SAA2.1 and Its Implications". Canadian Cardiovascular Congress, Oct. 26-30, 2002, Edmonton, Alberta, Canada (Abstract).

Kisilevsky et al., "The promotion of macrophage cholesterol efflux by active domains of serum amyloid 2.1". Canadian Lipoprotein Conference, Muskoka, Ontario, Canada, Oct. 23-25, 2003 (Abstract).

Kisilevsky et al., "Acute Phase Serum Amyloid A, Cholesterol Metabolism, and Cardiovascular Disease", Pediatric Pathology and Molecular Medicine 2002 21:291-305.

Kisilevsky, R., "Serum Amyloid A (SAA), a Protein without a Function:Some Suggestions with Reference to Cholesterol Metabolism", Medical Hypotheses 1991 35:337-341.

Kisilevsky et al., "Acute phase serum amyloid A (SAA) and cholesterol transport during acute inflammation:A hypothesis", Amyloid: Int. J. Exp. Clin. Invest. 1996 3:252-260.

Kisilevsky et al., "Serum amyloid A changes high density lipoprotein's cellular affinity:A Clue to Serum Amyloid A's Principal Function", Laboratory Investigation 1992 66:778-785 with attached Erratum Kisilevsky et al., Laboratory Investigation 1992 67:151.

Knopp, R.H., "Evaluating Niacin in its Various Forms", Am. J. Cardiol. 2000 86(supp):51L-56L.

Kumon et al., "A Longitudinal Analysis of Alteration in Lecithin-Cholesterol Acyltransferase and Paraoxonase Activities Following Laparoscopic Cholecystectomy Relative to Other Parameters of HDL Function and the Acute Phase Response", Scand. J. Immunol. 1998 48:419-424.

Lee et al., "Minireview:Lipid Metabolism, Metabolic Diseases, and Peroxisome Proliferator-Activated Receptors", Endocrinology 2003 144:2201-2207.

Liang et al., "Serum Amyloid A Is a Chemotactic Agonist at FPR2, a Low-Affinity *N*-Formylpeptide Receptor on Mouse Neutrophils", Biochem. Biophys. Res. Commun 2000 270: 331-335.

Liang et al., "Recombinant human serum amyloid A ($apoSAA_p$) binds cholesterol and modulates cholesterol flux", J. Lipid Res. 1995 36:37-46.

Liang et al., "Amino terminal region of acute phase, but not constitutive, serum amyloid A (apoSAA) specifically binds and transports cholesterol into aortic smooth muscle and HepG2 cells", J. Lipid Res. 1996 37:2109-2116.

Lindhorst et al., "Acute inflammation, acute phase serum amyloid A and cholesterol metabolism in the mouse", Biochimica et Biophysica Acta 1997 1339:143-154.

Liuzzo et al., "The Prognostic Value of C-Reactive Protein and Serum Amyloid A Protein in Severe Unstable Angina", N. Engl. J. Med. 1994 331:417-424.

McCarthy et al., "Potent, Selective, and Systemically-Available Inhibitors of Acyl-Coenzyme A:Cholesterol Acyl Transferase (ACAT)", J. Med. Chem. 1994 37:1252-1255.

Ridker et al., "Inflammation, Pravastatin, and Risk of Coronary Events After Myocardial Infarction in Patients With Average Cholesterol Levels", Circulation 1998 98:839-844.

Robinson et al., "Use of Niacin in the Prevention and Management of Hyperlipidemia", Prog. Cardiovasc. Nurs. 2001 16(1):14-20.

Röcken et al., "Binding and endocytosis of $HDL_{SAA}$ by macrophages: implications for the pathogenesis of AA-amyloidosis?", German Society of Pathology, Dresden, Germany, Jun. 1996 (Abstract).

Röcken et al., "Binding and endocytosis of murine high density lipoprotein from healthy (HDL) and inflamed donors ($HDL_{SAA}$) by murine macrophages in vitro. A light and electronmicroscopic investigation", Amyloid:Int. J. Exp. Clin. Invest. 1997 4:259-273.

Röocken at al., Comparison of the binding and endocytosis of high-density lipoprotein from healthy (HDL) and inflamed ($HDL_{SAA}$) donors by murine macrophages of four different mouse strains. *Virchows Arch* 1998 432(6): 547-555.

Rosenthal et al., "Variation with Age and Disease of an Amyloid A Protein-Related Serum Component", J. Clin. Invest. 1975 55:746-753.

Shah et al., "Effects of Recombinant Apolipoprotein $A-I_{Milano}$ on Aortic Atherosclerosis in Apolipoprotein E-Deficient Mice", Circulation 1998 97:780-785.

Steinmetz et al., "Influence of serum amyloid A on cholesterol esterification in human plasma", Biochimica et Biophysica Acta 1989 1006:173-178.

Su et al., "A seven-transmembrane, G protein-coupled Receptor, FPRL1, Mediates the Chemotactic Activity of Serum Amyloid A for Human Phagocytic Cells". J. Exp. Med. 1999 189:395-402.

Tam et al., "Promoting export of macrophage cholesterol:the physiological role of a major acute-phase protein, serum amyloid A 2.1", J. Lipid Research 2002 43:1410-1420.

Tam et al., "Influence of Murine Serum Amyloid A 2.1, and its Active Domains, on Human Macrophage Cholesterol Export in Cell Culture", Xth International Amyloid Symposium, Tours, France, Apr. 18-22, 2004. (Abstract).

Tam et al. "Influence of Murine Serum Amyloid A 2.1, and its Active Domains, on Human Macrophage Cholesterol Export in Cell Culture", Xth International Amyloid Symposium, Tours, France, Apr. 18-22, 2004.

Tam et al. "Structural Aspects of the Active Domain of Murine and Human Serum Amyloid A 2.1 Responsible for its ACAT Inhibitory Properties", Xth International Amyloid Symposium, Tours, France, Apr. 18-22, 2004 (Abstract).

Tam et al., "The physiological role of serum amyloid A 2.1". IXth International Amyloid Symposium, Budapest, Hungary, Jul. 15-21, 2001, Abstract published in Amyloid J. Protein Folding Disord. 2001 8: Suppl 2:21-22 (Abstract).

Tam et al., "In Vivo Influence of Serum Amyloid A 2.1 and its Active Domains on Macrophage Cholesterol Export", Xth International Amyloid Symposium, Tours, France, Apr. 18-22, 2004 (Abstract).

Tam et al., "In Vivo Influence of Serum Amyloid A 2.1 and its Active Domains on Macrophage Cholesterol Export", Xth International Amyloid Symposium, Tours, France, Apr. 18-22, 2004.

Tontonoz et al., "Liver X Receptor Signaling Pathways in Cardiovascular Disease", Molecular Endocrinology 2003 17:985-993.

Van Lenten et al., "Anti-inflammatory HDL Becomes Pro-inflammatory during the Acute Phase Response", J. Clin. Invest. 1995 96:2758-2767.

Van et al., "Comparison of Extended-Release Niacin and Atorvastatin Monotherapies and Combination Treatment of the Atherogenic Lipid Profile in *Diabetes mellitus*", Am. J. Cardiol. 2002 89(11):1306-1308.

Young et al., "SAA Inhibits HDL-Cholesterol Uptake from LDL/VLDL: An Additional Clue to Its Principal Function". 84th Annual Meeting US-Canadian Academy of Pathology, Toronto, Ontario, Canada, Mar. 1995, Abstract published in Lab. Invest. 72: 37A, 1995 (Abstract).

UnitProt Accession No. Q9XSG7 Nov. 1, 1999.

Sela et al., "Different roles of D-amino acids in immune phenomena", FASEB J. 11:449-456 1997.

Tam et al., "Peptides derived from serum amyloid A prevent,and reverse,aortic lipid lesions in apoE$^{-/-}$mice", J. Lipid Res. 2005 46:2091-2101.

Liu et al., "Cyclodextrins differentially mobilize free and esterified cholesterol from primary human foam cell macrophages", Journal of Lipid Research 2003 44:1156-1166.

UnitProt Accession No. Q9XSG7 Nov. 1, 1999 Ohno et al.

* cited by examiner

Dose response curves of liposomes containing human SAA1.1 (residues 78-96) or mouse SAA2.1 (residues 74-103) on cholesterol efflux Dose response curves of liposomes containing human SAA1.1 (residues 78-96) or mouse SAA2.1 (residues 74-103) on cholesterol efflux Effects of equilmolar concentration of liposomes containing the entire length of mouse SAA2.1 or its peptide corresponding to residues 1-20 and 74-103 on cholesterol efflux in cholesterol-laden J774 cells D27mer on cholesterol efflux *in vivo*, dose response curve Effects of gavage vs intravenous injection of D-27mer on cholesterol efflux in CD1 mice The effects of glucose on cholesterol efflux *in vivo* after D-27 mer treatment by gavage Effects of liposomes containing various synthetic peptides on cholesterol efflux in cholesterol-loaded human THP-1 cells The effects of mSAA2.1, D-27mer, PPL5 and PPL4 on cholesterol efflux *in vivo*

The effects of fasting and without fasting on cholesterol efflux *in vivo* after D-27 mer treatment by gavage

COMPOSITIONS AND METHODS FOR TREATING ATHEROSCLEROSIS

This patent application is a continuation-in-part of U.S. application Ser. No. 10/866,330, filed Jun. 10, 2004, issued as U.S. Pat. No. 7,291,590, which claims the benefit of priority to U.S. Provisional patent application Ser. No. 60/544,565, filed Feb. 13, 2004 and U.S. Provisional patent application Ser. No. 60/478,131, filed Jun. 12, 2003, each of which is herein incorporated by reference in its entirety.

FIELD OF THE INVENTION

Peptides useful in inhibiting the storage of cholesterol and potentiating the mobilization and release of cholesterol from inflammatory or atherosclerotic sites in a subject have been identified. The present invention relates to isolated peptides, more preferably synthetic peptides including chemically and recombinantly synthesized peptides, compounds, and mimetics of these peptides and compounds, more preferably isolated peptides comprising a D amino acid, and pharmaceutical compositions comprising one or more of these peptides or a portion thereof, or compounds, or mimetics of these, and methods of using these peptides or mimetics thereof, compounds or mimetics thereof and pharmaceutical compositions in the treatment and/or prevention of atherosclerosis and inflammation, as well as coronary heart disease and cardiovascular disease.

BACKGROUND OF THE INVENTION

Cardiovascular disease, including coronary heart disease caused by atherosclerosis, is the single largest killer of adults in North America (2002 Heart and Stroke Statistical Update). The development and progression of atherosclerosis in coronary arteries can lead to heart attacks and angina. In 1999 it was estimated that 12.6 million Americans had coronary heart disease. Approximately 1 in 5 deaths in 1999 were due to coronary heart disease, with a total US and Canadian mortality of over 500,000 and 42,000 individuals, respectively. It is estimated that over 102 million American adults have blood cholesterol levels that are either border-line high risk, or high risk of developing coronary heart disease. In addition to the immediate social and economic burden that heart attacks have on our health care system, there also is the considerable cost associated with the aftermath of a coronary heart disease event. About 25% of males and 38% of females will die one year after a heart attack, and death by coronary heart disease tends to occur during a person's peak productive years (BRFSS [1997], MMWR vol. 49, No. SS-2, Mar. 24, 2000, CDC/NCHS). There is also a further economic burden of coronary heart disease associated with premature and permanent disability of the labor force. In 1998, over $10 billion was paid to Medicare beneficiaries for coronary heart disease (Health Care Financing Review, Statistical Supplement [2000], HFCA).

Patients currently have a choice of a number of different drugs to treat cardiovascular disease/coronary heart disease. These drugs fall into various classes, including antihypertensives and antihyperlipidemics. Although these products have been shown to be beneficial in reducing the progression of coronary heart disease and preventing heart attacks, they can be limited in their effectiveness in some individuals because of low tolerability and, in some cases, mitigation of drug efficacy by the compensatory effects of the liver (Turley, S. D. (2002) Am. J. Managed Care 8 (2 Suppl):S29-32).

The accumulation of lipids, especially cholesterol, in several aortic and arterial cell-types, such as macrophages and smooth muscle cells, is the defining pathologic feature of atherosclerosis (Gotlieb et al. (1999) Blood Vessels. In Pathology. Rubin, E. and Farber, J. L., editors. Lippincott-Raven, Philadelphia, New York. 481-530). Major investigative efforts are being expended to understand two central issues related to this problem. The first relates to the mechanism by which cholesterol is delivered to, and taken up by, these cells. The second relates to the process by which these cells export and rid themselves of excessive cholesterol. In the treatment and prevention of atherosclerosis, one of the aims is to limit the intracellular accumulation of large quantities of cholesterol that adversely influence the viability of these cells, thereby eventually altering the structural integrity of the blood vessels.

An analogous set of events occurs in acute tissue injury. Such injuries result in local cell death and set in motion local inflammation and the systemic acute phase response (Fantone, J. C. and Ward, P. A. (1994) Inflammation. In Pathology. Rubin, E. and Farber, J. editors. Lippincott, Philadelphia. 32-6). Alterations in local cholesterol processing are important components of this process. At sites of acute tissue injury, dying cells release large quantities of cell debris that includes cell membrane fragments rich in cholesterol (Fantone, J. C. and Ward, P. A. (1994) *Inflammation. In Pathology*. Rubin, E. and Farber, J. editors. Lippincott, Philadephia. 32-6). As part of acute inflammation, macrophages arriving at sites of injury ingest these fragments for further processing and thereby acquire a considerable cholesterol load, becoming foam cells, analogous to those seen in atherosclerosis. During acute tissue injury and the consequent acute inflammatory process, a cholesterol removal mechanism is required to mobilize the cholesterol either for excretion or re-use.

The physiological role of one of the major acute phase (AP) proteins synthesized by the liver in response to tissue injury, serum amyloid A (SAA), is directly related to these events and processes. SAA represents a group of four polymorphic proteins, encoded by a multigene family, that have been conserved for over 600 million years (Jensen et al. (1997) *J. Immunol.* 158:384-392; Santiago et al. (2000) *J. Exp. Zool.* 288: 3335-344). Isoforms SAA1.1 and SAA2.1 are present in plasma in acute phase tissue injury and are the most thoroughly investigated.

The nomenclature for serum amyloid A was revised in 1999, as there was a recognized need by researchers for a systematic nomenclature of the multiple SAA genes in human and animal models and for their allelic variants (Amyloid: Int. J. Exp. Clin. Invest. 1999 6:67-70). The major revision was the re-designation of the mouse Saa1 and Saa2 genes. Based upon chromosomal mapping, it appears that the mouse Saa2 locus corresponds to human SAA1. Therefore, the mouse nomenclature was changed to be fully compatible with the human nomenclature.

The following Tables set forth the revised nomenclature for SAA mouse and human proteins as well as their corresponding sequences. These tables are based upon the disclosure in 1999 in Amyloid: Int. J. Exp. Clin. Invest. 6:67-70. The tables presented herein have been modified, however, to clarify alignment and provide numbering for residue (−1) of mouse isoform SAA3 comprising an additional amino acid.

TABLE I

Mouse SAA Proteins

| New | Old | Seq ID # | -1 | 1 | 2 | 3 | 4 | 5 | 6 | 7 | 8 | 9 | 10 | 11 | 12 | 13 | 14 |
|---|---|---|---|---|---|---|---|---|---|---|---|---|---|---|---|---|---|
| SAA1.1 | SAA2 | 18 |  | G | F | F | S | F | I | G | E | A | F | Q | G | A | G |
| SAA1.2 | SJL/J | 33 |  |  |  |  |  |  |  |  |  |  |  |  |  |  |  |
| SAA1.3 | mc1 | 34 |  |  |  |  |  |  |  | S |  |  |  |  |  |  |  |
| SAA1.4 | mc2 | 35 |  |  |  |  |  |  |  | S |  |  |  |  |  |  |  |
| SAA1.5 | mm1 | 36 |  |  |  |  |  |  | V | H |  |  |  |  |  |  |  |
| SAA1.6 | mm2 | 37 |  |  |  |  |  |  |  |  |  |  |  |  |  |  |  |
| SAA2.1 | SAA1 | 19 |  |  |  |  |  |  | V | H |  |  |  |  |  |  |  |
| SAA2.2 | CE/J | 38 |  |  |  |  |  |  | V | H |  |  |  |  | L |  |  |
| SAA3 |  | 39 | Q | R | W | V | Q |  | M | K |  |  | G |  |  | S | R |
| SAA4 | SAA5 | 40 |  | D |  | W | Y |  | F | R |  |  |  |  |  | T | W |

|  |  | 15 | 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|---|---|---|
| SAA1.1 | SAA2 | D | M | W | R | A | Y | T | D | M | K | E | A | G | W | K | D |
| SAA1.2 | SJL/J |  |  |  |  |  |  |  |  |  |  |  |  |  |  |  |  |
| SAA1.3 | mc1 |  |  |  |  |  |  |  |  | R |  |  |  |  |  |  |  |
| SAA1.4 | mc2 |  |  |  |  |  |  |  |  |  |  |  |  |  |  |  |  |
| SAA1.5 | mm1 |  |  |  |  |  |  |  |  |  |  |  |  |  |  |  |  |
| SAA1.6 | mm2 |  |  |  |  |  |  |  |  |  |  |  |  |  |  |  |  |
| SAA2.1 | SAA1 |  |  |  |  |  |  |  |  |  |  |  |  |  | N |  | N |
| SAA2.2 | CE/J |  |  |  |  |  |  |  |  |  |  |  |  |  |  |  |  |
| SAA3 |  |  |  |  |  |  |  | S |  |  |  | K |  |  |  |  |  |
| SAA4 | SAA5 |  | L |  |  |  |  | R |  | N |  | L |  |  | N | Y | Q | N |

|  |  | 31 | 32 | 33 | 34 | 35 | 36 | 37 | 38 | 39 | 40 | 41 | 42 | 43 | 44 | 45 | 46 |
|---|---|---|---|---|---|---|---|---|---|---|---|---|---|---|---|---|---|
| SAA1.1 | SAA2 | G | D | K | Y | F | H | A | R | G | N | Y | D | A | A | Q | R |
| SAA1.2 | SJL/J |  |  |  |  |  |  |  |  |  |  |  |  |  |  |  |  |
| SAA1.3 | mc1 |  | R |  |  |  |  |  |  |  |  |  |  |  |  |  |  |
| SAA1.4 | mc2 |  |  |  |  |  |  |  |  |  |  |  |  |  |  |  |  |
| SAA1.5 | mm1 |  |  |  |  |  |  |  |  |  |  |  |  |  |  |  |  |
| SAA1.6 | mm2 |  |  |  |  |  |  |  |  |  |  |  |  |  |  |  |  |
| SAA2.1 | SAA1 | S |  |  |  |  |  |  |  |  |  |  |  |  |  |  |  |
| SAA2.2 | CE/J |  |  |  |  |  |  |  |  |  |  |  |  |  |  |  |  |
| SAA3 |  | S |  |  |  |  |  |  |  |  |  |  |  |  |  | R |  |
| SAA4 | SAA5 | A |  | Q |  |  | Y |  |  |  |  |  | E |  | Q |  |  |

|  |  | 47 | 48 | 49 | 50 | 51 | 52 | 53 | 54 | 55 | 56 | 57 | 58 | 59 | 60 | 61 | 62 |
|---|---|---|---|---|---|---|---|---|---|---|---|---|---|---|---|---|---|
| SAA1.1 | SAA2 | G | P | G | G | V | W | A | A | E | K | I | S | D | A | R | E |
| SAA1.2 | SJL/J |  |  |  |  |  |  |  |  |  |  |  |  |  |  |  |  |
| SAA1.3 | mc1 |  |  |  |  |  |  |  |  |  |  |  |  |  |  |  |  |
| SAA1.4 | mc2 |  |  |  |  |  |  |  |  |  |  |  |  |  |  |  |  |
| SAA1.5 | mm1 |  |  |  |  |  |  |  |  |  |  |  |  |  |  |  |  |
| SAA1.6 | mm2 |  |  |  |  |  |  |  |  |  |  |  |  |  |  |  |  |
| SAA2.1 | SAA1 |  |  |  |  |  |  |  |  |  |  |  |  |  | G |  |  |
| SAA2.2 | CE/J |  |  |  |  |  |  |  |  |  |  |  |  |  |  |  |  |
| SAA3 |  |  |  |  |  | A |  |  |  | K | V |  |  |  |  |  |  |
| SAA4 | SAA5 |  | S |  |  | I |  |  |  | K | I |  |  |  | T | S |  | K |

|  |  | 63 | 64 | 65 | 66 | 67 | 68 | 69 | 70 | 71 | 72 | 73 | 74 | 75 | 76 | 77 | 78 |
|---|---|---|---|---|---|---|---|---|---|---|---|---|---|---|---|---|---|
| SAA1.1 | SAA2 | S | F | Q | E | F | F | G | R | G | H | E | D | T | M | A | D |
| SAA1.2 | SJL/J |  |  |  |  |  |  |  |  |  |  |  |  |  |  |  |  |
| SAA1.3 | mc1 |  |  |  |  |  |  |  |  |  |  |  |  |  |  |  |  |
| SAA1.4 | mc2 | G |  |  |  |  |  |  |  |  |  |  |  |  |  |  |  |
| SAA1.5 | mm1 |  |  |  |  |  |  |  |  |  |  |  |  |  |  |  |  |
| SAA1.6 | mm2 |  |  |  |  |  |  |  |  |  |  |  |  |  |  |  |  |
| SAA2.1 | SAA1 | A |  |  |  |  |  |  |  |  |  |  |  |  | I |  |  |
| SAA2.2 | CE/J | A |  |  |  |  |  |  |  |  |  |  |  |  |  |  |  |
| SAA3 |  |  | V |  | K |  | T |  | H |  | A |  |  | S | R |  |  |
| SAA4 | SAA5 | Y |  |  | G | L | L | N | H |  | L |  | T | L | Q |  | T |

↑ [NRYYFGIR]

|  |  | 79 | 80 | 81 | 82 | 83 | 84 | 85 | 86 | 87 | 88 | 89 | 90 | 91 | 92 | 93 | 94 |
|---|---|---|---|---|---|---|---|---|---|---|---|---|---|---|---|---|---|
| SAA1.1 | SAA2 | Q | E | A | N | R | H | G | R | S | G | K | D | P | N | Y | Y |
| SAA1.2 | SJL/J |  |  |  |  |  |  |  |  |  |  |  |  |  |  |  |  |
| SAA1.3 | mc1 |  |  |  |  |  |  |  |  |  |  |  |  |  |  |  |  |
| SAA1.4 | mc2 |  |  |  |  |  |  |  |  |  |  |  |  |  |  |  |  |
| SAA1.5 | mm1 |  |  |  |  |  |  |  |  |  |  |  |  |  |  |  |  |
| SAA1.6 | mm2 |  |  |  |  |  |  |  |  |  |  |  |  |  |  |  |  |
| SAA2.1 | SAA1 |  |  |  |  |  |  |  |  |  |  |  |  |  |  |  |  |
| SAA2.2 | CE/J |  |  |  |  |  |  |  |  |  |  |  |  |  |  |  |  |

TABLE I-continued

Mouse SAA Proteins

| | | | | | | | | | | | | | |
|---|---|---|---|---|---|---|---|---|---|---|---|---|---|
| SAA3 | | | F | | E | W | | | | | | H | F |
| SAA4 | SAA5 | | K | | E | E | W | | | | N | H | F |

| | | 95 | 96 | 97 | 98 | 99 | 100 | 101 | 102 | 103 |
|---|---|---|---|---|---|---|---|---|---|---|
| SAA1.1 | SAA2 | R | P | P | G | L | P | A | K | Y |
| SAA1.2 | SJL/J | | | | | | | D | | |
| SAA1.3 | mc1 | | | | | | | | | |
| SAA1.4 | mc2 | | | | | | | | | |
| SAA1.5 | mm1 | | | | | | | | | |
| SAA1.6 | mm2 | | | | | | | D | | |
| SAA2.1 | SAA1 | | | | | | | D | | |
| SAA2.2 | CE/J | | | | | | | D | | |
| SAA3 | | | | A | | | | K | R | |
| SAA4 | SAA5 | | | E | | | | E | | F |

TABLE II

Human SAA proteins

| New | Old | Seq ID# | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|---|
| SAA1.1 | SAA1α | 20 | R | S | F | F | S | F | L | G | E | A | F | D | G | A | R |
| SAA1.2 | SAA1β | 41 | | | | | | | | | | | | | | | |
| SAA1.3 | SAA1γ | 42 | | | | | | | | | | | | | | | |
| SAA1.4 | SAA1δ | 43 | | | | | | | | | | | | | | | |
| SAA1.5 | SAA1β | 44 | | | | | | | | | | | | | | | |
| SAA2.1 | SAA2α | 21 | | | | | | | | | | | | | | | |
| SAA2.2 | SAA2β | 45 | | | | | | | | | | | | | | | |
| SAA4 | | 46 | E | S | W | R | S | F | F | K | E | A | L | Q | G | V | G |

| | | 16 | 17 | 18 | 19 | 20 | 21 | 22 | 23 | 24 | 25 | 26 | 27 | 28 | 29 | 30 | 31 |
|---|---|---|---|---|---|---|---|---|---|---|---|---|---|---|---|---|---|
| SAA1.1 | SAA1α | D | M | W | R | A | Y | S | D | M | R | E | A | N | Y | I | G |
| SAA1.2 | SAA1β | | | | | | | | | | | | | | | | |
| SAA1.3 | SAA1γ | | | | | | | | | | | | | | | | |
| SAA1.4 | SAA1δ | | | | | | | | | | | | | | | | |
| SAA1.5 | SAA1β | | | | | | | | | | | | | | | | |
| SAA2.1 | SAA2α | | | | | | | | | | | | | | | | |
| SAA2.2 | SAA2β | | | | | | | | | | | | | | | | |
| SAA4 | | D | M | G | R | A | Y | M | D | I | M | I | S | M | H | Q | N |

| | | 32 | 33 | 34 | 35 | 36 | 37 | 38 | 39 | 40 | 41 | 42 | 43 | 44 | 45 | 46 | 47 |
|---|---|---|---|---|---|---|---|---|---|---|---|---|---|---|---|---|---|
| SAA1.1 | SAA1α | S | D | K | Y | F | H | A | R | G | N | Y | D | A | A | K | R |
| SAA1.2 | SAA1β | | | | | | | | | | | | | | | | |
| SAA1.3 | SAA1γ | | | | | | | | | | | | | | | | |
| SAA1.4 | SAA1δ | | | | | | | | | | | | | | | | |
| SAA1.5 | SAA1β | | | | | | | | | | | | | | | | |
| SAA2.1 | SAA2α | | | | | | | | | | | | | | | | |
| SAA2.2 | SAA2β | | | | | | | | | | | | | | | | |
| SAA4 | | S | N | R | Y | L | Y | A | R | G | N | Y | D | A | A | Q | R |

| | | 48 | 49 | 50 | 51 | 52 | 53 | 54 | 55 | 56 | 57 | 58 | 59 | 60 | 61 | 62 | 63 |
|---|---|---|---|---|---|---|---|---|---|---|---|---|---|---|---|---|---|
| SAA1.1 | SAA1α | G | P | G | G | V | W | A | A | E | A | I | S | D | A | R | E |
| SAA1.2 | SAA1β | | | | | A | | | | | V | | | | | | |
| SAA1.3 | SAA1γ | | | | | A | | | | | | | | | | | |
| SAA1.4 | SAA1δ | | | | | A | | | | | V | | | N | | | |
| SAA1.5 | SAA1β | | | | | A | | | | | V | | | | | | |
| SAA2.1 | SAA2α | | | | | A | | | | | | | | N | | | |
| SAA2.2 | SAA2β | | | | | A | | | | | V | | | N | | | |
| SAA4 | | G | P | G | G | V | W | A | A | K | L | I | S | R | S | R | V |

| | | 64 | 65 | 66 | 67 | 68 | 69 | 70 | 71 | 72 | 73 | 74 | 75 | 76 | 77 | 78 | 79 |
|---|---|---|---|---|---|---|---|---|---|---|---|---|---|---|---|---|---|
| SAA1.1 | SAA1α | N | I | Q | R | F | F | G | H | G | A | E | D | S | L | A | D |
| SAA1.2 | SAA1β | | | | | | | | | D | | | | | | | |
| SAA1.3 | SAA1γ | | | | | | | | | | | | | | | | |
| SAA1.4 | SAA1δ | | | | | | | | | | | | | | | | |
| SAA1.5 | SAA1β | | | | | | | | | | | | | | | | |
| SAA2.1 | SAA2α | | | | | L | | T | | | | | | | | | |
| SAA2.2 | SAA2β | | | | | L | | T | | R | | | | | | | |

TABLE II-continued

Human SAA proteins

| | | 80 | 81 | 82 | 83 | 84 | 85 | 86 | 87 | 88 | 89 | 90 | 91 | 92 | 93 | 94 | 95 |
|---|---|---|---|---|---|---|---|---|---|---|---|---|---|---|---|---|---|
| SAA4 | | Y | L | Q | G↑<br>[DYYLFGNS] | L | I | S | T | V | L | E | D | S | K | S | N |
| SAA1.1 | SAA1α | Q | A | A | N | E | W | G | R | S | G | K | D | P | N | H | F |
| SAA1.2 | SAA1β | | | | | | | | | | | | | | | | |
| SAA1.3 | SAA1γ | | | | | | | | | | | | | | | | |
| SAA1.4 | SAA1δ | | | | | | | | | | | | | | | | |
| SAA1.5 | SAA1β | | | | | | | | | | | | | | | | |
| SAA2.1 | SAA2α | | | | | K | | | | | | R | | | | | |
| SAA2.2 | SAA2β | | | | | K | | | | | | R | | | | | |
| SAA4 | | E | K | A | E | E | W | G | R | S | G | K | D | P | D | R | F |

| | | 96 | 97 | 98 | 99 | 100 | 101 | 102 | 103 | 104 |
|---|---|---|---|---|---|---|---|---|---|---|
| SAA1.1 | SAA1α | R | P | A | G | L | P | E | K | Y |
| SAA1.2 | SAA1β | | | | | | | | | |
| SAA1.3 | SAA1γ | | | | | | | | | |
| SAA1.4 | SAA1δ | | | | | | | | | |
| SAA1.5 | SAA1β | | | | | | | | | |
| SAA2.1 | SAA2α | | | | | | | | | |
| SAA2.2 | SAA2β | | | | | | | | | |
| SAA4 | | R | P | D | G | L | P | K | K | Y |

The nomenclature for SAA proteins employed in this patent application corresponds to the revised nomenclature as set forth in the above Tables. However, it must be appreciated that journal references published prior to this 1999 revision and patent applications filed prior to this 1999 revision may use the old nomenclature, thus, for example referring to mouse Saa1 as mouse Saa2 and vice versa.

SAA isoforms SAA1.1 and SAA2.1 are produced primarily by hepatocytes in response to various causes of tissue injury and inflammation (Morrow et al. (1981) *Proc. Natl. Acad. Sci. USA* 78:4718-4722). Synthesis of SAA1.1 and 2.1 by the liver is induced by cytokines such as interleukin-1, interleukin-6, and tumor necrosis factor, which are released by activated macrophages, and which act through a set of downstream effectors in the hepatocyte cytoplasm and nucleus (Edbrooke et al. (1991) *Cytokine* 3:380-388; Betts et al. (1993) *J. Biol. Chem.* 268:25624-25631; Ray et al. (1999) *J. Biol. Chem.* 274:4300-430810; and Sipe et al. (1987) *Lymphokine Res.* 6:93-101). Maximum transcription rates for the SAA1.1 and 2.1 genes are seen 3-4 hours following tissue injury, and within 18-24 hours of injury the plasma concentration of these two proteins rises from 1-5 μg/mL to 500-1000 μg/mL (500-1000-fold increase) (McAdam et al. (1978) *J. Clin. Invest.* 61:390-394; McAdam, K. P., Sipe, J. D. (1976) *J. Exp. Med.* 144:1121-1127). Once secreted from hepatocytes, SAA1.1 and 2.1 are found predominantly in the high density lipoprotein (HDL) fraction and form 30-80% of the HDL apolipoproteins, resulting in a major reorganization of the apolipoprotein composition of the HDL fraction (Benditt et al. (1979) *Proc. Natl. Acad. Sci. USA* 76: 4092-4096; Hoffman, J. S. and Benditt, E. P. (1982) *J. Biol. Chem.* 257: 10518-10522).

At present there is debate whether the observed increase in SAA expression during tissue injury is associated with a beneficial role against atherosclerotic lesions, or whether increased SAA levels are in fact associated with a role in developing atherosclerosis.

Elevated levels of SAA isoforms are observed during the early pathological vascular events leading to atherosclerosis before clinical symptoms are evident. (reviewed in Kisilevsky, R. and Tam, S.-P. (2002) *Pediatric Pathol. and Mol. Med.* 21: 291-303). This elevation has led some researchers to suggest that SAA levels may play a causative, contributing role in atherogenesis (Jousilahti et al. (2001) *Atherosclerosis* 156:451-456; Kumon et al. (1998) *Scand. J. Immunol.* 48:419-424; Liuzzo et al. (1994) *N. Engl. J Med.* 331:417-424; Ridker et al. (1998) *Circulation* 98:839-844; Rosenthal, C. J. and Franklin, E. C. (1975) *J. Clin, Invest.* 55:746-753; Steinmetz et al. (1989) *Biochim Biophys. Acta.* 1006:173-178; Van Lenten et al. (1995) *J. Clin. Invest.* 96:2758-2767).

However, there have also been reports of SAA and isoforms thereof promoting the efflux of cholesterol from macrophages.

For example, high density lipoprotein-serum amyloid A (HDL-SAA) has been shown to have reduced ability to accept cholesterol from low density lipoprotein/very low density lipoprotein (LDL/VLDL), ensuring that HDL, in its afferent route, arrives at macrophages carrying as little cholesterol as possible (Kisilevsky et al. (1996) *Amyloid* 3: 252-260). Thus, this form of HDL has a greater capacity to accept cholesterol from cholesterol-laden macrophages. HDL-SAA has also been demonstrated to have a 3 to 4-fold higher affinity for macrophages when compared to HDL alone. Further, an increase was observed in the number of HDL-SAA binding sites on macrophages obtained from animals with an AP inflammatory reaction. Competition studies with macrophages (Kisilevsky, R. and Subrahmanyan, L. (1992) *Lab. Invest.* 66: 778-785) showed that unlabelled HDL-SAA, but not HDL alone, effectively displaced radiolabeled HDL-SAA. This preferential displacement by HDL-SAA is likely indicative of the presence of SAA receptors on the macrophages. Such SAA receptors are separate and additional to the binding sites for apoA-1 on the macrophages (Kisilevsky, R. and Subrahmanyan, L. (1992) *Lab. Invest.* 66: 778-785; U.S. Pat. No. 6,004,936). The presence of SAA receptors is further supported by the demonstration that HDL-SAA was in clathrin coated pits shortly after binding to macrophages. These pits and the resulting endosomes are consistent with the concept of receptor-mediated endocytosis, a process that is dependent on cell surface heparin sulphate, to which SAA binds effectively (Ancsin, J. and Kisilevsky, R. (1999) *J. Biol. Chem.* 274:7172-7181; Rocken, C. and Kisilevsky, R. (1997) *Amyloid* 4: 259-273).

More recent studies have demonstrated that SAA enhances HDL uptake by macrophages (Banka et al. (1995) *J. Lipid Res.* 36:1058-10865) and has an affinity for cholesterol (Liang, J. S. and Sipe, J. D. (1995) *J. Lipid Res.* 36:37-46). Using synthetic peptides corresponding to residues 1-18 and 40-63 of human apoSAA$_1$ (now referred to as SAA1.1) and residues 1-18 of human apoSAA$_4$ (now referred to as SAA4) it was shown that apoSAA$_1$ but not apoSAA$_4$ binds cholesterol at the amino terminal region (Liang et al. (1996) J. Lipid Res. 37:2109-2116).

Furthermore murine SAA2.1, but not murine SAA1.1, was shown to inhibit macrophage acyl CoA:cholesterol acyl transferase (ACAT) activity in culture in intact murine macrophages and in their post-nuclear homogenates in a dose-dependent manner (Ely et al. (2001) *Amyloid* 8:169-181). Further examination of cyanogen bromide generated cleavage fragments of murine SAA2.1 purified by reverse phase HPLC showed murine SAA2.1$_{1-16}$ to have a profound effect inhibiting ACAT activity in a dose-dependent manner. In contrast, murine SAA2.1$_{24-103}$ exhibited no inhibitory effect on ACAT activity (Ely et al. (2001) *Amyloid* 8:169-181).

Murine SAA2.1 has also been shown to stimulate hepatic, macrophage, and pancreatic cholesterol esterase activities in vitro (Lindhorst et al. (1997) Biochim. Biophys. Acta 1339: 143-154; Ely et al. (2001) *Amyloid* 8:169-181; Tam et al. (2002) *J. Lipid Res.* 43:1410-1420). This effect was shown to reside in the 80 residue COOH-terminal region of murine SAA2.1 liberated by cyanogen bromide cleavage (Ely et al. (2001) *Amyloid* 8:169-181). This 80 residue region comprises residues 24-103 of murine SAA2.1.

The ability of HDL-SAA and liposomes containing murine SAA2.1 to cause a marked reduction of acyl CoA:cholesterol acyl transferase activity and enhancement of cholesterol efflux activity was confirmed in macrophages in culture (Tam et al. (2002) *J. Lipid Res.* 43:1410-1420). Intravenous injection of [$^3$H]-cholesterol-loaded macrophages into inflamed mice has also been reported to result in a 3- to 3.5-fold increase in the amount of radiolabeled cholesterol released into the plasma when compared to similarly treated un-inflamed control animals (Tam et al. J. Lipid Res. 2002 43:1410-1420). In this study, macrophage cholesterol efflux was shown to be coupled to the ATP-binding cassette transporter, ABCA1, which is an important protein for the initial step of the reverse cholesterol transport pathway. Furthermore, [$^3$H]-cholesterol-laden macrophages, when pre-treated with HDL-SAA2.1 (murine) in tissue culture and then injected into un-inflamed mice, rapidly released their cholesterol into the plasma (Tam et al. (2002) *J. Lipid Res.* 43:1410-1420). This result was not observed when macrophages were treated with HDL alone.

Thus, isoforms SAA1.1 and SAA2.1 are up-regulated during inflammation; they are evolutionarily conserved; and they are predominantly associated with HDL and HDL's established role in the reverse cholesterol transport pathway (Lindhorst et al. (1997) *Biochim. Biophys. Acta* 1339:143-154; Kisilevsky, R. (1991) *Med. Hypotheses* 35: 337-341; Kisilevsky, R. et al. (1996) *Amyloid* 3: 252-260; and Kisilevsky, R. and Subrahmanyan, L. (1992) *Lab. Invest.* 66: 778-785).

U.S. Pat. No. 5,318,958 discloses methods of potentiating the release and collection of macrophage cholesterol in vivo by administering an effective amount of HDL bound to a ligand having serum amyloid A affinity for HDL. A preferred ligand of this method taught in this patent is serum amyloid A itself.

U.S. Pat. No. 6,004,936 describes similar methods to U.S. Pat. No. 5,318,958. However, in the method claimed in U.S. Pat. No. 6,004,936, the ligand having serum amyloid affinity is not bound to HDL prior to administration. This patent teaches that preferred ligands having serum amyloid affinity are non-amyloidogenic isoforms of serum amyloid A such as SAA2.1.

SUMMARY OF THE INVENTION

Selected peptide domains of mammalian serum amyloid A isoforms 2.1 (SAA2.1) and 1.1 (SAA1.1) and mimetics thereof are demonstrated herein to have a potent enhancing effect on macrophage cholesterol ester hydrolase activity (CEH) and/or an inhibiting effect on acyl CoA:cholesterol acyl transferase (ACAT) activity. As shown herein, these peptides and mimetics thereof shift macrophage cholesterol into a transportable form that is then rapidly exported from the cell in the presence of a cholesterol transporter and a cholesterol acceptor, high density lipoprotein (HDL). Thus, these peptides and mimetics thereof are useful in methods of inhibiting the storage of cholesterol and potentiating the mobilization and release of cholesterol from inflammatory or atherosclerotic sites in a subject. Further, these peptides and mimetics thereof are effective at regressing and/or decreasing formation of arterial atherosclerotic lesions and treating or preventing atherosclerosis, cardiovascular disease, coronary heart disease and inflammation in a subject.

Accordingly, the present invention provides peptides and compounds and mimetics of these peptides and compounds and pharmaceutical compositions comprising these peptides or portions thereof, compounds and mimetics of these peptides or portions thereof or compounds, and methods for use of these peptides, compounds and pharmaceutical compositions to modify the activity of the macrophage cholesterol metabolizing enzyme cholesterol ester hydrolase and/or acyl CoA:cholesterol acyl transferase.

One aspect of the present invention relates to a peptide, a peptide variant or mimetic thereof of the cholesterol ester hydrolase enhancing domain or the acyl CoA:cholesterol acyl transferase inhibitory domain of SAA proteins. Cholesterol ester hydrolase enhancing domains have now been identified as residing in residues 74-103 of the C-terminus of murine SAA2.1 and residues 77-103 of the C-terminus of murine SAA1.1. An acyl CoA:cholesterol acyl transferase inhibitory domain resides in residues 1-16 of the N-terminus of murine SAA2.1 and in residues 1-23 of the N-terminus of human SAA1.1 and SAA2.1.

Preferred peptides or mimetics thereof capable of enhancing cholesterol ester hydrolase activity include an isolated peptide or a mimetic thereof comprising a formula $X_1X_2X_3X_4X_5X_6X_7X_8X_9X_{10}X_{11}X_{12}X_{13}X_{14}X_{15}X_{16}X_{17}X_{18}$ (SEQ ID NO:29) or a portion thereof wherein $X_1$ and $X_9$, $X_{12}$ or $X_{18}$ are amino acids capable of forming a salt bridge, $X_6$ is glutamic acid or lysine or an amino acid which is a conservative substitution thereof, and $X_2$, $X_3$, $X_4$, $X_5$, $X_7$, $X_8$, $X_{10}$, $X_{11}$, $X_{13}$, $X_{14}$, $X_{15}$, $X_{16}$, and $X_{17}$ are independently any amino acid. Also preferred are peptides comprising DTIADQEANRHGRSGKDPNYYRPPGLPDKY (SEQ ID NO:4); ADQEANRHGRSGKDPNYYRPPGLPDKY (SEQ ID NO:8); ADQEANRHGRSGKDPNYYRPPGLPAKY (D-form; SEQ ID NO:10); ADQAANEWGRSGKDPNHFRPAGLPEKY (D-form; SEQ ID NO:31); ADQEANRHGRSGKDPNYYR (SEQ ID NO:25); ADQAANKWGRSGRDPNHFR (SEQ ID NO:11); ADQAANEWGRSGKDPNHFR (SEQ ID NO:12); ADQAANEWGRSGKDPNHFR (D-form; SEQ ID NO:32);

or DQAANKWGRSGRDPNHFR (SEQ ID NO:26), or mimetics thereof and peptide variant or mimetics thereof of a peptide comprising DTIADQEANRHGRSGKDPNYYRPPGLPDKY (SEQ ID NO:4); ADQEANRHGRSGKDPNYYRPPGLPDKY (SEQ ID NO:8); ADQEANRHGRSGKDPNYYRPPGLPAKY (SEQ ID NO:9); ADQEANRHGRSGKDPNYYRPPGLPAKY (D-form; SEQ ID NO:10); ADQAANEWGRSGKDPNHFRPAGLPEKY (SEQ ID NO:24); ADQAANEWGRSGKDPNHFRPAGLPEKY (D-form; SEQ ID NO:31); ADQEANRHGRSGKDPNYYR (SEQ ID NO:25); ADQAANKWGRSGRDPNHFR (SEQ ID NO:11); ADQAANEWGRSGKDPNHFR (SEQ ID NO:12); ADQAANEWGRSGKDPNHFR (D-form; SEQ ID NO:32); or DQAANKWGRSGRDPNHFR (SEQ ID NO:26) or a portion thereof. Excluded from the scope of peptides of the present invention capable of enhancing cholesterol ester hydrolase activity are those isolated peptides consisting of GFFSFIGEAFQGAGDMWRAYTDMKEAGWKDGDKYFHARGNYDAAQRGPGGVWAAEKISDA RESFQEFFGRGHEDTMADQEANRHGRSGKDPNYYRPPGLPAKY (full length murine SAA1.1; SEQ ID NO:18); GFFSFVHEAFQGAGDMWRAYTDMKEANWKNSDKYFHARGNYDAAQRGPGGVWAAEKISDG REAFQEFFGRGHEDTIADQEANRHGRSGKDPNYYRPPGLPDKY (full length murine SAA2.1; SEQ ID NO:19); RSFFSFLGEAFDGARDMWRAYSDMREANYIGSDKYFHARGNYDAAKRGPGGVWAAEAISD ARENIQRFFGHGAEDSLADQAANEWGRSGKDPNHFRPAGLPEKY (full length human SAA1.1; SEQ ID NO:20); RSFFSFLGEAFDGARDMWRAYSDMREANYIGSDKYFHARGNYDAAKRGPGGAWAAEVISN ARENIQRLTGHGAEDSLADQAANKWGRSGRDPNHFRPAGLPEKY (full length human SAA2.1; SEQ ID NO:21); KEAGWKDGDKYFHARGNYDAAQRGPGGVWAAEKISDARESFQEFFGRGHEDTMADQEAN RHGRSGKDPNYYRPPGLPAKY (SEQ ID NO:22); KEANWKNSDKYFHARGNYDAAQRGPGGVWAAEKISDGREAFQEFFGRGHEDTIDQEANR HGRSGKDPNYYRPPGLPDKY (SEQ ID NO:23); ADQEANRHGRSGKDPNYYRPPGLPAKY (SEQ ID NO:9); or ADQAANEWGRSGKDPNHFRPAGLPEKY (SEQ ID NO:24).

Preferred peptides of the present invention capable of inhibiting acyl CoA:cholesterol acyl transferase activity include an isolated peptide or a peptide variant or portion thereof, or a similar region of the N-terminus of human SAA1.1 or SAA2.1, e.g. amino acids 1-20 of human SAA1.1 or human SAA2.1 (RSFFSFLGEAFDGARDMWRA (SEQ ID NO:30)) or peptide variants or portions thereof comprising a formula $(X)_n FFX_1 FX_2 X_3 X_4 X_5 FX_6$ or a portion thereof wherein F is phenylalanine or an amino acid which is a conservative substitution thereof, and n is 1 or 2. When n is 1, the isolated peptide comprises $XFFX_1 FX_2 X_3 X_4 X_5 FX_6$ (SEQ ID NO:13) wherein F is phenylalanine or an amino acid which is a conservative substitution thereof, X, $X_1$, $X_4$, $X_5$ and $X_6$ are independently any amino acid, $X_2$ is a hydrophobic or nonpolar amino acid, and $X_3$ is histidine or an amino acid which is a conservative substitution thereof. When n is 2, the isolated peptide comprises $X_a X_b FFX_1 FX_2 X_3 X_4 X_5 FX_6$ (SEQ ID NO:14), wherein F is phenylalanine or an amino acid which is a conservative substitution thereof, $X_a$ and $X_6$ are amino acids capable of forming a salt bridge, and $X_b$, X, $X_1$, $X_2$, $X_3$, $X_4$ and $X_5$ are independently any amino acid. Also preferred are isolated peptides comprising GFFSFVHEAFQGAGDMWRAY (SEQ ID NO:1), RSFFSFLGEAFDGARDMWRAYSD (SEQ ID NO:6), or RGFFSFIGEAFQGAGDMWRAY (SEQ ID NO:7) or a peptide variant of one of these peptides or a portion thereof, e.g. amino acids 1-20 of human SAA1.1 or human SAA2.1 (RSFFSFLGEAFDGARDMWRA (SEQ ID NO:30)). Excluded from the scope of the peptides of the present invention capable of inhibiting acyl CoA:cholesterol acyl transferase activity are those isolated peptides consisting of GFFSFVHEAFQGAGDM (SEQ ID NO:15), GFFSFIGEAFQGAGDM (SEQ ID NO:16), RSFFSFLGEAFDGARDMW (SEQ ID NO:17), GFFSFIGEAFQGAGDMWRAYTDMKEAGWKDGDKYFHARGNYDAAQRGPGGVWAAEKISD ARESFQEFFGRGHEDTMADQEANRHGRSGKDPNYYRPPGLPAKY (full length murine SAA1.1; SEQ ID NO:18); GFFSFVHEAFQGAGDMWRAYTDMKEANWKNSDKYFHARGNYDAAQRGPGGVWAAEKISD GREAFQEFFGRGHEDTIADQEANRHGRSGKDPNYYRPPGLPDKY (full length murine SAA2.1; SEQ ID NO:19); RSFFSFLGEAFDGARDMWRAYSDMREANYIGSDKYFHARGNYDAAKRGPGGVWAAEAIS DARENIQRFFGHGAEDSLADQAANEWGRSGKDPNHFRPAGLPEKY (full length human SAA1.1; SEQ ID NO:20); or RSFFSFLGEAFDGARDMWRAYSDMREANYIGSDKYFHARGNYDAAKRGPGGAWAAEVIS NARENIQRLTGHGAEDSLADQAANKWGRSGRDPNHFRPAGLPEKY (full length human SAA2.1;SEQ ID NO:21).

Preferred variants include, but are not limited to, cyclic peptides and peptides comprising one or more D amino acids, which are at least equally effective and superior in some embodiments but less susceptible to degradation in vivo.

Also preferred is a variant comprising two or more linked or conjugated peptides of the present invention. Particularly preferred is a variant comprising a peptide capable of enhancing cholesterol ester hydrolase activity linked or conjugated to a peptide capable of inhibiting acyl CoA:cholesterol acyl transferase activity. Also preferred in certain embodiments is that at least one of these peptides contain one or more D amino acids.

The present invention also relates to mimetics of any of the above peptides, peptide variants or portions thereof.

Another aspect of the present invention relates to compounds with a formula of Y-Z or Q-Y-Z, wherein Y comprises an isolated peptide or mimetic of the present invention with cholesterol ester hydrolase enhancing activity and/or acyl CoA:cholesterol acyl transferase inhibitory activity; Z comprises a compound linked to Y that enhances the performance of Y; and in embodiments comprising Q, Q may comprise another compound linked to Y-Z which also enhances performance of the Q-Y-Z compound. Q may be identical to Z or different from Z. Exemplary Z or Q compounds include, but are not limited to a targeting agent, a second agent for treatment of atherosclerosis, cardiovascular disease or coronary heart disease, an agent which enhances solubility, absorption, distribution, half-life, bioavailability, stability, activity and/or efficacy, or an agent which reduces toxicity or side effects of the compound. Exemplary targeting agents of Z and/or Q include macrophage targeting agents such as, for example, a liposome, a microsphere, or a ligand for a SAA receptor, hepatic targeting agents, antibodies and active fragments thereof such as, for example, Fab fragments, and additional agents specific to atherosclerotic plaques and/or inflammatory sites.

Another aspect of the present invention relates to pharmaceutical compositions comprising a peptide, peptide variant or portion thereof, a Y-Z or Q-Y-Z compound, or a mimetic of these, which inhibits acyl CoA:cholesterol acyl transferase activity and/or enhances cholesterol ester hydrolase activity. Pharmaceutical compositions of the present invention further comprise a vehicle suitable pharmaceutically for in vivo administration. In one embodiment, the isolated peptide or mimetic thereof or the compound is complexed with a lipid. A phospholipid vesicle which encapsulates the peptide or mimetic thereof or the compound can also be used. In other embodiments, vehicles suitable for pharmaceutical administration in vivo may comprise aqueous solutions including, but not limited to, phosphate buffered saline or phosphate buffered saline containing glucose, preferably 0.01 to 10% weight/volume glucose, more preferably 5% weight/volume glucose.

Another aspect of the present invention relates to the use of these peptides, compounds and mimetics of these, or pharmaceutical compositions comprising these peptides, compounds and mimetics of these, to modify an activity of a cholesterol-metabolizing enzyme. In particular, the activity of cholesterol ester hydrolase and/or acyl CoA:cholesterol acyl transferase can be modified using a peptide, compound or mimetic of these, or a pharmaceutical composition comprising a peptide, compound or mimetic of these of the present invention. In a preferred embodiment of the present invention, the enzymatic activity is modified in vivo. More preferred is modification of the enzymatic activity in humans.

Another aspect of the present invention relates to use of these peptides, compounds and mimetics of these, or pharmaceutical compositions comprising these peptides, compounds and mimetics of these, to increase and/or promote the mobilization and efflux of stored cholesterol from macrophages located in atherosclerotic plaques. In a preferred embodiment of the present invention, the increase and/or promotion of the mobilization and efflux of stored cholesterol from macrophages located in atherosclerotic plaques occurs in vivo. More preferred is increase and/or promotion of the mobilization and efflux of stored cholesterol from macrophages located in atherosclerotic plaques in humans.

Another aspect of the present invention relates to use of these peptides, compounds and mimetics of these or pharmaceutical compositions comprising these peptides, compounds and mimetics of these to increase and/or promote the mobilization and efflux of stored cholesterol from macrophages located at sites of inflammation. In a preferred embodiment of the present invention, the increase and/or promotion of the mobilization and efflux of stored cholesterol from macrophages located at sites of inflammation occurs in vivo. More preferred is increase and/or promotion of the mobilization and efflux of stored cholesterol from macrophages located at sites of inflammation in humans.

Another aspect of the present invention relates to methods for treating or preventing atherosclerosis in a subject comprising administering to the subject a peptide, compound, or a mimetic of these or a pharmaceutical composition of the present invention. In a preferred embodiment the subject is a human.

Another aspect of the present invention relates to methods for treatment of cardiovascular disease comprising administering to a subject a peptide, compound, or mimetic of these or a pharmaceutical composition of the present invention. In a preferred embodiment the subject is a human.

Another aspect of the present invention relates to methods for treatment of coronary heart disease comprising administering to a subject a peptide, compound, or mimetic of these or a pharmaceutical composition of the present invention. In a preferred embodiment the subject is a human.

Yet another aspect of the present invention relates to methods for treating or preventing inflammation in a subject comprising administering to the subject a peptide, compound, or mimetic of these or a pharmaceutical composition of the present invention. In a preferred embodiment the subject is a human.

BRIEF DESCRIPTION OF THE FIGURES

In FIG. 3A, the X-axis, concentration, is depicted on a linear scale and in FIG. 3B the X-axis, concentration, is depicted on a logarithmic scale. As shown by these graphs, each of the peptides alone increased cholesterol efflux in response to increased dose. Further, a combination of the two peptides produced a greater than additive effect.

In FIG. 5A, the X-axis, concentration, is depicted on a linear scale and in FIG. 5B, the X-axis, concentration, is depicted on a logarithmic scale. As shown by these graphs, the human SAA1.1 peptide was at least as effective if not more effective at increasing cholesterol efflux in response to increased dose than the mouse peptide.

FIG. 7B is inclusive of data presented in FIG. 7A as well as additional data from a subsequent experiment performed under the same conditions. In these experiments, animals were placed on an atherogenic diet (Paigen's Atherogenic Rodent Diet: Purina 5015 with cocoa butter, cholesterol and cholic acid (CI3002, Research Diets, Inc.)) for four weeks, following which they were divided into two groups. One group continued on the diet for an additional two weeks. The other group continued on the diet for the same period but also received once every four days liposomes containing a peptide corresponding to amino acids 1-20 of murine SAA2.1 (SEQ ID NO:1; Group B of FIG. 7A; hf+p1 of FIG. 7B) or liposomes containing a peptide corresponding to amino acids 74-103 of murine SAA2.1 (SEQ ID NO:4; Group D of FIG. 7A; hf+p4 of FIG. 7B). The control group received high fat diet alone with no liposomes (Group A of FIG. 7A; high fat of FIG. 7B). An additional group was placed on a normal mouse chow diet (Group C of FIG. 7A; low fat of FIG. 7B). An additional Group receiving liposomes containing a peptide corresponding to amino acids 1-20 of murine SAA2.1 (SEQ ID NO:1) and liposomes containing a peptide corresponding to amino acids 74-103 of murine SAA2.1 (SEQ ID NO:4) is depicted in FIG. 7B and is referred to as hf+p1+p4. After the two weeks, the mice were killed and their aortas were dissected and stained with Oil Red O. Data of FIG. 7A depict the area stained with Oil Red O indicative of the actual lipid positive area or areas as a percentage of the total aortic area viewed. Data of FIG. 7B depict the area stained with Oil Red O as a percentage relative to the high fat diet group (100%). Five animals were used in each group in FIG. 7A. The number of animals in each Group depicted in FIG. 7B is set forth as n.

FIG. 8B is inclusive of data presented in FIG. 8A as well as additional data from a subsequent experiment performed under the same conditions. In the prevention experiments depicted in FIG. 8A, ApoE knockout mice were placed on a high fat diet and also received once every four days liposomes containing a peptide corresponding to amino acids 1-20 of murine SAA2.1 (SEQ ID NO:1; Group 2), liposomes containing a peptide corresponding to amino acids 74-103 of murine SAA2.1 (SEQ ID NO:4; Group 4) or liposomes containing a peptide corresponding to amino acids 1-20 of murine SAA2.1 and a peptide corresponding to amino acids 74-103 of murine SAA2.1 (SEQ ID NO:1+SEQ ID NO:4; Group 5). The control group received high fat diet alone with no liposomes (Group 1). An additional group was placed on a normal mouse chow diet (group 3). After 20 days, the mice were killed and their aortas were dissected and stained with Oil Red O. Data of FIG. 8A depict the area stained with Oil Red O indicative of actual lipid positive area or areas as a percentage of the total aortic area viewed. In FIG. 8A, five animals were used in Groups 1-3 and 5. Four animals were used in Group 4 as one animal died during the experiment. In FIG. 8B an additional experimental group referred to as "empty lipos" was included which are animals that were treated with empty liposomes identical to those used in the peptide containing formulations but which are protein-peptide free. This group is different from the high fat and low fat (diet) groups that were not treated with liposomes. Data in FIG. 8B is expressed as the area stained with Oil Red O as a percentage relative to the high fat diet group (100%). In FIG. 8B the number of animals is set forth as n. Group referred to as "high fat", "low fat", "hf+p1", "hf+p4" and hf+p(1+4) correspond to Groups 1, 3, 2, 4 and 5, respectively of FIG. 8A.

DETAILED DESCRIPTION OF THE INVENTION

Figure 1:
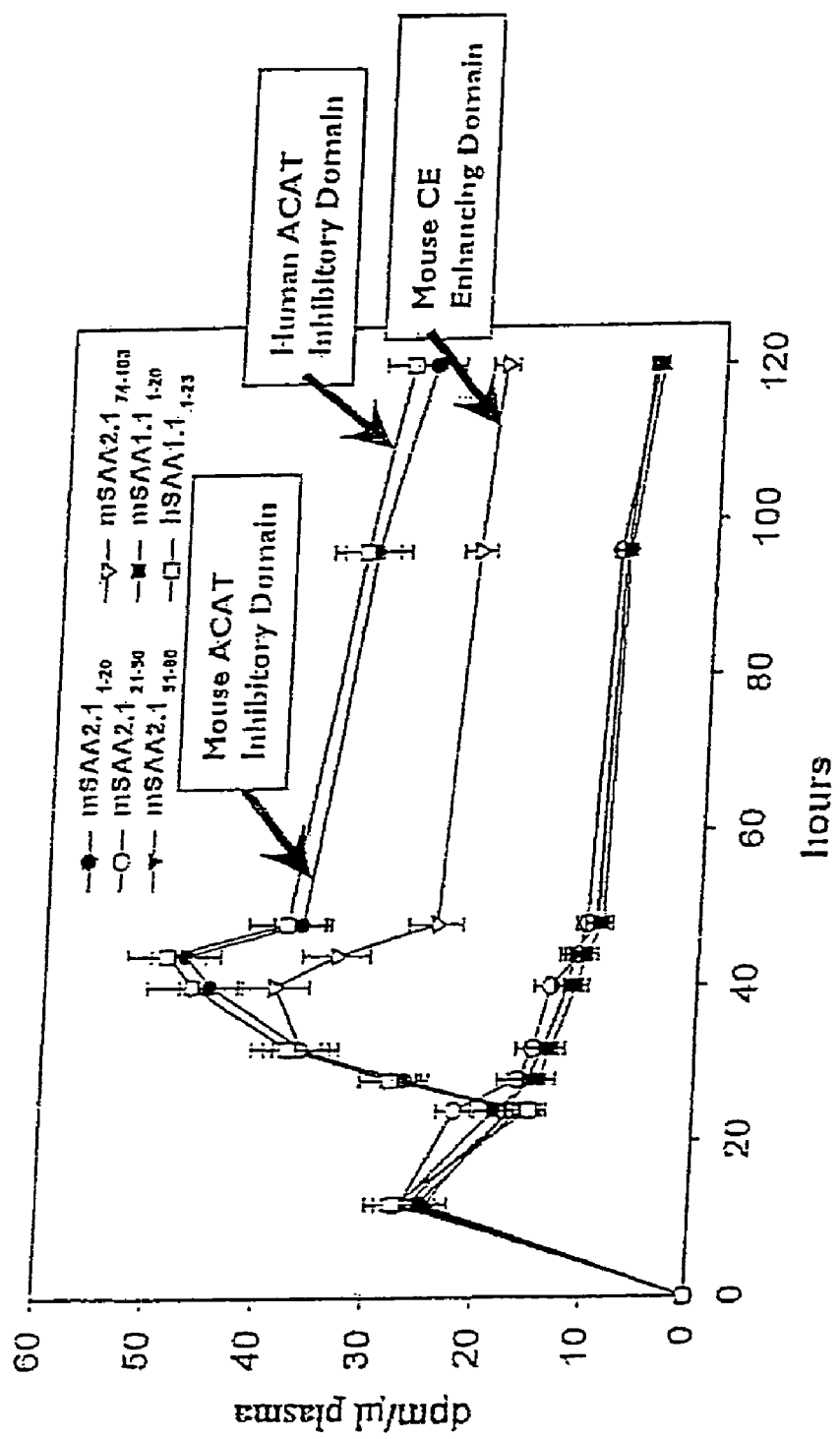
FIG. 1 is a line graph of results from experiments examining the in vivo effects of liposomes containing various SAA2.1 synthetic peptides on macrophage cholesterol efflux. Results for liposomes containing the synthetic peptide of amino acids 1 through 20 (SEQ ID NO:1) of mouse SAA2.1 are depicted as closed circles. Results for liposomes containing the synthetic peptide of amino acids 21 through 50 (SEQ ID NO:2) of mouse SAA2.1 are depicted as open circles. Results for liposomes containing the synthetic peptide of amino acids 51 through 80 (SEQ ID NO:3) of mouse SAA2.1 are depicted as closed triangles. Results for liposomes containing the synthetic peptide of amino acids 74 through 103 (SEQ ID NO:4) of mouse SAA2.1 are depicted as open triangles. Results for liposomes containing the synthetic peptide of amino acids 1 through 20 (SEQ ID NO:5) of mouse SAA1.1 are depicted as closed squares. Results for liposomes containing the synthetic peptide of amino acids 1-23 (SEQ ID NO:6) of human SAA1.1 are depicted as open squares.
Figure 2:
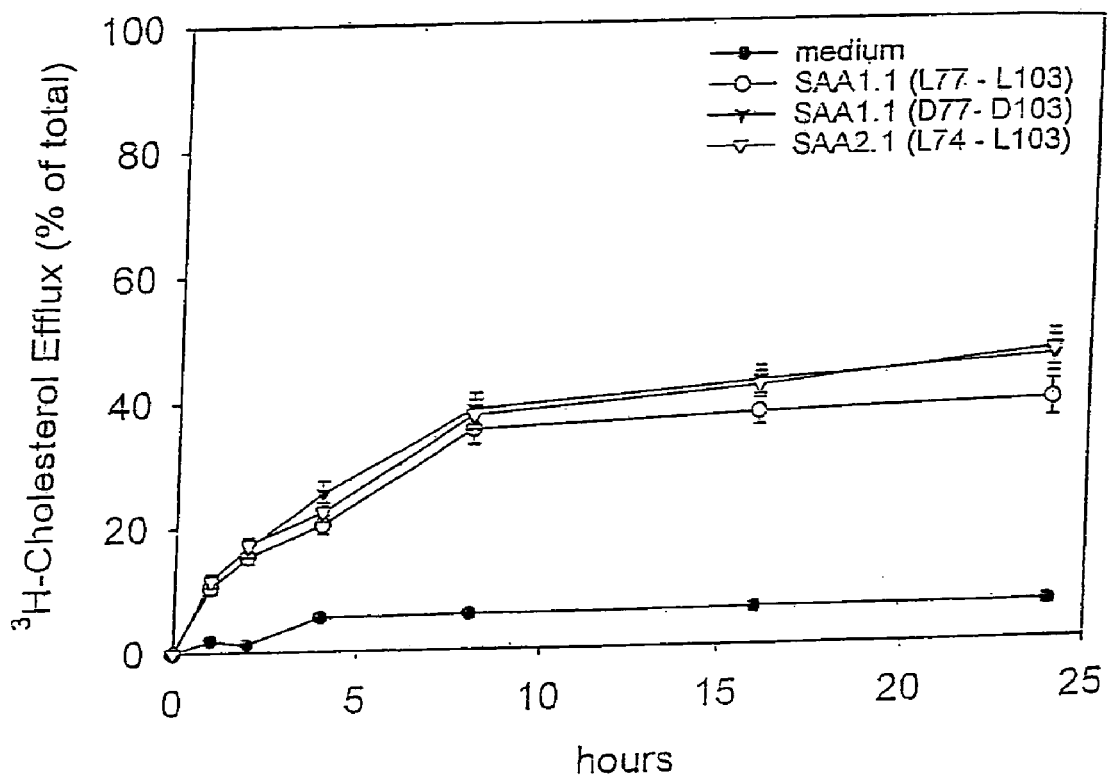
FIG. 2 is a line graph depicting cholesterol efflux in tissue culture mediated by L-form (SEQ ID NO:9) and D-form (SEQ ID NO:10) amino acid peptides corresponding to residues 77-103 of murine SAA1.1. Cholesterol efflux following treatment with liposomes containing 0.5 μM cyanogen bromide-released peptides corresponding to amino acid residues 77-103 of murine SAA1.1 is depicted by open circles. Cholesterol efflux following treatment with liposomes containing synthetic D-form (SEQ ID NO:10) amino acid peptides of the corresponding sequence is depicted by closed triangles. Cholesterol efflux following treatment with liposomes containing the native L-form amino acid residues 74-103 of murine SAA2.1 is depicted by inverted open triangles. Control, a chase efflux medium consisting of DMEM/BSA alone, is depicted as closed circles. The results represent cholesterol efflux to the acceptor, HDL, in the medium from cells after pre-treatment with these liposomes. At various time points, the efflux media were collected and analyzed for [$^3$H] cholesterol. Total [$^3$H] cholesterol was (1.8-2.1)×10$^6$ dpm/mg cell protein. Results are the mean ±SEM of four determinations.

Approximately 13 million North Americans are taking cholesterol-lowering drugs, and the majority of these individuals are now treated with the category of drugs known as statins. Cholesterol synthesis inhibitors (statins) are for the most part considered safe and highly effective. However, there have been some recent setbacks for this drug class. For example, the 2001 voluntary recall of Bayer's statin Baycol™, the delayed North American introduction of AstraZeneca's statin Crestor™, and the recent concerns about the health risks associated with long-term statin use (Clearfield, M. B., (2002) *Expert Opin. Pharmacother.* 3:469-477) are indicative of the need for new drugs.

Thus, pharmaceutical companies are currently developing drugs that work via different mechanisms from that of the current marketed drugs. Treatment with two or more drugs that act through different mechanisms can, in fact, be additive or synergistic in their combined ability to reduce cholesterol levels (Brown, W. V. (2001) *Am. J. Cardiol.* 87(5A): 23B-27B; Buckert, E. (2002) *Cardiology* 97: 59-66). Ezetimibe (Zetia™, Merck), which was recently approved by the FDA, can significantly reduce cholesterol levels by itself. Furthermore, since Ezetimibe works by decreasing cholesterol absorption (i.e. blocks cholesterol transport), it can also be given with cholesterol synthesis inhibitors (statins) to decrease plasma cholesterol levels to a greater extent than when either drug is given alone (Davis et al. (2001) *Arterioscler Thromb Vasc Biol.* 21: 2031-2038; Rader, D. J. (2002) *Am. J. Managed Care* 8 (2 Suppl): S40-44).

Other drugs such as Avasimibe (Pfizer), Eflucimibe (Eli Lilly) and CS-505 (Sankyo), which are in clinical trials, are aimed at inhibiting acyl CoA:cholesterol acyl transferase (ACAT) activity.

Companies such as Esperion Therapeutics, Tularik Inc. and the Canadian company, Xenon Genetics are developing ways to increase the levels of HDL, the so-called "good cholesterol", which plays a key role in the reverse cholesterol transport pathway, known to be important for the excretion of cholesterol out of the body.

However, while there has been considerable effort by pharmaceutical companies to produce new compounds for treating atherosclerosis, there are currently no drugs on the market that have the ability to promote the mobilization and efflux of stored cholesterol from macrophages located in atherosclerotic plaques by enhancing cholesterol ester hydrolase activity.

The accumulation of cholesterol in vascular cells such as macrophages is a defining pathological feature of atherosclerosis. Macrophages are key cells in the storage and removal of lipids. Their conversion to foam cells (cholesterol-laden macrophages) is an early and important pathological process in the formation of an atherosclerotic plaque.

Two enzymes are critical for maintaining cellular cholesterol balance.

Cholesterol ester hydrolase, also referred to as cholesterol esterase and cholesteryl ester hydrolase, promotes the removal or efflux of cholesterol from macrophages. This enzyme exists in an acidic as well as a neutral form and all aspects of the present invention are applicable to both forms, with modulation of the neutral form being preferred.

Acyl CoA:cholesterol acyl transferase promotes the storage of macrophage cholesterol. During an acute phase inflammatory response, serum amyloid A (SAA) isoforms 1.1 and 2.1 become major constituents of high density lipoprotein and this complex is internalized by macrophages. As shown herein, murine SAA2.1, but not murine SAA1.1, inhibits acyl CoA:cholesterol acyl transferase activity and enhances cholesterol ester hydrolase activity, shifting the balance to the transportable form of cholesterol. Serum amyloid A (SAA) has been demonstrated to have a specific binding affinity for macrophages, separate from apoA-1 binding affinity for macrophages. Murine isoform 2.1 is the first protein shown to both enhance cholesterol ester hydrolase activity and inhibit acyl CoA:cholesterol acyl transferase activity. However, as evidenced herein, human SAA1.1 and human SAA2.1 comprise peptide domains that enhance cholesterol ester hydrolase activity and inhibit acyl CoA:cholesterol acyl transferase activity.

The in vitro effects of acute phase-HDL (AP-HDL;HDL-SAA) on acyl CoA:cholesterol acyl transferase and cholesterol ester hydrolase activities and on cellular cholesterol export were studied by the inventors using purified enzymes, cell homogenates, and whole cells. Results from in vitro studies using macrophage post-nuclear homogenates as a source of acyl CoA:cholesterol acyl transferase showed murine SAA2.1 to inhibit acyl CoA:cholesterol acyl transferase activity in a dose-dependent manner. In contrast, murine SAA1.1 and apoA-1 had no effect. AP-HDL, as well as liposomes containing murine SAA2.1, were also shown by the inventors to cause a marked reduction of acyl CoA:cholesterol acyl transferase activity and enhancement of cholesterol ester hydrolase activity in intact cholesterol-laden macrophages in tissue culture. In contrast, HDL alone, SAA2.1-free liposomes, and liposomes containing murine SAA1.1 or apoA-1 had no effect on enzyme activities. Using macrophages preloaded with radio-labeled cholesterol and injected intravenously into either inflamed or un-inflamed mice, it was shown that the inflamed mice, which have high SAA2.1 levels, effluxed cholesterol more rapidly and to a greater extent (6-fold greater) than their un-inflamed counterparts. Further, using cholesterol-loaded macrophages pretreated with liposomes containing either murine SAA1.1, murine SAA2.1, or apoA-1 and then injected intravenously into un-inflamed mice, the inventors have now shown that only liposomes containing murine isoform 2.1 recapitulated the major cholesterol releasing effect seen in inflamed mice.

Using both in vitro and in vivo assays, these unique properties of murine SAA2.1 have been demonstrated to reside in two peptide domains. The acyl CoA:cholesterol acyl transferase inhibitory domain of murine SAA2.1 resides in residues 1-16 of the N-terminus of SAA2.1. This N-terminal 16-residue domain released by cyanogen bromide cleavage of murine SAA2.1, produced no effect, however, on cholesterol ester hydrolase activity. Instead, the C-terminal 30-residue domain of murine SAA2.1 correlating to amino acids 74-103 of murine SAA2.1 has now been identified as the region of murine SAA2.1 that enhances cholesterol ester hydrolase activity. In particular, the cholesterol ester hydrolase activity-enhancing domain has been identified as correlating to amino acids 77-95 of murine SAA2.1.

As shown herein, isolated peptides with amino acid sequences comprising these domains within murine SAA2.1 and human SAA1.1 and human SAA2.1 have a potent enhancing effect on macrophage cholesterol ester hydrolase activity and an inhibiting effect on acyl CoA:cholesterol acyl transferase activity both in vitro and in vivo. Peptides synthesized to contain the amino acid sequences of these domains or portions thereof have the ability to shift macrophage cholesterol into a transportable form that is then rapidly exported from the cell in the presence of a functional cholesterol transporter and cholesterol acceptor high density lipoprotein. Further, these isolated peptides are extremely active, as a single treatment intravenously or orally mobilizes macrophage cholesterol in vivo for over 4 days.

Peptides corresponding to amino acid residues 1-20 (GFFSFVHEAFQGAGDMWRAY; SEQ ID NO:1), 21-50 (TDMKEANWKNSDKYFHARGNYDAAQRGPGG; SEQ ID NO:2), 51-80 (VWAAEKISDGREAFQEFFGRGHEDTIADQE; SEQ ID NO:3) and 74-103 (DTIADQEANRHGRSGKDPNYYRPPGLPDKY; SEQ ID NO:4) of murine SAA2.1 protein sequence, respectively, were synthesized by solid-phase peptide synthesis. Peptides corresponding to amino acid residues 1-23 (RSFFSFLGEAFDGARDMWRAYSD; SEQ ID NO:6) and 1-20 (RSFFSFLGEAFDGARDMWRA; SEQ ID NO:30) of human SAA1.1 and/or human SAA2.1 were also synthesized as well as peptides corresponding to residues 78-96 of human SAA2.1 (ADQAANKWGRSGRDPNHFR; SEQ ID NO:11), residues 79-96 of human SAA2.1 (DQAANKWGRSGRDPNHFR; SEQ ID NO:26), residues 80-96 of human SAA2.1 (QAANKWGRSGRDPNHFR; SEQ ID NO:27) and residues 81-96 of human SAA2.1 (AANKWGRSGRDPNHFR; SEQ ID NO:28). In addition, a peptide corresponding to amino acid residues 1-20 (GFFSFIGEAFQGAGDMWRAY; SEQ ID NO:5) of murine SAA1.1 protein sequence was synthesized, as well as a peptide corresponding to amino acid residues 1-20 of murine SAA1.1 protein sequence plus an arginine at the N-terminus (RGFFSFIGEAFQGAGDMWRAY; SEQ ID NO:7). Synthetic peptides SEQ ID NO: 1 through 7 comprise L amino acids. These synthetic peptides of the present invention are nonglycosylated, as are the native forms of SAA1.1 and SAA2.1.

Further, cyanogen bromide cleavage of murine SAA2.1 has been shown to generate an insoluble 16-mer (SAA2.1 $_{1-16}$) and two soluble fragments, a 7-mer (SAA2.1 $_{17-23}$) and an 80-mer (SAA2.1 $_{24-103}$; depicted herein as SEQ ID NO:23) (Ancsin, J. et al. J. Biol. Chem. 274: 7172-7181,1999). For murine SAA1.1, a substitution of Ile with Met at residue 76 introduces an additional cleavage site, allowing the 80-mer to be cleaved into a 53-mer (SAA1.1 $_{24-76}$) and a 27-mer (SAA1.1 $_{77-103}$). The last 27 residues of murine SAA2.1 and SAA1.1 are as follows:

SAA2.1 $_{77-103}$ ADQEANRHGRSGKDPNYYRPPGLP<u>D</u>KY (SEQ ID NO:8)

SAA1.1 $_{77-103}$ ADQEANRHGRSGKDPNYYRPPGLP<u>A</u>KY (SEQ ID NO:9)

The only difference in amino acid residues in these two sequences resides at position 101 (bold and underlined).

These synthetic peptides were used to map a domain in SAA2.1 that is responsible for modulating cholesterol ester hydrolase and to identify compositions useful in modulating cholesterol ester hydrolase activity and/or acyl CoA: cholesterol acyl transferase activity.

As shown herein, pre-incubation of J774 macrophages with liposomes containing 0.5 µM synthetic peptide corresponding to amino acid residues 74-103 of murine SAA2.1 (SEQ ID NO:4) resulted in a significant increase in the rate of macrophage [$^3$H] cholesterol efflux into medium containing HDL. Liposomes containing a shorter peptide generated from the CNBr cleavage of native murine SAA1.1 protein (SAA1.1 $_{77-103}$; SEQ ID NO:9) have also now been found by the inventors to have a similar effect. Specifically, [$^3$H] cholesterol efflux into the medium was demonstrated to be similar in both murine SAA1.1$_{77-103}$-treated and murine SAA2.1$_{74-103}$-treated macrophages.

These data indicate that residues 74-76 of murine SAA may not be necessary in promoting macrophage cholesterol efflux. Further, residue 101 is believed to be unnecessary. In fact, an examination of the sequences of approximately 12 species indicates that the terminal 8 residues of SAA1.1 and 2.1, which are rich in proline, are likely unnecessary for CEH enhancing activity. Accordingly, it is believed that a peptide of 19 residues from amino acids 77 through 95 of murine SAA2.1 possesses the CEH enhancing property. Further, a peptide comprising the consensus sequence ADQAANEWGRSGKDPNHFR (SEQ ID NO:12) corresponding to residues 78 through 96 of human SAA1.1 and peptides corresponding to residues 78 through 96 of human SAA2.1 (ADQAANKWGRSGRDPNHFR; SEQ ID NO:11) and residues 79 through 96 of human SAA2.1 (DQAANKWGRSGRDPNHFR; SEQ ID NO:26) are shown herein to increase export of cholesterol. Thus, this peptide and peptides corresponding to residues 78 through 96 of human SAA2.1 (ADQAANKWGRSGRDPNHFR; SEQ ID NO:11) and residues 79 through 96 of human SAA2.1 (DQAANKWGRSGRDPNHFR; SEQ ID NO:26) are believed to possess CEH enhancing activity as well.

Additionally, these data further elucidate the differences between the tertiary structures (i.e., 3-dimensional structures, protein folding) of SAA1.1 and SAA2.1, since, unlike SAA2.1, the native SAA1.1 protein does not promote macrophage cholesterol efflux. This information and additional modeling work is useful in the molecular modeling of the SAA protein and peptides for the design of small molecule mimetics.

Modifications of such peptides to comprise one or more D amino acids were also shown by the inventors to result in equally effective and in some embodiments superior peptides also expected to be more stable and less susceptible to degradation in vivo. These modified peptides are demonstrated herein to be effective at increasing cholesterol efflux in vitro in both mouse and human cell culture experiments and in vivo in a subject upon intravenous and oral administration of an aqueous solution of D amino acid containing peptide. See, for example, FIGS. 2, 11, 12 and 15.

A synthetic peptide corresponding to amino acid sequence 77-103 of murine SAA1.1 which consists of all D-amino acids (D-form ADQEANRHGRSGKDPNYYRPPGLPAKY, referred to herein as SEQ ID NO:10), had a similar effect in enhancing macrophage cholesterol export into the medium when cells were treated in parallel with the corresponding native L-amino acid peptide of murine SAA1.1. Additional D-form peptides of the present invention synthesized include the peptide ADQAANEWGRSGKDPNHFRPAGLPEKY (D-form; SEQ ID NO:31) corresponding to amino acids 78-104 of human SAA1.1 and the peptide ADQAANEWGRSGKDPNHFR (D-form; SEQ ID NO:32)

corresponding to the consensus sequence of residues 78 through 96 of human SAA1.1 and human SAA2.2.

Figure 11:
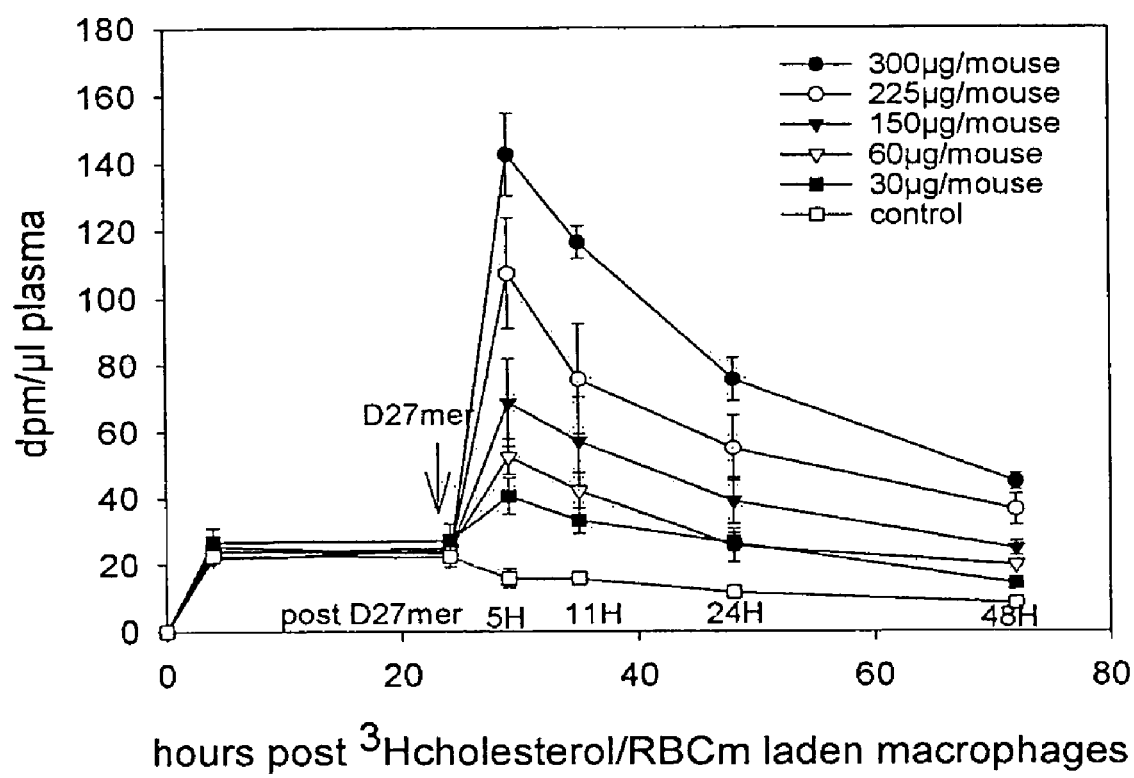
FIG. 11 is a line graph showing dosage curves for in vivo cholesterol efflux in mice injected with J774 macrophages cholesterol-loaded with RBC membranes and [$^3$H]-cholesterol, and administered increasing intravenous dosages of non-liposome formulated D-27mer peptide (SEQ ID NO:10) dissolved in phosphate buffered saline. Cholesterol efflux in mice administered 30 µg of the D-27mer peptide (SEQ ID NO:10) dissolved in phosphate buffered saline is depicted as filled squares. Cholesterol efflux in mice administered 60 µg of the D-27mer peptide (SEQ ID NO:10) dissolved in phosphate buffered saline is depicted as open triangles. Cholesterol efflux in mice administered 150 µg of the D-27mer peptide (SEQ ID NO:10) dissolved in phosphate buffered saline is depicted as filled triangles. Cholesterol efflux in mice administered 225 µg of the D-27mer peptide (SEQ ID NO:10) dissolved in phosphate buffered saline is depicted as open circles. Cholesterol efflux in mice administered 300 µg of the D-27mer peptide (SEQ ID NO:10) dissolved in phosphate buffered saline is depicted as filled circles. Cholesterol efflux in control mice administered phosphate buffered saline is depicted as open squares. The number of mice in each treatment group was 4.

As shown in FIG. 11, intravenous administration of non-liposome formulated D-27mer peptide (SEQ ID NO:10) to mice resulted in a dose-dependent increase in [$^3$H]-cholesterol efflux as measured by an increase in plasma radioactivity (dpm). In these experiments, in vivo cholesterol export was determined in mice injected with J774 macrophages cholesterol-loaded with RBC membranes and [$^3$H]-cholesterol. Two hundred thousand macrophages in 100 µl PBS were injected into each mouse through the tail vein. At various time points thereafter, approximately 25 µl of blood were collected from the tail vein of each animal into heparinized capillary tubes. The tubes were then centrifuged for 5 minutes in an Adams Autocrit Centrifuge to separate red blood cells from plasma. Cholesterol efflux was determined by measuring the appearance of [$^3$H]-cholesterol in plasma by scintillation spectrometry. To study whether export of cholesterol from J774 cells to plasma was influenced by non-liposome formulated D-27mer peptide (SEQ ID NO:10), 24 hours after injection of [$^3$H]-cholesterol-loaded J774 macrophages into mice, the same animals received, by intravenous injection, 30 µg, 60 µg, 150 µg, 225 µg, 300 µg or 600 µg of D-27mer. All these amounts of D-peptides were dissolved in 100 µl of phosphate buffered saline and injected through the tail vein of each animal. As shown in FIG. 11, all doses of the non-liposome formulated D-27mer peptide (SEQ ID NO:10) including the lowest 30 µg/mouse dose, when administered intravenously to mice, increased [$^3$H]-cholesterol efflux as measured by an increase in plasma radioactivity (dpm) as compared to control mice.

A similar experiment was conducted in mice to compare the effects of non-liposome formulated D-27mer peptide (SEQ ID NO:10) to various L-form peptides, in particular non-liposome formulated, delipidated, full length murine SAA2.1 protein GFFSFVHEAFQGAGDMWRAYTDMKEANWKNSDKYFHARGNYDAAQRGPG-GVWAAEKISDG REAFQEFFGRGHEDTIADQEANRHGRSGKDPNYYRPPGLPDKY (SEQ ID NO:19), non-liposome formulated L-form amino acid peptide of the consensus sequence ADQAANEWGRSGKDPNHFR (SEQ ID NO:12), and non-liposome formulated L-form amino acid peptide containing amino acids 1-20 of human SAA1.1 or human SAA2.1 (RSFFSFLGEAFDGARDMWRA (SEQ ID NO:30)). All peptides were dissolved in 100 µl phosphate buffered saline and administered intravenously via tail vein injection. In these experiments, mice received either 15 µg/mouse of non-liposome formulated D-27mer peptide (SEQ ID NO:10), L-form amino acid peptide of the consensus sequence ADQAANEWGRSGKDPNHFR (SEQ ID NO:12), or L-form amino acid peptide containing amino acids 1-20 of human SAA1.1 or human SAA2.1 RSFFSFLGEAFDGARDMWRA (SEQ ID NO:30), or 75 µg/mouse non-liposome formulated, delipidated, full length murine SAA2.1 protein. Treatment with the non-liposome formulated D-27mer peptide caused an increase in cholesterol exported in the plasma while treatment with either of the non-liposome formulated L-form amino acid peptides ADQAANEWGRSGKDPNHFR (SEQ ID NO:12) or RSFFSFLGEAFDGARDMWRA (SEQ ID NO:30) had no effect on cholesterol efflux. Unexpectedly administration of non-liposome formulated, delipidated, full length murine SAA2.1 protein GFFSFVHEAFQGAGDMWRAYTDMKEANWKNSDKYFHARGNYDAAQRGPGGVWAAEKISDG REAFQEFFGRGHEDTIADQEANRHGRS-GKDPNYYRPPGLPDKY (SEQ ID NO:19) into the mice also resulted in an increase in radiolabeled cholesterol exported in the plasma which exceeded the increase observed following administration of the D-27mer peptide. See FIG. 15.

Figure 12:
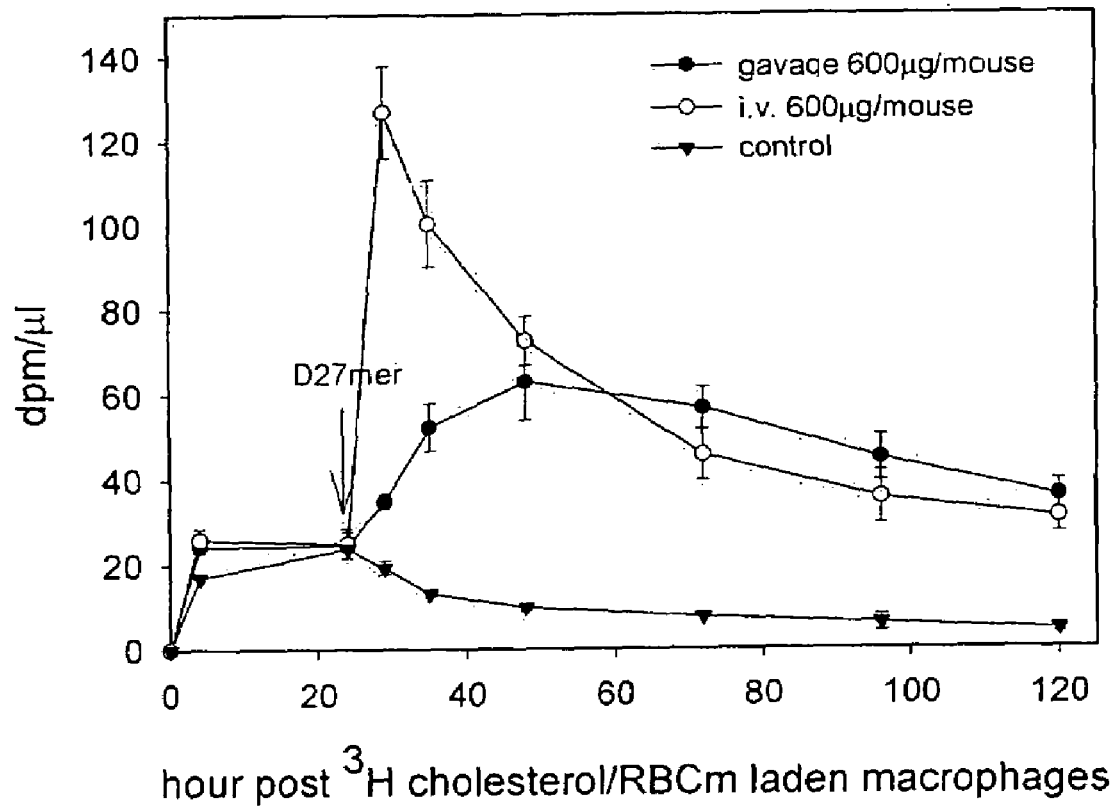
FIG. 12 is a line graph comparing the effects of oral versus intravenous injection of non-liposome formulated D-27mer peptide (SEQ ID NO:10) on cholesterol efflux in mice injected with J774 macrophages cholesterol-loaded with RBC membranes and [$^3$H]-cholesterol. Cholesterol efflux in mice administered 600 µg of the non-liposome formulated D-27mer peptide (SEQ ID NO:10) dissolved in phosphate buffered saline orally is depicted as filled circles. Cholesterol efflux in mice administered 600 µg of the D-27mer peptide (SEQ ID NO:10) dissolved in phosphate buffered saline intravenously is depicted as open circles. Cholesterol efflux in control mice administered phosphate buffered saline is depicted as closed triangles. The number of mice in each treatment group was 4.

In addition, as demonstrated in FIG. 12, oral administration of non-liposome formulated D-27mer peptide (SEQ ID NO:10) 24 hours after macrophage administration was also effective at increasing [$^3$H]-cholesterol efflux in these mice. In this experiment, mice were first injected with two hundred thousand J774 macrophages cholesterol-loaded with RBC membranes and [$^3$H]-cholesterol. Twenty-four hours after injection of the macrophages, the same animals received a dosage of 600 µg of non-liposome formulated D-27mer peptide (SEQ ID NO:10) dissolved in 500 µl of PBS by oral gavage. Oral gavage was carried out using a ball ended feeding needle. At various time points following oral gavage, approximately 25 µl of blood were collected from the tail vein of each animal and analyzed as described above. As shown in FIG. 12, administration of the non-liposome formulated D-27mer peptide (SEQ ID NO:10) orally at 600 µg resulted in a similar increase in cholesterol efflux as compared to mice receiving the same dose intravenously.

Figure 13:
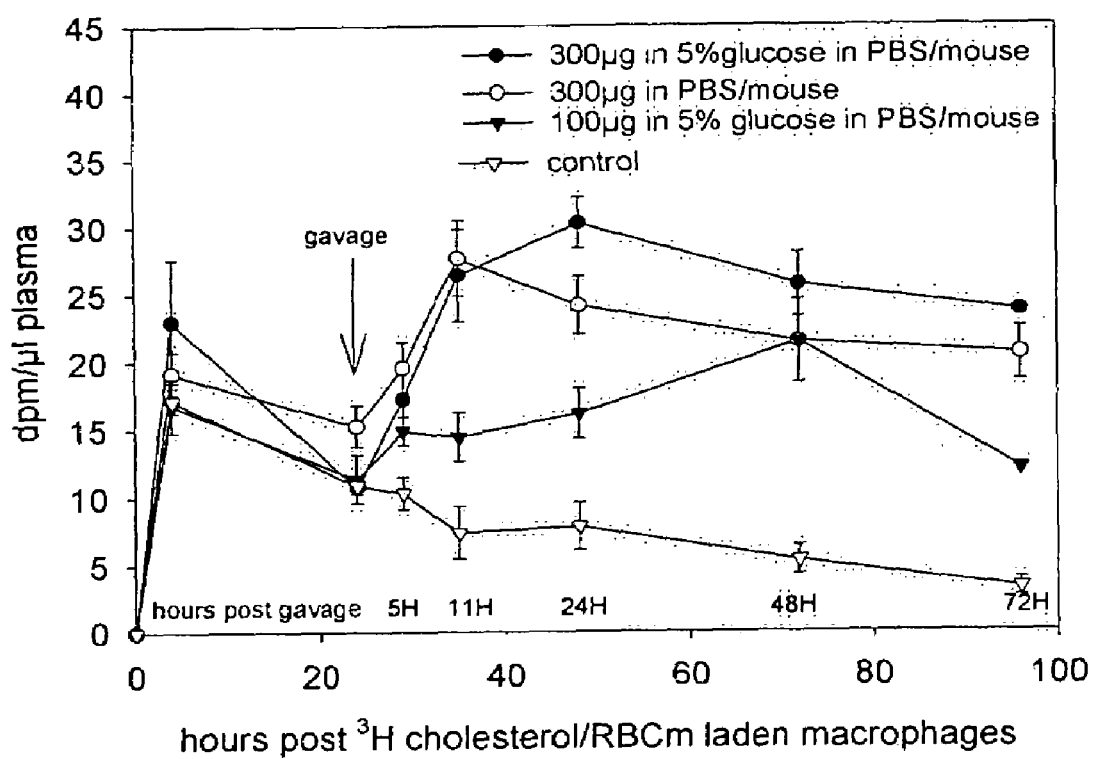
FIG. 13 is a line graph comparing cholesterol efflux in vivo in mice orally administered via gavage the non-liposome formulated D-27mer peptide (SEQ ID NO:10) dissolved in either phosphate buffered saline or phosphate buffered saline containing 5% weight/volume glucose. Animals administered peptide in phosphate buffered saline containing 5% weight/volume glucose also received drinking water containing 5% weight/volume glucose. Cholesterol efflux in mice administered 300 µg of the D-27mer peptide (SEQ ID NO:10) dissolved in 500 µl phosphate buffered saline is depicted as open circles. Cholesterol efflux in mice administered 300 µg of the D-27mer peptide (SEQ ID NO:10) dissolved in 500 µl phosphate buffered saline containing 5% glucose is depicted as closed circles. Cholesterol efflux in mice administered 100 µg of the D-27mer peptide (SEQ ID NO:10) dissolved in 500 µl phosphate buffered saline containing 5% glucose is depicted as closed triangles. Cholesterol efflux in control mice administered no peptide is depicted as open triangles. The number of mice in each treatment group was 4.
Figure 16:
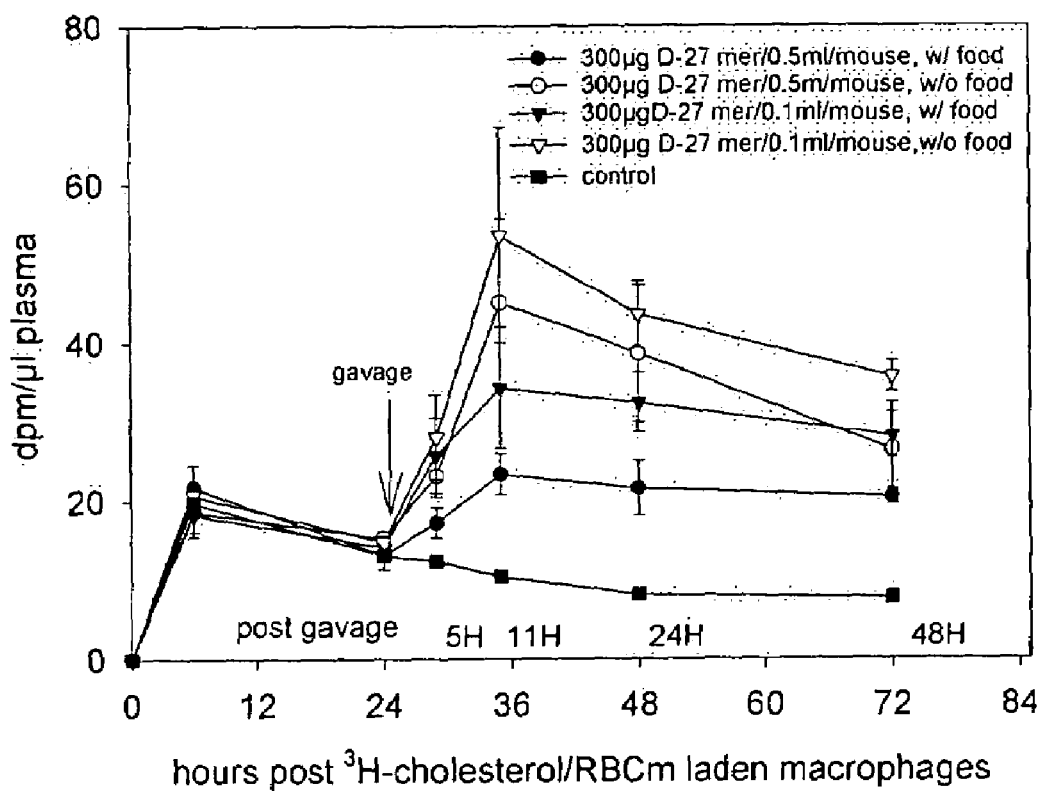
FIG. 16 is a line graph comparing the effects of fasting versus no fasting on cholesterol efflux in vivo in mice after treatment with non-liposome formulated D-27mer peptide (SEQ ID NO:10). Cholesterol efflux in mice administered the D-27mer peptide (SEQ ID NO:10) (300 µg/500 µl phosphate buffered saline) with food is depicted by filled circles. Cholesterol efflux in mice administered the D-27mer peptide (SEQ ID NO:10) (300 µg/500 µl phosphate buffered saline) without food is depicted by open circles. Cholesterol efflux in mice administered the D-27mer peptide (SEQ ID NO:10) (300 µg/100 µl phosphate buffered saline) with food is depicted by filled triangles. Cholesterol efflux in mice administered the D-27mer peptide (SEQ ID NO:10) (300 µg/100 µl phosphate buffered saline) without food is depicted by open triangles. Control animals are depicted by filled squares. The number of mice in each treatment group was 4.

Further, as shown in FIG. 13, the amount of cholesterol exported to the plasma at 24 hours was higher when non-liposome formulated D-27mer peptide (SEQ ID NO:10) was administered orally to mice in a pharmaceutically acceptable vehicle of phosphate buffered saline containing 5% weight/volume glucose as compared to administration of the same dose in phosphate buffered saline (Pappenheimer et al. Proc. Natl. Acad. Sci. USA 1994 91:1942-1945). Animals administered peptide in phosphate buffered saline containing 5% weight/volume glucose also received drinking water containing 5% weight/volume glucose. Efficacy of the non-liposome formulated D-27mer peptide (SEQ ID NO:10) was further enhanced upon oral administration to fasted animals as compared to animals receiving food. See FIG. 16. Also shown in FIG. 16 is that efficacy was enhanced when a smaller volume vehicle containing the same amount of peptide was administered to fasted as well as fed mice.

Figure 14:
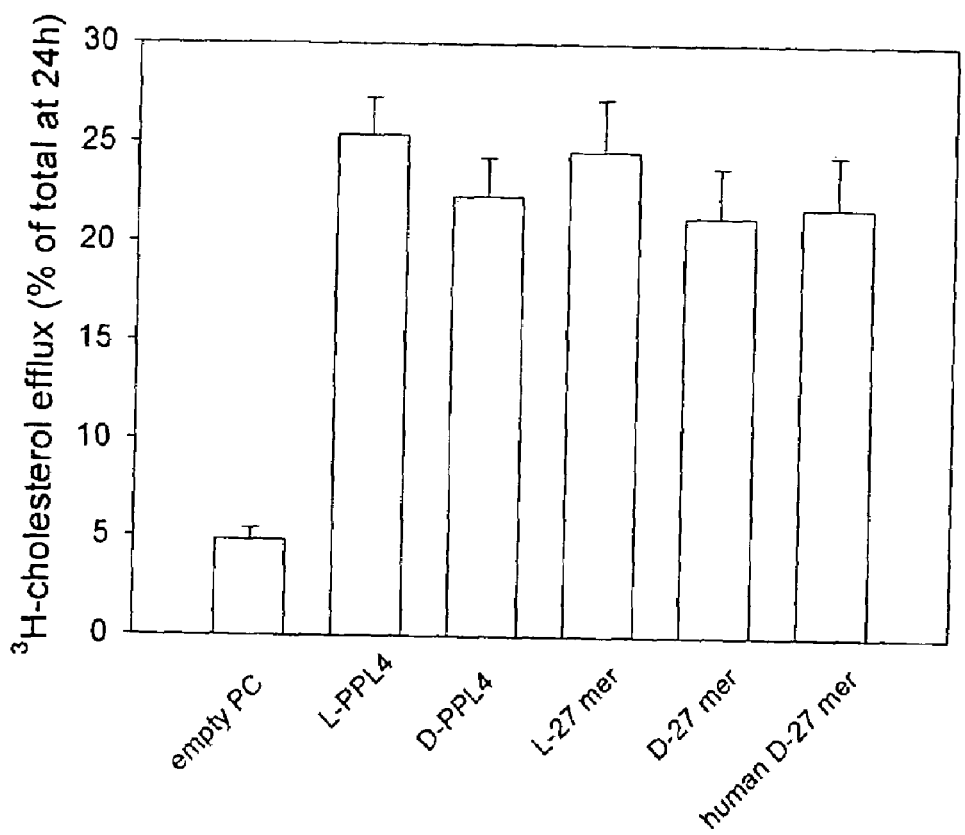
FIG. 14 is a bar graph comparing the effects of liposomes containing various synthetic peptides comprising either L- or D-form amino acids on cholesterol efflux in cholesterol-loaded human THP-1 cells. THP-1 cells were treated with empty PC (2-oleoyl-1-palmitoyl-sn-glycero-3-phosphocholine and cholesterol lipid mixture) liposomes or liposomes containing either the L-form amino acid peptide ADQAANEWGRSGKDPNHFR (SEQ ID NO:12), the D-form of this peptide (SEQ ID NO:32), the L-form amino acid peptide ADQEANRHGRSGKDPNYYRPPGLPAKY (SEQ ID NO:9), the D-form amino acid peptide ADQEANRHGRSGKDPNYYRPPGLPAKY (SEQ ID NO:10), or the D-form of the corresponding 27mer human peptide (SEQ ID NO:31). The final concentration of all peptides administered was 3.3 µM.
Figure 15:
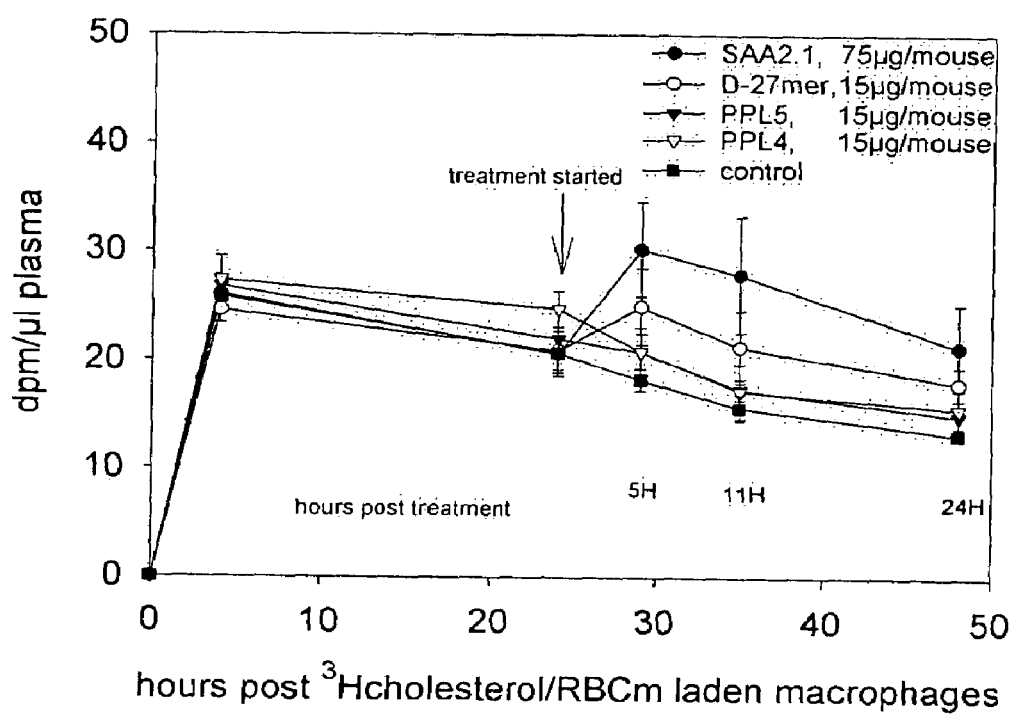
FIG. 15 is a line graph comparing in vivo cholesterol efflux in mice treated with non-liposome formulated, delipidated full length murine SAA2.1 protein GFFSFVHEAFQGAGDMWRAYTDMKEANWKNSDKYFHARGNYDAAQRGPGGVWAAEKISDG REAFQEFFGRGHEDTIADQEANRHGRSGKDPNYYRPPGLPDKY (SEQ ID NO:19), non-liposome formulated D-27mer peptide (SEQ ID NO:10), non-liposome formulated L-form amino acid peptide ADQAANEWGRSGKDPNHFR (SEQ ID NO:12) referred to in this figure as PPL4, or non-liposome formulated L-form amino acid peptide containing amino acids 1-20 of human SAA1.1 or human SAA2.1 RSFFSFLGEAFDGARDMWRA (SEQ ID NO:30) referred to in this figure as PPL5. All peptides were dissolved in 100 µl phosphate buffered saline and administered intravenously via tail vein injection. Cholesterol efflux in mice administered non-liposome formulated, delipidated full length murine SAA2.1 protein GFFSFVHEAFQGAGDMWRAYTDMKEANWKNSDKYFHARGNYDAAQRGPGGVWAAEKISDG REAFQEFFGRGHEDTIADQEANRHGRSGKDPNYYRPPGLPDKY (SEQ ID NO:19) (75 µg) is depicted by closed circles. Cholesterol efflux in mice administered non-liposome formulated D-27mer peptide (SEQ ID NO:10) (15 µg) is depicted by open circles. Cholesterol efflux in mice administered non-liposome formulated L-form amino acid peptide of the consensus sequence ADQAANEWGRSGKDPNHFR (SEQ ID NO:12) (15 µg) is depicted by open triangles. Cholesterol efflux in mice administered non-liposome formulated L-form amino acid peptide containing amino acids 1-20 of human SAA1.1 or human SAA2.1 RSFFSFLGEAFDGARDMWRA (SEQ ID NO:30) (15 µg) are depicted by closed triangles. Control animals, depicted by filled squares, received no treatment. The number of mice in each treatment group was 4.

As shown in FIG. 14, liposomal formulations of both the L-form and D-form of the consensus sequence ADQAANEWGRSGKDPNHFR (SEQ ID NO:12 and SEQ ID NO:32, respectively) and the peptide corresponding to residues 77-103 of murine SAA1.1 (SEQ ID NO:9 and SEQ ID NO:10, respectively) while all effective, showed similar cholesterol efflux activities in vitro in human TCP-1. Liposomes used in these experiments were prepared by the method of Jonas et al. ((J. Biol. Chem. 1989 264:4818-4825).

These experiments demonstrate that a synthetic D amino acid peptide of the present invention markedly increases in vivo cholesterol efflux both orally and intravenously. Further, this increase following oral and intravenous administration of the D-27mer (SEQ ID NO:10) lasted for at least 4 days. See FIG. 12.

Identification of the domain of SAA2.1 that is responsible for enhancing cholesterol ester hydrolase activity was performed in J774 cells preloaded with radio-labeled cholesteryl esters. These experiments were performed in the presence of Sandoz 58-035, an inhibitor of acyl CoA:cholesterol acyl transferase activity, to prevent re-esterification of liberated cholesterol and [$^{14}$C]oleate. Incubations proceeded for times ranging from 0 to 24 hours, following which the remaining quantities of [$^{14}$C]-labeled cholesteryl oleate in cells were measured to determine the rate of hydrolysis of cholesteryl ester. With re-esterification blocked, there were no significant differences in the rate of hydrolysis of [$^{14}$C]-labeled cholesteryl oleate in cells cultured in the presence of protein-free liposomes or liposomes containing 0.5 µM synthetic peptides corresponding to amino acid residues 1-20, 21-50 and 51-80 of murine SAA2.1, respectively. However, an equivalent amount of liposomes containing the synthetic peptide corresponding to amino acid residues 74-103 of murine SAA2.1 caused a 3-fold increase in cholesterol ester hydrolase activity in these cholesterol-laden murine cells.

The incorporation of [$^{14}$C]oleate into cholesteryl ester was used as a measure of acyl CoA:cholesterol acyl transferase activity to identify compositions inhibiting the enzyme activity. The relative acyl CoA:cholesterol acyl transferase activity was determined in cholesterol-laden murine cells that had been cultured in medium in the absence of liposomes or in the presence of protein-free liposomes or liposomes containing 0.5 μM synthetic peptides corresponding to amino acids 1-20, 21-50, 51-80 and 74-103 of murine SAA2.1. Following a 6 hour incubation, only the cells that had been exposed to liposomes containing synthetic peptides corresponding to amino acid residues 1-20 of murine SAA2.1 showed a two-fold decrease in acyl CoA:cholesterol acyl transferase activity, while other liposome treatments had no significant effect on the activity of this enzyme.

Cholesterol efflux from cholesterol-loaded J774 cells pre-incubated with liposomes containing one of the above synthetic peptides of murine SAA2.1 was also examined. In these experiments, cholesterol-loaded murine macrophages labeled with [$^3$H]cholesterol were pre-incubated for 4 hours with liposomes containing 0.5 μM synthetic peptides corresponding to amino acids 1-20, 21-50, 51-80 or 74-103 of murine SAA2.1. In some experiments, an equimolar combination of two synthetic peptides (0.5 μM each) corresponding to amino acid residues 1-20 and 74-103 of murine SAA2.1 was also assayed. Following incubation, the cells were washed extensively with DMEM/BSA to remove all radioactivity and liposomes in the pre-incubation medium. The chase efflux consisted of DMEM/BSA alone or medium containing HDL (50 μg/mL). At various time points, the efflux media were collected and analyzed for [$^3$H]cholesterol and free cholesterol mass. Results indicated that [$^3$H]cholesterol efflux to medium containing 0.2% BSA was 6.1±1.1% of total counts. Cells cultured in the presence of HDL (50 μg/mL), exported 31.2±2.2% of total cellular [$^3$H] sterol to the medium. Pre-incubation of cells with liposomes containing 0.5 μM synthetic peptides corresponding to amino acid residues 21-50 or 51-80 of murine SAA2.1 did not cause any significant changes in the rate of [$^3$H]cholesterol efflux into the medium containing the HDL. However, when cholesterol-laden J774 cells labeled with [$^3$H]cholesterol were pre-incubated with liposomes containing 0.5 μM synthetic peptides corresponding to amino acid residues 1-20 or 74-103 of murine SAA2.1, it was observed that 60.6±3.6% and 46.7±3.1% of total cellular [$^3$H]cholesterol were released into the medium when cells were subsequently cultured in the presence of HDL. Under similar culturing conditions, pre-incubation with the combination of these two synthetic peptides of SAA2.1 resulted in the export of 88.5±3.5% of total cellular [$^3$H]cholesterol to HDL. In addition, the initial rate of cholesterol efflux to HDL during the first 2 hours was twice as fast when compared to the results with liposomes containing either synthetic peptide alone.

Figure 10:
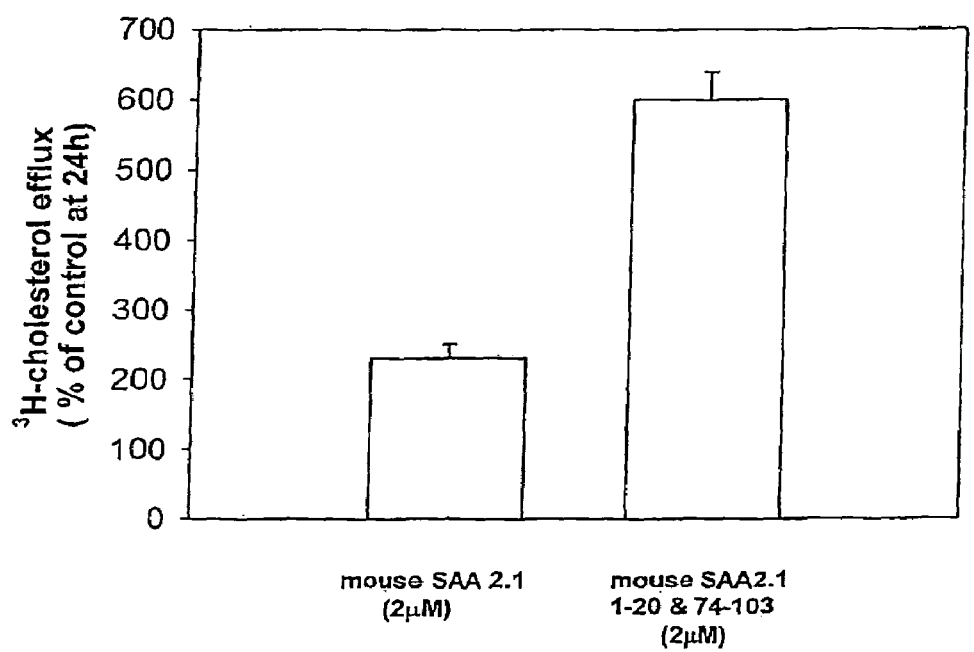
FIG. 10 is a bar graph comparing the effects of equimolar concentrations of liposomes containing full length murine SAA2.1 versus liposomes containing a peptide corresponding to amino acids 1-20 of murine SAA2.1 (SEQ ID NO:1) and amino acids 74-103 of murine SAA2.1 (SEQ ID NO:4) on cholesterol efflux in cholesterol-laden J774 cells.

Further, as shown in FIG. 10, comparison of cholesterol efflux by equimolar concentrations of liposomes containing the full length murine SAA2.1 protein and liposomes containing synthetic peptides corresponding to amino acid residues 1-20 or 74-103 of murine SAA2.1 showed a statistically significant greater cholesterol efflux from cholesterol-laden J744 cells receiving liposomes containing synthetic peptides corresponding to amino acid residues 1-20 or 74-103 of murine SAA2.1.

Figure 3A:
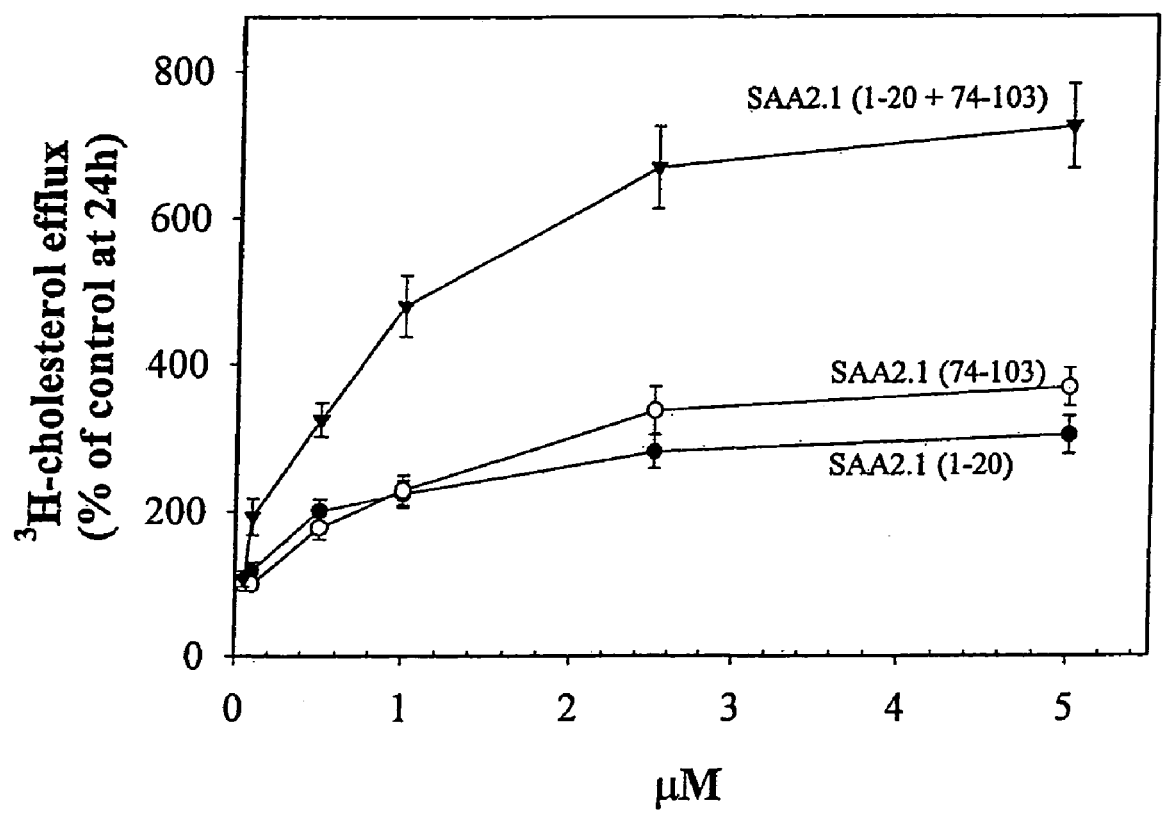
FIGS. 3A and 3B are line graphs depicting dose-response data of an in vitro cholesterol export study in macrophages administered liposomes containing a peptide corresponding to amino acids 1-20 of murine SAA2.1 (SEQ ID NO:1), liposomes containing a peptide corresponding to amino acids 74-103 of murine SAA2.1 (SEQ ID NO:4), or a combination of these peptides (SEQ ID NO:1+SEQ ID NO:4) as liposomes in a 1:1 ratio. Concentrations of peptides examined include 0.05, 0.1, 0.5, 1.0, 2.5 and 5.0 μM.
Figure 3B:
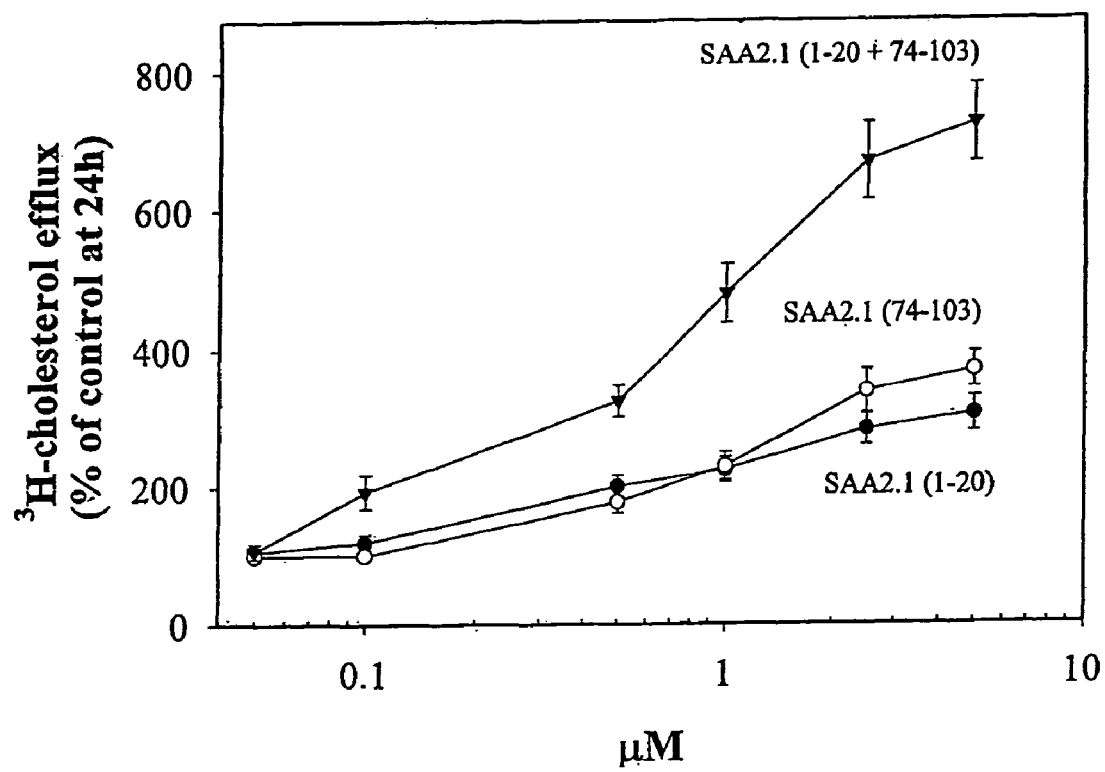

Dose-response curves of cholesterol export in cholesterol-laden murine macrophages were also generated for liposomes containing a peptide corresponding to amino acids 1-20 of murine SAA2.1 (SEQ ID NO:1), liposomes containing a peptide corresponding to amino acids 74-103 of murine SAA2.1 (SEQ ID NO:4) and liposomes containing a combination of these peptides (SEQ ID NO:1+SEQ ID NO:4) in a 1:1 molar ratio. Results are depicted in FIGS. 3A and 3B. Concentrations of peptides examined included 0.05, 0.1, 0.5, 1.0, 2.5 and 5.0 μM. Each of the peptides alone increased cholesterol efflux and the percent of cholesterol efflux as compared to controls increased with increasing amounts of each peptide alone. Further, as shown in FIGS. 3A and 3B, the combination of the two peptides produced a greater than additive effect. For example, as shown in FIGS. 3A and 3B, cholesterol efflux with 1 μM of the peptides alone was approximately 200% while cholesterol efflux with the combination of peptides at 1 μM was 500%.

Figure 4:
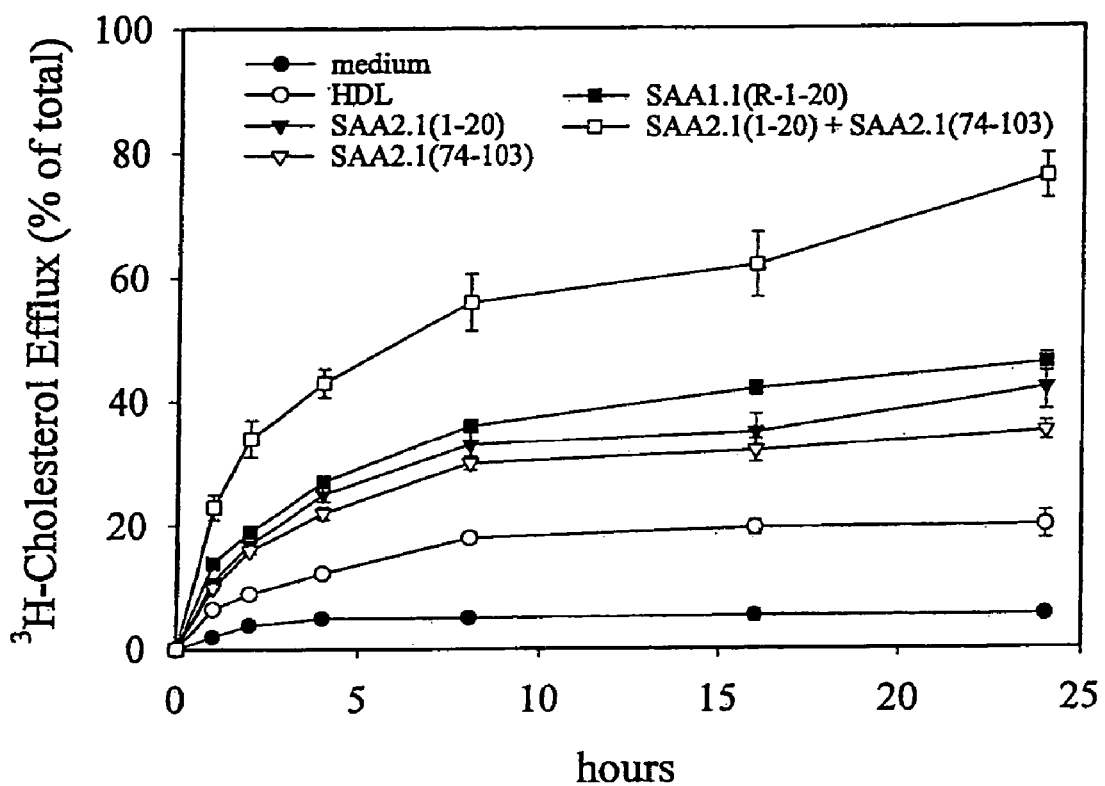
FIG. 4 is a line graph showing a time course of cholesterol efflux from cholesterol-laden human THP-1 cells exposed to liposomal formulations comprising various peptides of the present invention. Cholesterol efflux of these human cells following exposure to liposomes alone is depicted by filled circles. Cholesterol efflux of these human cells following exposure to HDL is depicted by open circles. Cholesterol efflux of these human cells following exposure to liposomes containing a peptide corresponding to amino acids 1-20 of murine SAA2.1 (SEQ ID NO:1) is depicted by filled triangles. Cholesterol efflux of these human cells following exposure to liposomes containing a peptide corresponding to amino acids 74-103 of murine SAA2.1 (SEQ ID NO:4) is depicted by open triangles. Cholesterol efflux of these human cells following exposure to liposomes containing a peptide corresponding to amino acids 1-20 of murine SAA2.1 plus an arginine at the N-terminus (SEQ ID NO:7) is depicted by filled squares. Cholesterol efflux of these human cells following exposure to liposomes containing a peptide corresponding to amino acids 1-20 of murine SAA2.1 (SEQ ID NO:1) and a peptide corresponding to amino acids 74-103 (SEQ ID NO:4) of murine SAA2.1 is depicted by open squares.

These peptides have also now been demonstrated to increase cholesterol efflux in human derived monocytic cells. These monocytes were differentiated into macrophages with phorbol myristate acetate (100 nM). In these experiments, cholesterol-laden human THP-1 cells were exposed to liposomal formulations comprising a peptide corresponding to amino acids 1-20 of murine SAA2.1 (SEQ ID NO:1), a peptide corresponding to amino acids 74-103 of murine SAA2.1 (SEQ ID NO:4), a peptide corresponding to amino acids 1-20 of murine SAA1.1 plus an arginine at the N-terminus (SEQ ID NO:7), or a peptide corresponding to amino acids 1-20 of murine SAA2.1 (SEQ ID NO:1) and a peptide corresponding to amino acids 74-103 (SEQ ID NO:4) of murine SAA2.1. Results from these experiments are depicted in FIG. 4. Unlike the peptide corresponding to amino acids 1-20 of murine 1.1 (SEQ ID NO:5), which is inactive, the liposomal formulation containing peptide corresponding to amino acids 1-20 of murine SAA2.1 plus an arginine at the N-terminus (SEQ ID NO:7) effectively increased cholesterol efflux in these human cells equal to, if not better than, peptides corresponding to amino acids 1-20 of murine SAA2.1 (SEQ ID NO:1) and amino acids 74-103 of murine SAA2.1 (SEQ ID NO:4).

Thus, the rate of cholesterol export may increase with different peptides and/or with increasing concentrations of a peptide.

Figure 5A:
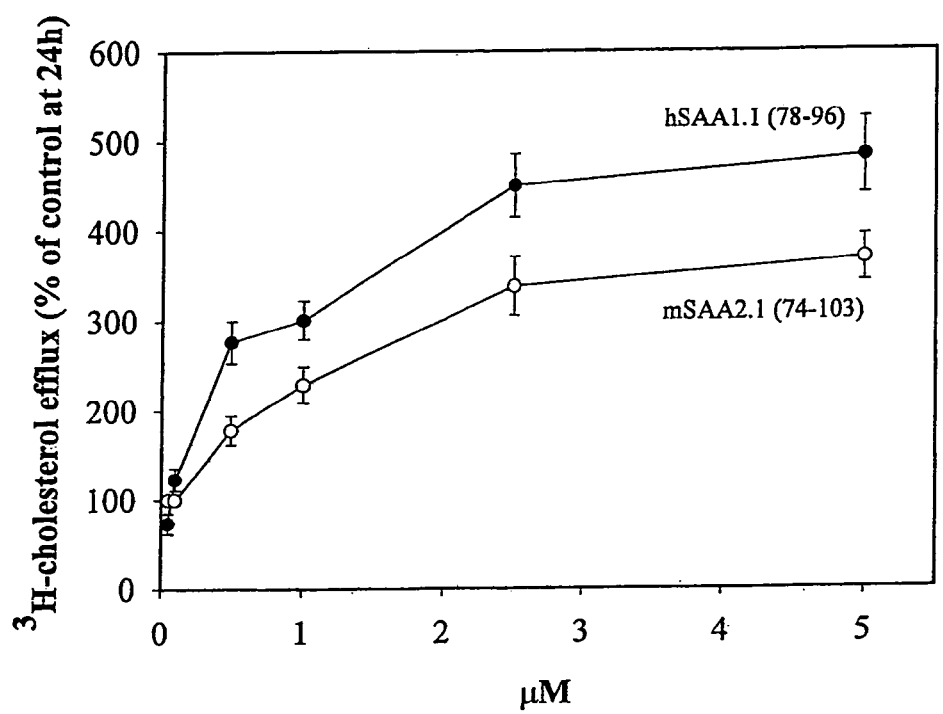
FIGS. 5A and 5B are line graphs depicting dose-response data of an in vitro cholesterol export study in macrophages administered liposomes containing a peptide corresponding to amino acids 78-96 of human SAA1.1 (SEQ ID NO:12) and liposomes containing a peptide corresponding to amino acids 74-103 of murine SAA2.1 (SEQ ID NO:4). Concentrations of peptides examined include 0.05, 0.1, 0.5, 1.0, 2.5 and 5.0 µM.
Figure 5B:
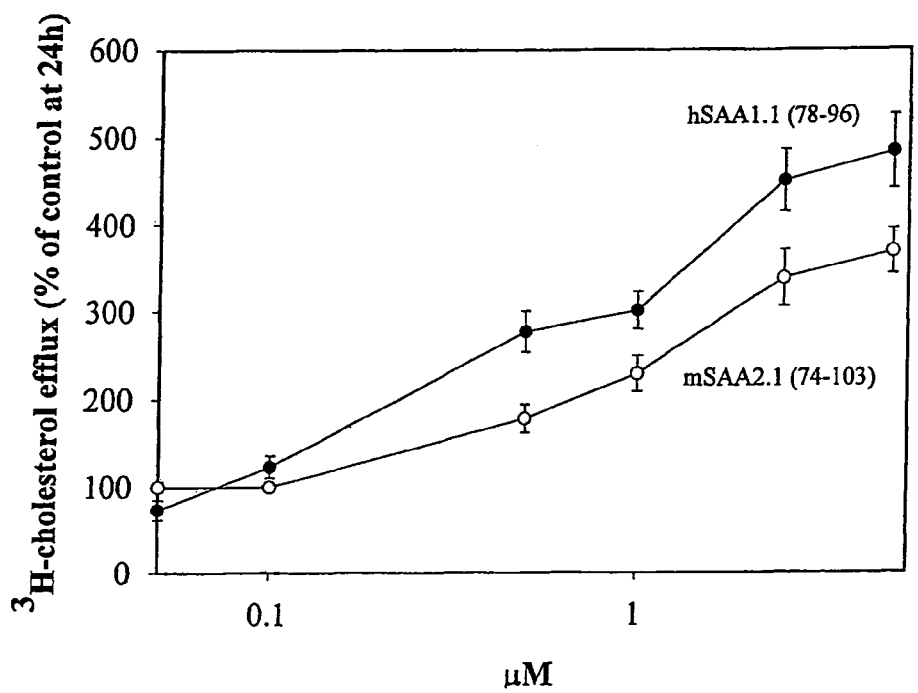

Similar studies were performed with the peptide corresponding to residues 78-96 of human SAA1.1 (ADQAANEWGRSGKDPNHFR; SEQ ID NO:12). FIGS. 5A and 5B show dose response curves from an in vitro cholesterol export study in macrophages administered liposomes containing a peptide corresponding to amino acids 78-96 of human SAA1.1 (SEQ ID NO:12) or liposomes containing a peptide corresponding to amino acids 74-103 of murine SAA2.1 (SEQ ID NO:4). Concentrations of peptides examined were 0.05, 0.1, 0.5, 1.0, 2.5 and 5.0 μM. As shown by FIGS. 5A and 5B, the human SAA1.1 peptide (SEQ ID NO:12) was at least as effective if not more effective at increasing cholesterol efflux in response to increased dose than the mouse peptide. Accordingly, these results are indicative of human SAA1.1 peptides comprising SEQ ID NO:12 being enhancers of cholesterol ester hydrolase activity.

Figure 9:
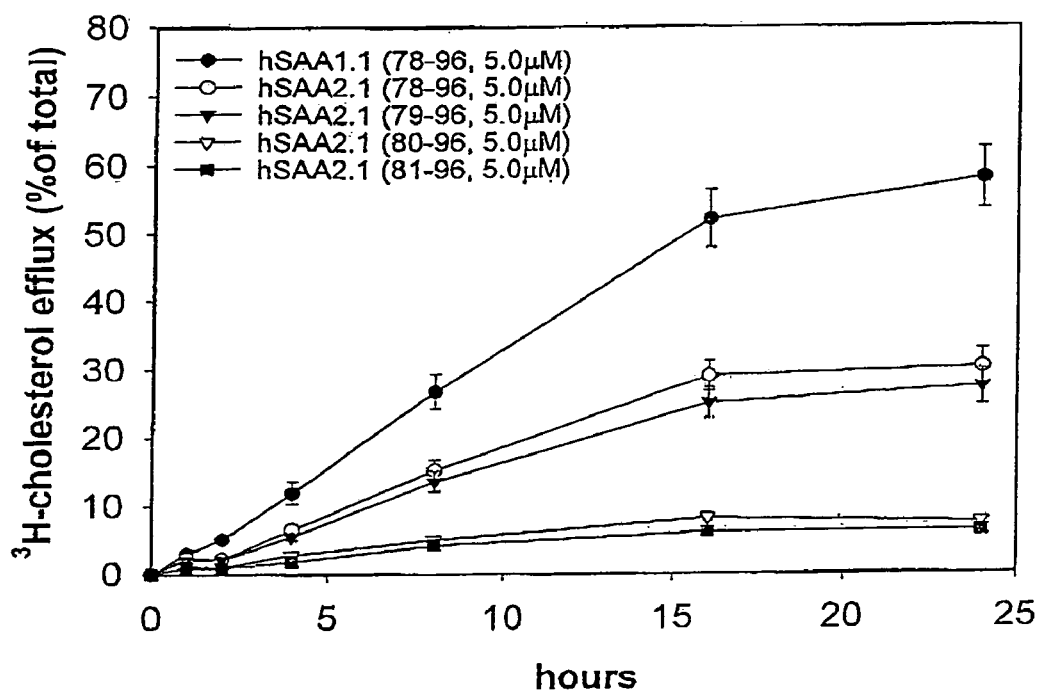
FIG. 9 is a line graph showing a time course study of in vitro cholesterol efflux in mouse J774 cells in the presence of liposomal formulations of various cholesterol ester hydrolase-enhancing peptides of the present invention. Cholesterol efflux of cells in the presence of a liposomal formulation containing human SAA1.1$_{78-96}$ (SEQ ID NO:12) is depicted as filled circles. Cholesterol efflux of cells in the presence of a liposomal formulation containing human SAA2.1$_{78-96}$ (SEQ ID NO:11) is depicted as open circles. Cholesterol efflux of cells in the presence of a liposomal formulation containing human SAA2.1$_{79-96}$ (SEQ ID NO:26) is depicted as filled triangles. Cholesterol efflux of cells in the presence of a liposomal formulation containing human SAA2.1$_{80-96}$ (SEQ ID NO:27) is depicted as open triangles. Cholesterol efflux of cells in the presence of a liposomal formulation containing human SAA2.1$_{81-96}$ (SEQ ID NO:28) is depicted as filled squares.

FIG. 9 shows a time course study of cholesterol efflux in mouse 774 cells with liposomal formulations containing human SAA1.1$_{78-96}$ (SEQ ID NO:12), human SAA2.1$_{78-96}$ (SEQ ID NO:11), human SAA2.1$_{79-96}$ (SEQ ID NO:26), human SAA2.1$_{80-96}$ (SEQ ID NO:27) or human SAA2.1$_{81-96}$ (SEQ ID NO:28). As shown therein, the liposomal formulation containing human SAA1.1$_{78-96}$ (SEQ ID NO:12) exhibited the greatest cholesterol export enhancing activity of the formulations examined. Liposomal formulations containing human SAA2.1$_{78-96}$ (SEQ ID NO:11) or human SAA2.1$_{79-96}$ (SEQ ID NO:26) also exhibited cholesterol export enhancing activity with each having an activity of about half of the human SAA1.1$_{78-96}$ containing liposomal formulation. Liposomal formulations containing human SAA2.1$_{80-96}$ (SEQ ID NO:27) or human SAA2.1$_{81-96}$ (SEQ ID NO:28) exhibited little to no cholesterol export enhancing activity thus indicating the presence of at least residue 79 to be important to the activity of these peptides.

Figure 6:
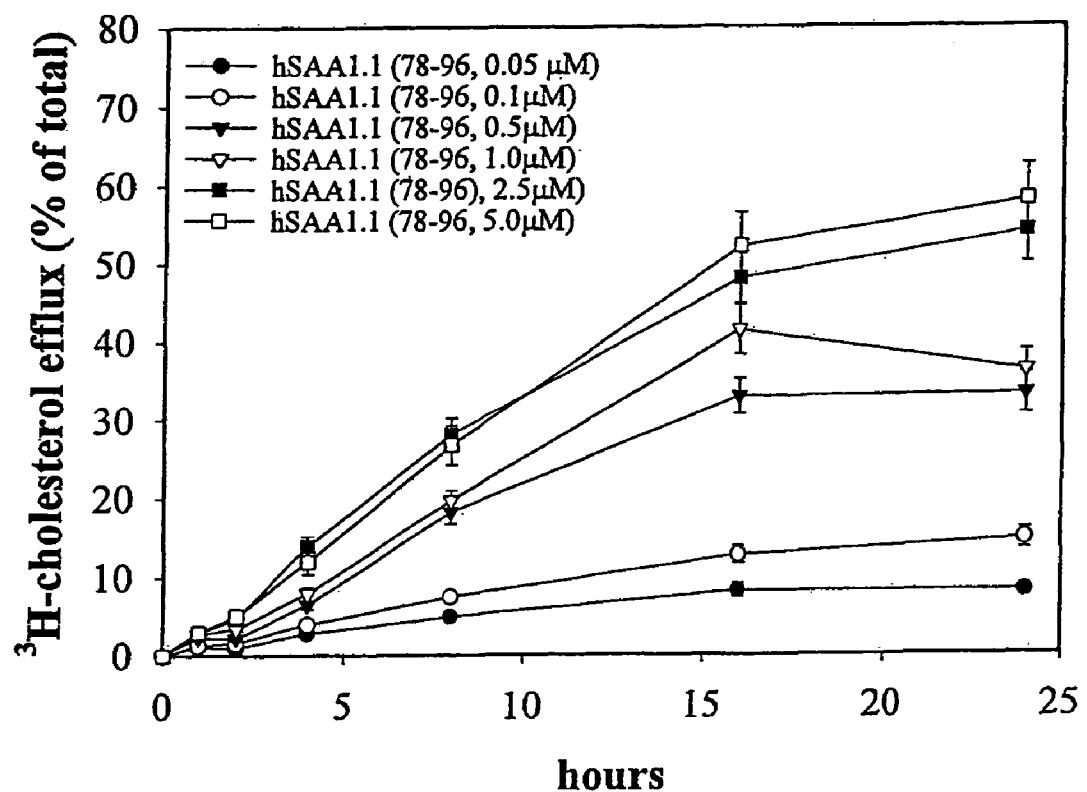
FIG. 6 is a line graph showing a time course of cholesterol efflux from cholesterol-laden human THP-1 cells exposed to liposomal formulations comprising various concentrations of the peptide of residues 78-96 of human SAA1.1. Cholesterol efflux of these human cells following exposure to liposomes containing 0.05 µM hSAA1.1$_{78-96}$ is depicted as filled circles. Cholesterol efflux of these human cells following exposure to liposomes containing 0.05 µM hSAA1.1$_{78-96}$ is depicted by filled circles. Cholesterol efflux of these human cells following exposure to liposomes containing 0.1 µM hSAA1.1$_{78-96}$ is depicted by open circles. Cholesterol efflux of these human cells following exposure to liposomes containing 0.5 µM hSAA1.1$_{78-96}$ is depicted by filled triangles. Cholesterol efflux of these human cells following exposure to liposomes containing 1.0 µM hSAA1.1$_{78-96}$ is depicted by open triangles. Cholesterol efflux of these human cells following exposure to liposomes containing 2.5 µM hSAA1.1$_{78-96}$ is depicted by filled squares. Cholesterol efflux of these human cells following exposure to liposomes containing 5.0 µM hSAA1.1$_{78-96}$ is depicted by open squares.

A time course of cholesterol efflux was also performed in cholesterol-laden human THP-1 cells exposed to liposomal formulations comprising various concentrations of a peptide corresponding to residues 78-96 of human SAA1.1. Results from this experiment are depicted in FIG. 6. As shown therein, cholesterol efflux from macrophages continued to increase over a time period from 0 to 24 hours for all concentrations of peptide examined.

Additional in vivo studies have also been conducted wherein mice were first injected intravenously with [$^3$H]cholesterol-laden macrophages and then injected 24 hours later with liposomes containing 0.5 µM of synthetic peptides corresponding to amino acid residues 1-20, 21-50, 51-80 or 74-103 of murine SAA2.1. Results from this study are depicted in FIG. 1. At time points indicated in the graph of FIG. 1, approximately 25 µl of blood were collected from the tail vein of each animal. The blood samples were centrifuged to separate the red blood cells from the plasma and the [$^3$H]-cholesterol in plasma was determined by scintillation counting. Results are mean±SEM of four determinations. As shown in this Figure, intravenous injection of liposomes containing either SAA2.1 peptide residues 1-20 (acyl CoA:cholesterol acyl transferase-inhibiting domain), or residues 74-103 (cholesterol hydrolase ester-enhancing domain) dramatically increased [$^3$H]-cholesterol efflux as measured by an increase in plasma radioactivity (dpm). In the same study, the human acyl CoA:cholesterol acyl transferase-inhibiting SAA1.1 peptide domain, which is equivalent to the human and mouse SAA2.1 domain, also promoted in vivo cholesterol export.

Figure 19:
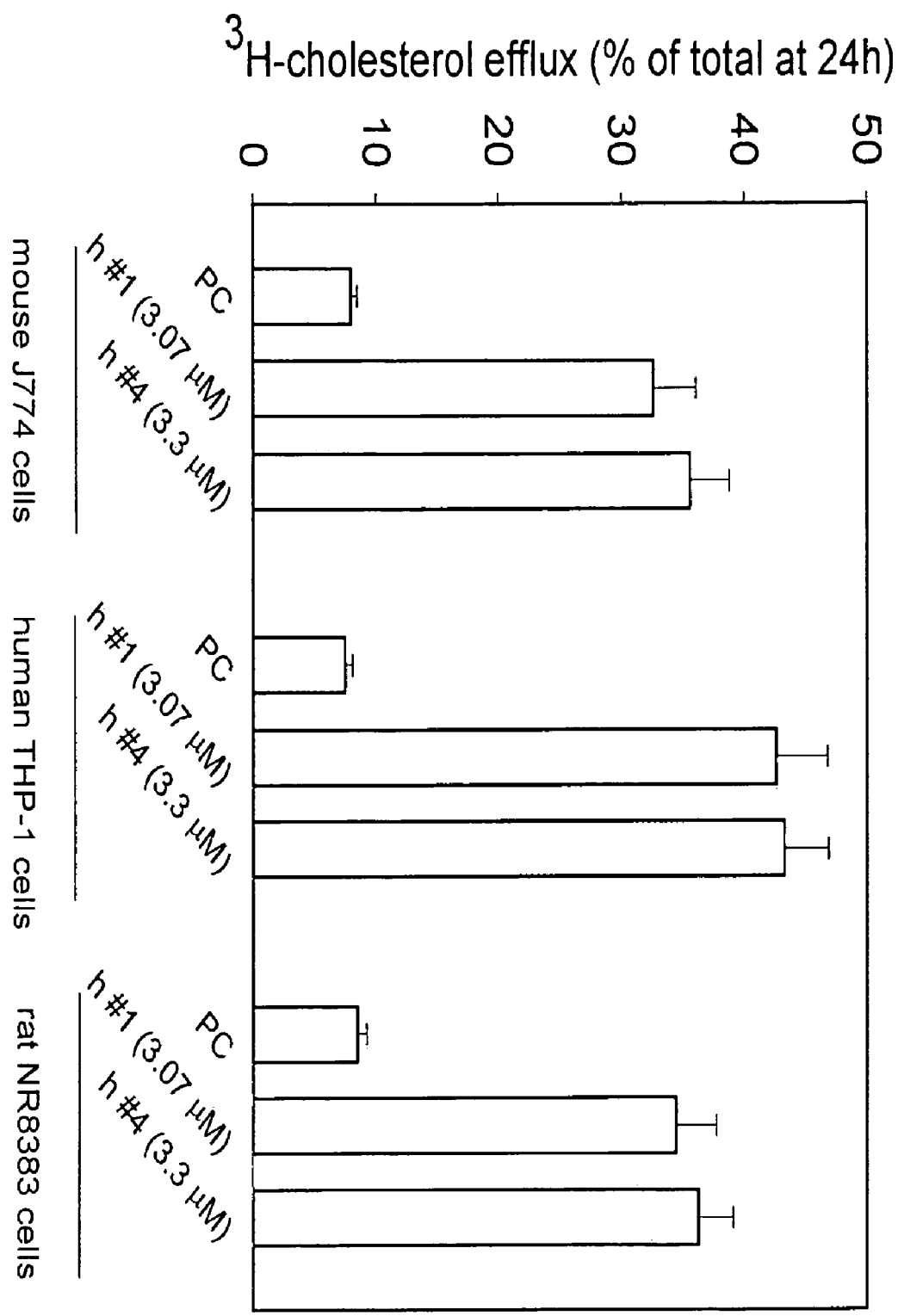
FIG. 19 is a bar graph comparing the cross species efficacy of peptide ADQAANEWGRSGKDPNHFR (SEQ ID NO:12) and the peptide RSFFSFLGEAFDGARDMWRA (SEQ ID NO:30) in mouse J744 cells, human THP-1 cells and rat NR8383 cells. In this figure, h#1 corresponds to the peptide RSFFSFLGEAFDGARDMWRA (SEQ ID NO:30) and h#4 corresponds to the peptide ADQAANEWGRSGKDPNHFR (SEQ ID NO:12).

FIG. 19 shows cross species efficacy of the L-form consensus sequence peptide ADQAANEWGRSGKDPNHFR (SEQ ID NO:12) and the L-form amino acid peptide RSFFSFLGEAFDGARDMWRA (SEQ ID NO:30) containing amino acids 1-20 of human SAA1.1 or human SAA2.1 at increasing macrophage cholesterol export was demonstrated in mouse, human and rat cells. In these experiments, mouse J774 cells, human THP-1 cells and rat NR8383 cells were loaded with red blood cell membranes containing $^3$H-cholesterol in accordance with procedures outlined in Example 4. The peptides were prepared as lipid mixtures using a microfluidizer procedure. Briefly, 3 mg of the 20-mer synthetic peptide (SEQ ID NO:30) or the 19-mer synthetic peptide (SEQ ID NO:12) were mixed with 5 ml cyclohexane and sonicated (output power of 14 watts) for 20-seconds followed by a 10-second interval. Separately, 2-oleoyl-1-palmitoyl-sn-glycero-3-phosphocholine (Sigma-Aldrich P3017; 67.8 mg) and cholesterol (9.66 mg) were dissolved in 2 ml of chloroform, vortexed and transferred to a 500 ml round bottom flask. The two mixtures (i.e. cyclohexane/peptide and phosphatidylcholine/cholesterol solutions) were then combined. The combined solution was dried using nitrogen gas while swirling the flask, resulting in a thin layer of lipid at the bottom half of the flask. In order to ensure that the thin layer of lipid residue was completely dry, nitrogen gas was streamed over the lipid layer for an additional 10 minutes. The dried lipid layer which contains the 20-mer peptide (SEQ ID NO: 30) or 19-mer peptide (SEQ ID NO:12) was rehydrated and mixed with 20 ml phosphate buffered saline on a shaking platform or incubator (250 rpm) overnight at room temperature. The rehydrated lipid mixture was then passed five times through a microfluidizer (e.g. Model-110S, Microfluidics Corp.). The microfluidizer was fitted with a F20Y reaction chamber and the operating pressure was 15,000 psi. Mouse, human and rat macrophages were then treated in accordance with procedures set forth in Examples 10 and 14 with either the h#1 or h#4 peptide/lipid solution for 24 hours. h#1 corresponds to the 20-mer peptide SEQ ID NO:30 and h#4 corresponds to the 19-mer peptide SEQ ID NO:12. Efficacy of the peptides was determined as the amount $^3$H-cholesterol exported into the media after 24 hours. Results from this experiment are depicted in FIG. 19. As shown therein both peptides were equally effective in inducing cholesterol export from mouse, human and rat macrophages. PC represents the empty liposome treated group. A similar base line cholesterol export profile was seen regardless of cell type.

Figure 17:
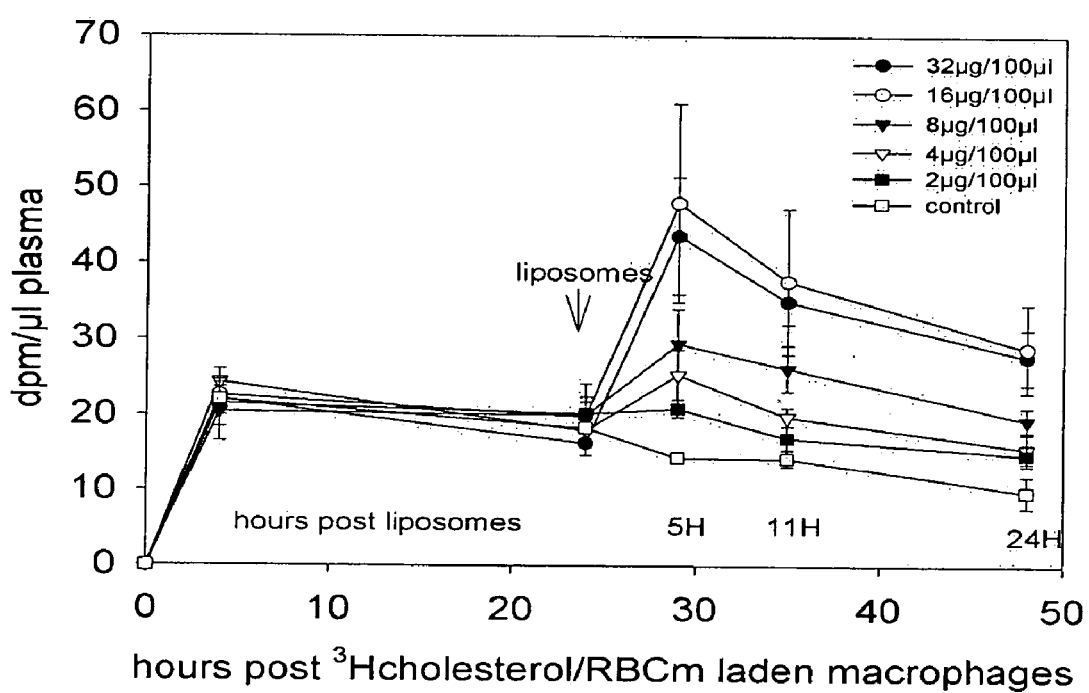
FIG. 17 is a line graph depicting dose-response data of an in vivo cholesterol export study in mice administered liposomes containing a peptide corresponding to amino acids 78-96 of human SAA1.1 (SEQ ID NO:12). Concentrations of peptides examined include 2, 4, 8, 16 and 32 µg/100 µl. Mice were administered the composition intravenously via tail vein injection. The number of mice in each treatment group was 4.
Figure 18:
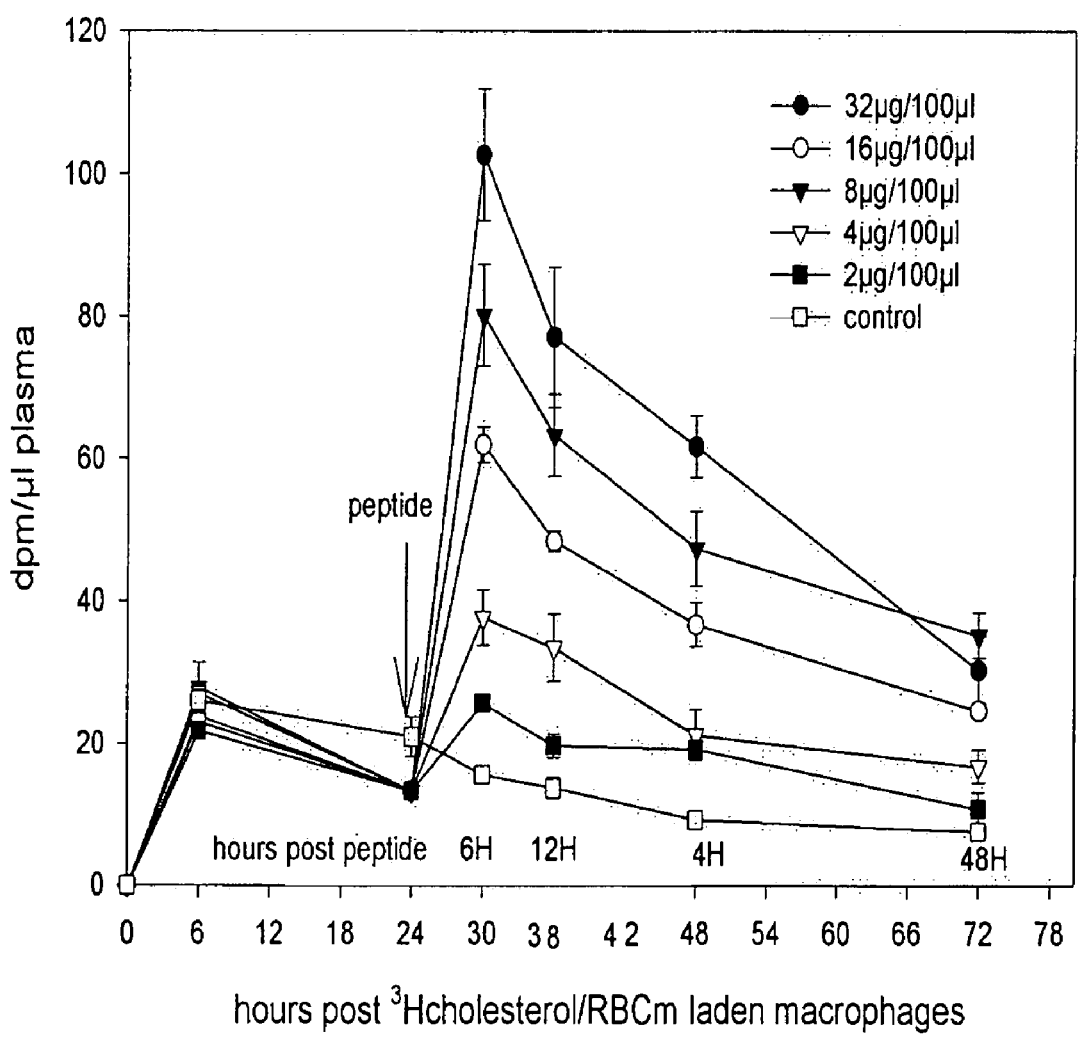
FIG. 18 is a line graph depicting dose-response data of an in vivo cholesterol export study in mice administered liposomes containing a peptide corresponding to amino acids 1-20 of human SAA1.1 (SEQ ID NO:30). Concentrations of peptides examined include 2, 4, 8, 16 and 32 μg/100 μl. Mice were administered the composition intravenously via tail vein injection. The number of mice in each treatment group was 4.

In vivo dose response curves were also determined for liposome formulated L-form consensus sequence peptide ADQAANEWGRSGKDPNHFR (SEQ ID NO:12) and the L-form amino acid peptide RSFFSFLGEAFDGARDMWRA (SEQ ID NO:30) containing amino acids 1-20 of human SAA1.1 or human SAA2.1 in mobilizing cholesterol export from macrophages in mice (See FIGS. 17 and 18, respectively). These in vivo studies were conducted similarly to procedures set forth in Examples 4 and 10. Briefly, mouse J774 cells were loaded with red blood cell membranes which had been equilibrated with $^3$H-cholesterol. Cells were then injected into mice via the tail vein, and 24 hours later were treated with various doses of either the liposome formulated L-form consensus sequence peptide ADQAANEWGRSGKDPNHFR (SEQ ID NO:12) or the liposome formulated L-form amino acid peptide RSFFSFLGEAFDGARDMWRA (SEQ ID NO:30) containing amino acids 1-20 of human SAA1.1 or human SAA2.1. Mice administered the peptide of SEQ ID NO:12 or SEQ ID NO:30 received either 2, 4, 8, 16 or 32 µg/100 µl per mouse. $^3$H-Cholesterol export into the plasma was measured by counting the radioactivity (dpm) over the indicated times of 6, 12, 24 and 48 hours, post peptide injection. Peptides were liposome formulated in accordance with procedures described in Example 6. As shown in FIGS. 17 and 18 both the liposome formulated L-form consensus sequence peptide ADQAANEWGRSGKDPNHFR (SEQ ID NO:12) and the liposome formulated L-form amino acid peptide RSFFSFLGEAFDGARDMWRA (SEQ ID NO:30) containing amino acids 1-20 of human SAA1.1 or human SAA2.1 demonstrated increased efficacy as the dose increased. These data demonstrate that the human peptides are also effective in inducing an increase in cholesterol export in vivo in the mouse.

The experiments set forth herein demonstrate that liposomes containing native SAA2.1 protein, or synthetic peptides comprising the murine acyl CoA:cholesterol acyl transferase-inhibiting domain or the murine or human cholesterol ester hydrolase enhancing domain, markedly increased in vivo cholesterol efflux. Further, this increase lasted for over 4 days. Additionally, the human acyl CoA:cholesterol acyl transferase-inhibiting SAA peptide domain also promoted in vivo cholesterol efflux. Thus, these data are demonstrative of the key role SAA, and in particular the acyl CoA:cholesterol acyl transferase-inhibiting domain and the cholesterol hydrolase ester-enhancing domain of this protein, play in facilitating cholesterol removal from cholesterol-laden macrophages located in atherosclerotic plaques. The data substantiate the utility of designing and using peptides or mimetics of these domains to reduce or prevent atherogenesis and/or cause regression of an atherosclerotic plaque by increasing the efflux of cholesterol from macrophages located in an atherosclerotic lesion. Such peptides or mimetics thereof will be useful in the treatment or prevention of atherosclerosis and in the treatment of coronary heart disease and cardiovascular disease associated with atherosclerosis.

The export process of cholesterol is coupled to the ATP binding cassette transporter (ABCA1) pathway. Lipid efflux to apolipoproteins has been shown previously to be stimulated by treatment of murine macrophages with cAMP analogues (Lin et al. 2002 Biochem Biophys Res. Commun. 290:663-669; Oram et al. 2000 J. Biol. Chem 275:34508-34511). Also, the expression of ABCA1 is induced by cAMP treatment (Lin et al. 2002 Biochem Biophys Res. Commun. 290:663-669; Oram et al. 2000 J. Biol. Chem 275:34508-34511). The inventors herein examined the effect of 8-bromo-cAMP (0.3 mM) on cholesterol efflux by liposomes containing various apolipoproteins when incubated with cholesterol-laden J774 macrophages. Such cells were pre-labeled with [$^3$H]-cholesterol in the presence of Sandoz 58-035, an ACAT inhibitor, to ensure that all of the radiolabeled cholesterol released from the cells was derived from the un-esterified cholesterol pool, and the cells were treated for 12 hours with 8-bromo-cAMP. This was followed by incubation with various acceptors. The fractional release of cellular labeled cholesterol was determined as a function of time. When compared to untreated cells, cAMP pre-treatment resulted in a 62.1% and 32.7% increase in the initial rate of cholesterol efflux to liposomes containing SAA2.1 and apoA-1. No stimulation of efflux was observed when cells were exposed to SAA1.1 liposomes with or without cAMP pre-treatment. Furthermore, it has been demonstrated previously that SAA1.1 liposomes are not any more effective than protein-free liposomes in promoting cholesterol efflux from cholesterol-laden macrophages (Tam et al. 2002 J. Lipid Res. 43:1410-1420). Moreover, cAMP treatment did not stimulate cholesterol export to culture medium containing no liposomes.

To investigate whether an apolipoprotein free cholesterol acceptor such as cyclodextrin has the ability to catalyze the removal of cholesterol from macrophages, cholesterol-loaded and labeled J774 cells were incubated with liposomes and methyl-β-cyclodextrin (0.1 mM) (CD). No stimulation of cholesterol efflux to medium containing no liposomes was observed at this concentration of CD. In contrast, CD treatment resulted in a 4-fold increase in the initial rate of cholesterol efflux in cells treated with liposomes containing SAA2.1, but not liposomes containing SAA1.1, nor protein-free liposomes. Furthermore, cAMP pre-treatment caused a further increase (45.5%) in cholesterol efflux in cells exposed to liposomes containing SAA2.1 and CD.

Thus, the present invention provides isolated peptides, Y-Z and Q-Y-Z compounds and mimetics of these, and pharmaceutical compositions comprising an isolated peptide or portion thereof, a Y-Z or Q-Y-Z compound or a mimetic of these, for use in the prevention and/or treatment of atherosclerosis as well as coronary heart disease and cardiovascular disease associated with atherosclerosis. In a preferred embodiment, peptides or mimetics thereof of the present invention contain one or more D amino acids. Pharmaceutical compositions of the present invention comprise a peptide or portion thereof, a Y-Z or Q-Y-Z compound, or a mimetic of these, of the cholesterol ester hydrolase enhancing domain of SAA2.1; and/or a peptide or portion thereof, a Y-Z or Q-Y-Z compound, or a mimetic of these, of the acyl CoA:cholesterol acyl transferase inhibitory domain of SAA2.1. Thus, preferred compositions of the present invention comprise a peptide containing amino acids 77-95 of mouse SAA2.1 or 78-96 of human SAA1.1 or a portion thereof, and/or a peptide containing residues 1-16 of SAA2.1 or a portion thereof, or a mimetic of either or both of these peptides or portions thereof. Particularly preferred are compositions comprising a peptide containing amino acids 77-95 of mouse SAA2.1 or a portion thereof and comprising one or more D amino acids or a peptide containing amino acids 78-96 of human SAA1.1 or a portion thereof and comprising one or more D amino acids.

By "portion thereof" it is meant to be inclusive of peptides exhibiting similar biological activities to the isolated peptides described herein but which, (1) comprise shorter fragments of the 19 residue cholesterol ester hydrolase enhancing domain or the 16 or 23 residue acyl CoA:cholesterol acyl transferase inhibitory domain of murine SAA2.1, or human SAA1.1 or SAA2.1, respectively or (2) overlap with only part of the 19 residue cholesterol enhancing domain or the 16 or 23 residue acyl CoA:cholesterol acyl transferase inhibitory domain of murine SAA2.1, or human SAA1.1 or SAA2.1, respectively. For example, it is believed that peptides comprising the portion of the acyl CoA:cholesterol acyl transferase inhibitory domain of murine SAA2.1 extending from residues about 1 to 12, 1 to 13, or 1 to 14 will also inhibit acyl CoA:cholesterol acyl transferase similarly to the synthetic peptides of residues 1-20 of murine SAA2.1. Similarly, as shown herein, portions of residues 1-23 of human SAA1.1 and SAA2.1, e.g. the 1-20 mer (SEQ ID NO:30), are effective at inhibiting acyl CoA:cholesterol acyl transferase. A preferred portion of the 30 amino acid sequence of residues 74-103 of murine SAA2.1 with cholesterol ester hydrolase enhancing activity has also been identified and comprises a 19 amino acid region corresponding to residues 77 through 95 of this domain. Similarly, 18 to 19 amino acid regions corresponding to residues 79 through 96 or 78 through 96, respectively, of human SAA1.1 have been identified and demonstrated to have cholesterol ester enhancing properties. Shorter portions of these 77-95, 78-96 or 79-96 residue peptides with similar biological activities can be identified in the same manner as these 77-95, 78-96 or 79-96 residue peptides. Accordingly, the present invention relates to portions of the peptides taught herein as well.

A preferred peptide of the present invention is the synthetic peptide corresponding to amino acid residues 1-20 of murine SAA1.1 protein sequence plus an arginine at the N-terminus (RGFFSFIGEAFQGAGDMWRAY; SEQ ID NO:7).

By synthetic, as used herein it is meant that the peptide is prepared synthetically either by chemical means or recombinantly.

Further, it will of course be understood, without the intention of being limited thereby, that a variety of substitutions of amino acids in the disclosed peptides is possible while preserving the structure responsible for the cholesterol ester hydrolase enhancing activity or the acyl CoA:cholesterol acyl transferase inhibitory activity of the peptides disclosed herein. Conservative substitutions are described in the patent literature, as for example, in U.S. Pat. No. 5,264,558. It is thus expected, for example, that interchange among non-polar aliphatic neutral amino acids, glycine, alanine, proline, valine and isoleucine, would be possible. Likewise, substitutions among the polar aliphatic neutral amino acids, serine, threonine, methionine, asparagine and glutamine could possibly be made. Substitutions among the charged acidic amino acids, aspartic acid and glutamic acid, could possibly be made, as could substitutions among the charged basic amino acids, lysine and arginine. Substitutions among the aromatic amino acids, including phenylalanine, histidine, tryptophan and tyrosine would also likely be possible. In some situations, histidine and basic amino acids lysine and arginine may be substituted for each other. These sorts of substitutions and interchanges are well known to those skilled in the art. Other substitutions might well be possible. It is expected that the greater the percentage of sequence identity of a variant peptide with a peptide described herein, the greater the retention of biological activity. Accordingly, peptide variants having the activity of enhancing cholesterol ester hydrolase and/or inhibiting acyl CoA:cholesterol acyl transferase as described herein are encompassed within the scope of this invention.

Preferred for use in the present invention is an isolated peptide $(X)_n FFX_1 FX_2 X_3 X_4 X_5 FX_6$ or a portion thereof wherein F is phenylalanine or an amino acid which is a conservative substitution thereof and n is 1 or 2. Thus when n is 1, the isolated peptide comprises $XFFX_1 FX_2 X_3 X_4 X_5 FX_6$ (SEQ ID NO:13) wherein F is phenylalanine or an amino acid which is a conservative substitution thereof, X, $X_1$, $X_4$, $X_5$ and $X_6$ are independently any amino acid, $X_2$ is a hydrophobic or nonpolar amino acid; and $X_3$ is histidine or an amino acid which is a conservative substitution thereof. When n is 2, the isolated peptide comprises $X_a X_b FFX_1 FX_2 X_3 X_4 X_5 FX_6$ (SEQ ID NO:14), wherein F is phenylalanine or an amino acid which is a conservative substitution thereof, $X_a$ and $X_6$ are amino acids capable of forming a salt bridge, and $X_b$, X, $X_1$, $X_2$, $X_3$, $X_4$ and $X_5$ are independently any amino acid, or a mimetic thereof. Examples of amino acid combinations of $X_a$ and $X_6$ forming salt bridges include, but are not limited to, $X_a$ being arginine and $X_6$ being aspartic acid or glycine. In certain preferred embodiments, the isolated peptide or mimetic thereof comprises one or more D amino acids. The number of D amino acids included in the peptide or mimetic thereof is selected so that a functional structure is maintained. More preferred are isolated peptides consisting of amino acid residues 1-20 (GFFSFVHEAFQGAGDMWRAY SEQ ID NO:1) of murine SAA2.1, amino acid residues 1-23 (RSFFSFLGEAFDGARDMWRAYSD; SEQ ID NO:6) or 1-20 (RSFFSFLGEAFDGARDMWRA; SEQ ID NO:30) of human SAA1.1 or SAA2.1, and RGFFSFIGEAFQGAGDMWRAY (SEQ ID NO:7). These isolated peptides of the present invention are capable of inhibiting acyl CoA:cholesterol acyl transferase. Excluded from the scope of the peptides of the present invention capable of inhibiting acyl CoA:cholesterol acyl transferase activity are those isolated peptides consisting of GFFSFVHEAFQGAGDM (SEQ ID NO:15), GFFSFIGEAFQGAGDM (SEQ ID NO:16), RSFFSFLGEAFDGARDMW (SEQ ID NO:17), GFFSFIGEAFQGAGDMWRAYTDMKEAGWKDGDKYFHARGNYDAAQRGPGGVWAAEKISD ARESFQEFFGRGHEDTMADQEANRHGRSGKDPNYYRPPGLPAKY (full length murine SAA1.1;SEQ ID NO:18); GFFSFVHEAFQGAGDMWRAYTDMKEANWKNSDKYFHARGNYDAAQRGPGGVWAAEKISD GREAFQEFFGRGHEDTIADQEANRHGRSGKDPNYYRPPGLPDKY (full length murine SAA2.1; SEQ ID NO:19); RSFFSFLGEAFDGARDMWRAYSDMREANYIGSDKYFHARGNYDAAKRGPGGVWAAEAIS DARENIQRFFGHGAEDSLADQAANEWGRSGKDPNHFRPAGLPEKY (full length human SAA1.1; SEQ ID NO:20); or RSFFSFLGEAFDGARDMWRAYSDMREANYIGSDKYFHARGNYDAAKRGPGGAWAAEVIS NARENIQRLTGHGAEDSLADQAANKWGRSGRDPNHFRPAGLPEKY (full length human SAA2.1; SEQ ID NO:21).

Preferred isolated peptides capable of enhancing cholesterol ester hydrolase activity for use in the present invention comprise $X_1 X_2 X_3 X_4 X_5 X_6 X_7 X_8 X_9 X_{10} X_{11} X_{12} X_{13} X_{14} X_{15} X_{16} X_{17} X_{18}$ (SEQ ID NO:29) or a portion thereof wherein $X_1$ and $X_9$, $X_{12}$ or $X_{18}$ are amino acids capable of forming a salt bridge, $X_6$ is glutamic acid or lysine or an amino acid which is a conservative substitution thereof, and $X_2$, $X_3$, $X_4$, $X_5$, $X_7$, $X_8$, $X_{10}$, $X_{11}$, $X_{13}$, $X_{14}$, $X_{15}$, $X_{16}$, and $X_{17}$ are independently any amino acid. Preferred is the peptide comprising $X_1 X_2 X_3 X_4 X_5 X_6 X_7 X_8 X_9 X_{10} X_{11} X_{12} X_{13} X_{14} X_{15} X_{16} X_{17} X_{18}$ (SEQ ID NO:29) wherein $X_1$ and $X_9$, $X_{12}$ or $X_{18}$ are amino acids capable of forming a salt bridge, $X_2$ is glutamine or an amino acid which is a conservative substitution thereof, $X_3$ and $X_4$ are independently alanine or an amino acid which is a conservative substitution thereof, $X_5$ and $X_{15}$ are independently asparagine or an amino acid which is a conservative substitution thereof, $X_7$ is tryptophan or an amino acid which is a conservative substitution thereof, $X_8$ and $X_{11}$ are independently glycine or an amino acid which is a conservative substitution thereof, $X_{10}$ is serine or an amino acid which is a conservative substitution thereof, $X_{13}$ is aspartic acid or an amino acid which is a conservative substitution thereof, $X_{14}$ is proline or an amino acid which is a conservative substitution thereof, $X_{16}$ is histidine or an amino acid which is a conservative substitution thereof, and/or $X_{17}$ is phenylalanine or an amino acid which is a conservative substitution thereof. Examples of amino acid combinations capable of forming a salt bridge include $X_1$ being an aspartic acid and $X_9$, $X_{12}$ or $X_{18}$ being an arginine. It is preferred that the isolated peptide or mimetic has less than 80 amino acid residues, more preferably 18 to 79 amino acids, more preferably 18 to 50 amino acids, more preferably 18 to 35, 18 to 30, or 18 to 25 amino acids. Also preferred are isolated peptides DTIADQEANRHGRSGKDPNYYRPPGLPDKY (SEQ ID NO:4), ADQEANRHGRSGKDPNYYRPPGLPDKY (SEQ ID NO:8), ADQEANRHGRSGKDPNYYRPPGLPAKY (D-form; SEQ ID NO:10), ADQEANRHGRSGKDPNYYR (SEQ ID NO:25), ADQAANKWGRSGRDPNHFR (SEQ ID NO:11), ADQAANEWGRSGKDPNHFR (SEQ ID NO:12); ADQAANEWGRSGKDPNHFR (D-form; SEQ ID NO:32); ADQAANEWGRSGKDPNHFRPAGLPEKY (D-form; SEQ ID NO:31), or DQAANKWGRSGRDPNHFR (SEQ ID NO:26), or a peptide variant of one of these peptides or a portion thereof or a peptide variant of ADQEANRHGRSGKDPNYYRPPGLPAKY (SEQ ID NO:9) or ADQAANEWGRSGKDPNHFRPAGLPEKY (SEQ ID NO:24). Excluded from the scope of the peptides of the present invention capable of enhancing cholesterol ester hydrolase activity are those isolated peptides consisting GFFSFIGEAFQGAGDMWRAYTD-MKEAGWKDGDKYFHARGNYDAAQRGPG-GVWAAEKISD ARESFQEFFGRGHEDTMADQEANRHGRS-GKDPNYYRPPGLPAKY (full length murine SAA1.1; SEQ ID NO:18); GFFSFVHEAFQGAGDMWRAYTDMKEANWKNSDKYFHARGNYDAAQRGPGGVWAAEKISDG REAFQEFFGRGHEDTIADQEANRHGRS-GKDPNYYRPPGLPDKY (full length murine SAA2.1; SEQ ID NO:19); RSFFSFLGEAFDGARDMWRAYSDMREA-NYIGSDKYFHARGNYDAAKRGPGGVWAAEAISD ARENIQRFFGHGAEDSLADQAANEWGRS-GKDPNHFRPAGLPEKY (full length human SAA1.1; SEQ ID NO:20); RSFFSFLGEAFDGARDMWRAYSDMREA-NYIGSDKYFHARGNYDAAKRGPGGAWAAEVISN ARENIQRLTGHGAEDSLADQAANKWGRS-GRDPNHFRPAGLPEKY (full length human SAA2.1; SEQ ID NO:21); KEAGWKDGDKYFHARGNYDAAQRGPG-GVWAAEKISDARESFQEFFGRGHEDTMADQEANR HGRSGKDPNYYRPPGLPAKY (SEQ ID NO:22); KEAN- WKNSDKYFHARGNYDAAQRGPG-GVWAAEKISDGREAFQEFFGRGHEDTIDQEANRHGRSGKDPNYYRPPGLPDKY (SEQ ID NO:23); ADQEANRHGRSGKDPNYYRPPGLPAKY (SEQ ID NO:9); or ADQAANEWGRSGKDPNHFRPAGLPEKY (SEQ ID NO:24).

Also preferred for use in the present invention to enhance cholesterol ester hydrolase activity and/or inhibit acyl CoA:cholesterol acyl transferase activity are compounds with a formula of Y-Z or Q-Y-Z. In these compounds Z is linked to Y and/or Q is linked to Y-Z via any acceptable binding means and selected based upon selection of Z or Q. Examples of acceptable binding means include, but are in no way limited to, covalent binding, noncovalent binding, hydrogen binding, antibody-antigen recognition, or ligand binding. In compounds with the formula Y-Z or Q-Y-Z, Y comprises an isolated peptide or mimetic of the present invention with cholesterol ester hydrolase enhancing activity and/or acyl CoA:cholesterol acyl transferase inhibitory activity; Z comprises a compound linked to Y that enhances the performance of Y; and in embodiments comprising Q, Q may be identical to Z or different from Z and also enhances performance of the compound Q-Y-Z. Preferred are compounds with isolated peptides or mimetics thereof containing one or more D amino acids. Exemplary Z or Q compounds include, but are not limited to, a targeting agent a second agent for treatment of atherosclerosis, cardiovascular disease or coronary heart disease, an agent which enhances solubility, absorption, distribution, half-life, bioavailability, stability, activity and/or efficacy, or an agent which reduces toxicity or side effects of the compound. Exemplary targeting agents of Z and/or Q include macrophage targeting agents such as, for example, a liposome, a microsphere, or a ligand for a SAA receptor, hepatic targeting agents, antibodies and active fragments thereof such as, for example, Fab fragments, and additional agents specific to atherosclerotic plaques and/or inflammatory sites.

By "isolated" as used herein it is meant a peptide substantially separated from other cellular components that naturally accompany the native peptide or protein in its natural host cell. The term is meant to be inclusive of a peptide that has been removed from its naturally occurring environment, is not associated with all or a portion of a peptide or protein in which the "isolated peptide" is found in nature, is operatively linked to a peptide to which it is not linked or linked in a different manner in nature, does not occur in nature as part of a larger sequence or includes amino acids that are not found in nature. The term "isolated" also can be used in reference to recombinantly expressed peptides, chemically synthesized peptides, or peptide analogs that are biologically synthesized by heterologous systems.

By "human equivalent" as used herein, it is meant a peptide sequence derived from human SAA2.1 or human SAA1.1 with similar activity to the referenced murine peptides herein.

By the phrase "derived from" it is meant to include peptides or mimetics that originated from a particular species and were isolated from that particular species as well as peptides identical in amino acid sequence which are recombinantly expressed in a host cell expression system or chemically synthesized.

By "mimetic" as used herein it is meant to be inclusive of peptides, which may be recombinant, and peptidomimetics, as well as small organic molecules, which exhibit similar or enhanced acyl CoA:cholesterol acyl transferase, and/or cholesterol ester hydrolase modulating activity. These include peptide variants which comprise conservative amino acid substitutions relative to the sequence of the native domains of SAA2.1 or SAA1.1 and peptide variants which have a high percentage of sequence identity with the native domains of SAA2.1 or SAA1.1, at least e.g. 80%, 85%, 90%, preferably at least 95%, 96%, 97%, 98%, or 99% sequence identity, and more preferably at least 99.5% or 99.9% sequence identity. Variant peptides can be aligned with the reference peptide to assess percentage sequence identity in accordance with any of the well-known techniques for alignment. For example, a variant peptide greater in length than a reference peptide is aligned with the reference peptide using any well known technique for alignment and percentage sequence identity is calculated over the length of the reference peptide, notwithstanding any additional amino acids of the variant peptide, which may extend beyond the length of the reference peptide.

Preferred variants include, but are not limited to, peptides comprising one or more D amino acids, which are equally effective but less susceptible to degradation in vivo, and cyclic peptides. As demonstrated herein, D peptides of the present invention are effective at increasing cholesterol efflux in vivo when administered either intravenously or orally. Further, formulations administered and demonstrated to be effective comprised solutions of the D peptide in aqueous vehicles such as phosphate buffered saline and phosphate buffered saline containing 5% weight/volume glucose. In addition, lipid/liposome formulations of D-form peptides of the present invention, like lipid/liposome formulations of L-form peptides of the present invention were effective at increasing cholesterol efflux. These peptides and mimetics are therefore believed to be effective at regressing and/or decreasing formation of arterial atherosclerotic lesions and treating or preventing atherosclerosis, cardiovascular disease, coronary heart disease and inflammation in a subject. Cyclic peptides can be circularized by various means including but not limited to peptide bonds or depsicyclic terminal residues (i.e. a disulfide bond).

Also preferred is a variant comprising two or more linked or conjugated peptides of the present invention. Particularly preferred is a variant comprising a peptide capable of enhancing cholesterol ester hydrolase activity linked or conjugated to a peptide capable of inhibiting acyl CoA:cholesterol acyl transferase activity.

As used herein, the term "peptidomimetic" is intended to include peptide analogs that serve as appropriate substitutes for the peptides of SEQ ID NO:1, 4, 6, 7, 8, 9 10, 11, 12, 13, 14, 24, 25, 26, 29, 30, 31 or 32 in modulating acyl CoA:cholesterol acyl transferase and/or cholesterol ester hydrolase activity. The peptidomimetic must possess not only similar chemical properties, e.g. affinity, to these peptide domains, but also efficacy and function. That is, a peptidomimetic exhibits function(s) of an acyl CoA:cholesterol acyl transferase inhibitory domain of SAA2.1 and/or a cholesterol ester hydrolase enhancing domain of SAA2.1, without restriction of structure. Peptidomimetics of the present invention, i.e. analogs of the acyl CoA:cholesterol acyl transferase inhibitory domain of SAA2.1 and/or the cholesterol ester hydrolase enhancing domain of SAA2.1, include amino acid residues or other moieties which provide the functional characteristics described herein. Peptidomimetics and methods for their preparation and use are described in Morgan et al. 1989, "Approaches to the discovery of non-peptide ligands for peptide receptors and peptidases," In Annual Reports in Medicinal Chemistry (Vuirick, F. J. ed), Academic Press, San Diego, Calif., 243-253.

Mimetics of the present invention may be designed to have a similar structural shape to the acyl CoA:cholesterol acyl transferase inhibitory domain of SAA2.1 or the cholesterol ester hydrolase enhancing domain of SAA2.1. For example, mimetics of the acyl CoA:cholesterol acyl transferase inhibitory domain of SAA2.1 of the present invention can be designed to include a structure which mimics aromatic amino acids such as those characterized by $(X)_n FFX_1FX_2X_3X_4X_5FX_6$ (SEQ ID NO:13 or SEQ ID NO:14), e.g. residues 1-11 of SEQ ID NO:1, residues 2-12 of SEQ ID NO;6 or residue 1-12 of SEQ ID NO:7, and which is folded or stacked (e.g. pi-bonded) in an appropriate conformation to exhibit activity of inhibition of acyl CoA:cholesterol acyl transferase. The efficacy of mimetics of the present invention having aromatic regions as acyl CoA:cholesterol acyl transferase inhibitors is also reasonably expected in light of the aromaticity found in various known ACAT inhibitors (McCarthy et al. J. Med. Chem. 1994 37:1252-1255). For polypeptide mimetics or peptidomimetics of the present invention mimicking the stacked or folded aromatic amino acids of the acyl CoA:cholesterol acyl transferase inhibitory domain of SAA2.1, preferred amino acids for inclusion include, but are not limited to, trytophan, phenylalanine, histidine and tyrosine.

Mimetics of the present invention with cholesterol ester hydrolase enhancing domain may also be designed to include a structure which mimics the salt bridge conformation of $X_1X_2X_3X_4X_5X_6X_7X_8X_9X_{10}X_{11}X_{12}X_{13}X_{14}X_{15}X_{16}X_{17}X_{18}$ (SEQ ID NO:29) or a portion thereof wherein $X_1$ and $X_9$, $X_{12}$ or $X_{18}$ are amino acids capable of forming a salt bridge, $X_6$ is glutamic acid or lysine or an amino acid which is a conservative substitution thereof, and $X_2$, $X_3$, $X_4$, $X_5$, $X_7$, $X_8$, $X_{10}$, $X_{11}$, $X_{13}$, $X_{14}$, $X_{15}$, $X_{16}$, and $X_{17}$ are independently any amino acid.

Mimetics of the acyl CoA:cholesterol acyl transferase inhibitory domain of SAA2.1 or the cholesterol ester hydrolase enhancing domain of SAA2.1 can also be designed to have a similar structure to the synthetic peptides of SEQ ID NO:1, 6, 7, 13, 14 or 30, or SEQ ID NO:4, 8, 9, 10, 11, 12, 24, 25, 26, 29, 31 or 32, respectively. These, peptidomimetics may comprise peptide sequences with conservative amino acid substitutions as compared to SEQ ID NO:1, 6, 7, 13, 14 or 30 or SEQ ID NO:4, 8, 9, 10, 11, 12, 24, 25, 26, 29, 31 or 32 which interact with surrounding amino acids to form a similar structure to these synthetic peptides. Conformationally restricted moieties such as a tetrahydroisoquinoline moiety may also be substituted for a phenylalanine, while histidine bioisoteres may be substituted for histidine to decrease first pass clearance by biliary excretion. Peptidomimetics of the present invention may also comprise peptide backbone modifications. Analogues containing amide bond surrogates are frequently used to study aspects of peptide structure and function including, but not limited to, rotational freedom in the backbone, intra- and intermolecular hydrogen bond patterns, modifications to local and total polarity and hydrophobicity, and oral bioavailability. Examples of isosteric amide bond mimics include, but are not limited to, Ψ[CH$_2$S], Ψ[CH$_2$NH], Ψ[CSNH$_2$], Ψ[NHCO], Ψ[COCH$_2$] and Ψ[(E) or (Z)CH═CH].

Mimetics can also be designed with extended and/or additional amino acid residue repeats as compared to the naturally occurring acyl CoA:cholesterol acyl transferase inhibitory domain of SAA2.1 and/or the cholesterol ester hydrolase enhancing domain of SAA2.1. For example, mimetics comprising two or more repeats of $(X)_n FFX_1FX_2X_3X_4X_5FX_6$ (SEQ ID NO:13 or SEQ ID NO:14), e.g. residues 1-11 of SEQ ID NO:1, residues 2-12 of SEQ ID NO;6 or residue 1-12 of SEQ ID NO:7, portion of the acyl CoA:cholesterol acyl transferase inhibitory domain, which may be flanked and/or separated by stabilizing amino acids, may be active inhibitors of acyl CoA:cholesterol acyl transferase. Alternatively, such repeats may contain one or more substitutions of one aromatic amino acid for another aromatic amino acid, e.g. W, H, or Y for F. Further, amino acids of these peptides believed to be important to the activity and/or stability of the conformation of the peptides, such as the initial arginine of SEQ ID NO:6 which is believed to form a hydrogen bond with an internal residue in the region of residues 12-13 of SEQ ID NO:6, may be incorporated into mimetics to enhance their activity and/or stability. Host cells can be genetically engineered to express such mimetics in accordance with routine procedures.

Identification of these peptide domains also permits molecular modeling based on these peptides for design, and subsequent synthesis, of small organic molecules that have cholesterol ester hydrolase enhancing and/or acyl CoA:cholesterol acyl transferase-inhibiting activities. These small organic molecules mimic the structure and activity of the peptides of SEQ ID NO:1, 4, 6, 7, 8, 9, 10, 11, 12, 13, 14, 24, 25, 26, 29, 30, 31 or 32. However, instead of comprising amino acids, these small organic molecules comprise bioisosteres thereof, substituents or groups that have chemical or physical similarities, and exhibit broadly similar biological activities.

Bioisosterism is a lead modification approach used by those skilled in the art of drug design and shown to be useful in attenuating toxicity and modifying activity of a lead compound such as SEQ ID NO:1, 4, 6, 7, 8, 9, 10, 11, 12, 13, 14, 24, 25, 26, 29, 30, 31 or 32. Bioisosteric approaches are discussed in detail in standard reference texts such as The Organic Chemistry of Drug Design and Drug Action (Silverman, R B, Academic Press, Inc. 1992 San Diego, Calif., pages 19-23). Classical bioisosteres comprise chemical groups with the same number of valence electrons but which may have a different number of atoms. Thus, for example, classical bioisosteres with univalent atoms and groups include, but are not limited to: CH$_3$, NH$_2$, OH, F and Cl; Cl, PH$_2$ and SH; Br and i-Pr; and I and t-Bu. Classical bioisosteres with bivalent atoms and groups include, but are not limited to: —CH$_2$— and NH; O, S, and Se; and COCH$_2$, CONHR, CO$_2$R and COSR. Classical bioisosteres with trivalent atoms and groups include, but are not limited to: CH═ and N═; and P═ and As═. Classical bioisosteres with tetravalent atoms include, but are not limited to: C and Si; and ═C$^+$═, ═N$^+$═ and ═P$^+$═. Classical bioisosteres with ring equivalents include, but are not limited to: benzene and thiophene; benzene and pyridine; and tetrahydrofuran, tetrahydrothiophene, cyclopentane and pyrrolidine. Nonclassical bioisosteres still produce a similar biological activity, but do not have the same number of atoms and do not fit the electronic and steric rules of classical isosteres. Exemplary nonclassical bioisoteres are shown in the following Table.

Nonclassical Biosteres

1. Carbonyl group

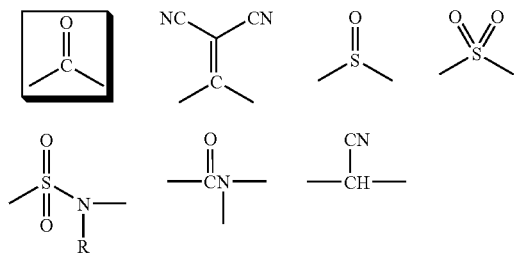

-continued

Nonclassical Biosteres

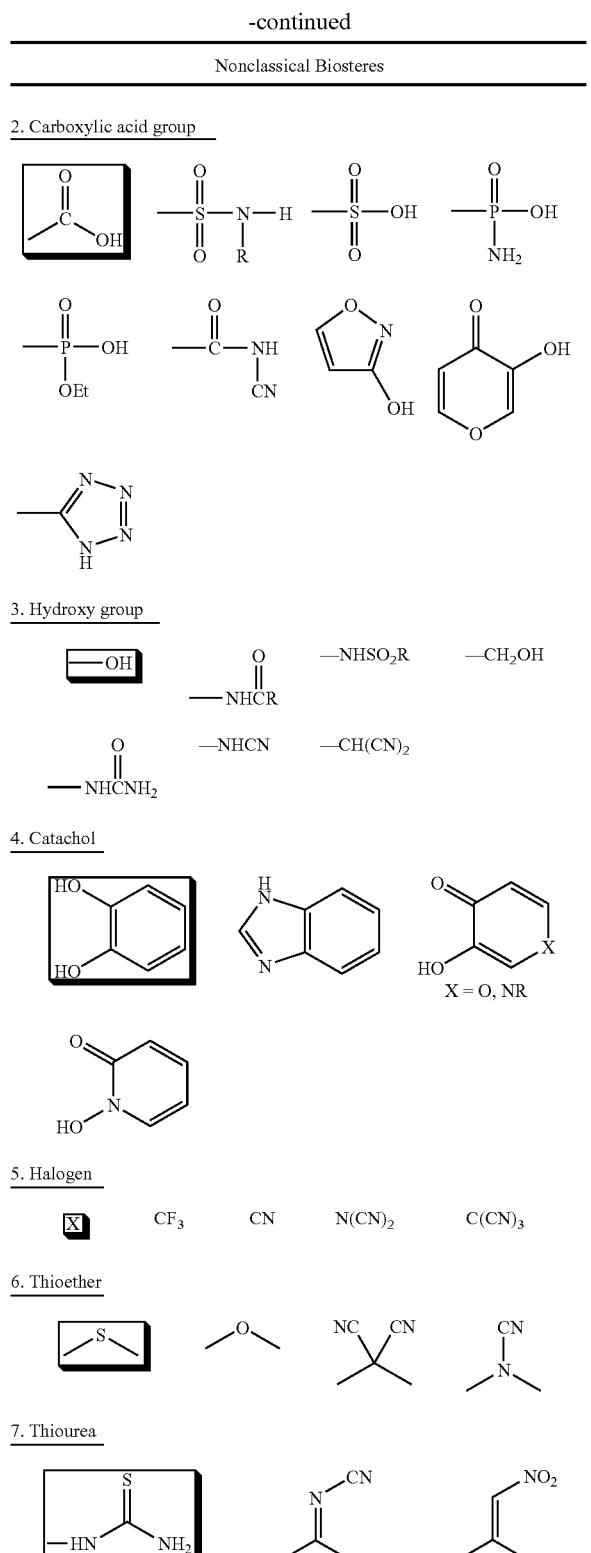

-continued

Nonclassical Biosteres

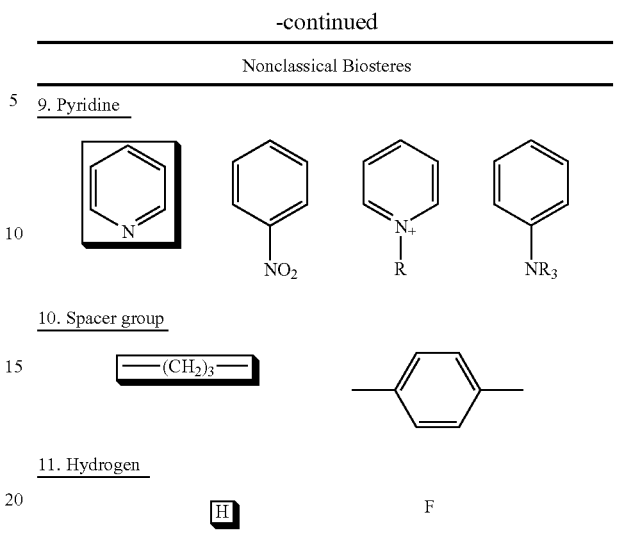

Additional bioisosteric interchanges useful in the design of small organic molecule mimetics of the present invention include ring-chain transformations.

A peptide or portion thereof, Y-Z or Q-Y-Z compound or mimetic thereof of the present invention is preferably formulated with a vehicle pharmaceutically acceptable for administration to a subject, preferably a human, in need thereof. Methods of formulation for such compositions are well known in the art and taught in standard reference texts such as *Remington's Pharmaceutical Sciences*, Mack Publishing Co., Easton, Pa., 1985. A composition of the present invention may comprise a single peptide or portion thereof, a Y-Z or Q-Y-Z compound, or a mimetic of these which modulates either acyl CoA:cholesterol acyl transferase activity or cholesterol ester hydrolase activity, or both acyl CoA:cholesterol acyl transferase activity and cholesterol ester hydrolase activity. Further, compositions of the present invention may comprise a peptide of SEQ ID NO: 1, 6, 7, 13, 14 or 30 or a portion or a mimetic thereof and a peptide of SEQ ID NO:4, 8, 9 10, 11, 12, 24, 25, 26, 29, 31 or 32 or a portion or a mimetic thereof. These compositions may be administered alone or in combination with a second cholesterol-lowering drug or agent. For example, a composition of the present invention comprising a peptide of SEQ ID NO:4, 8, 9, 10, 11, 12, 24, 25, 26, 29, 31 or 32 or a mimetic thereof which inhibits cholesterol ester hydrolase activity, can be administered to a subject in combination with an ACAT inhibitor. Exemplary ACAT inhibitors include but are not limited to Zetia™ (Merck), Avasimibe (Pfizer), Eflucimibe (Eli Lilly) and CS-505 (Sankyo). Compositions of the present invention may also be administered to a subject with an apolipoprotein free cholesterol acceptor (Rothblat et al. J. Lipid Res. 1999 40:781-796; Li et al. Biochimica Biophysica Acta 1995 1259:227-234; Jian et al. J. Biol. Chem. 1998 273(10):5599-5606). An example of an apolipoprotein free cholesterol acceptor is cyclodextrin. Additional exemplary cholesterol-lowering drugs or agents which can be administered in combination with an isolated peptide or mimetic of the present invention include, but are not limited to, statins, resins or bile acid sequestrants (Bays et al. Expert Opinion on Pharmacotherapy 2003 4(11):1901-38; Kajinami et al. Expert Opinion on Investigational Drugs 2001 11(6):831-5), niacin (Van et al. Am. J. Cardiol. 2002 89(11):1306-8; Ganji et al. J. Nutri. Biochem. 2003 14(6):298-305; Robinson et al. Progress in Cardiovasc. Nursing 2001 16(1):14-20; Knopp, R. H. Am. J. Cardiol. 2000 86(12A):51L-56L), liver X receptor agonists (Tontonoz et al. Molecular Endocrinology 2003 17:985-993), Ca2+ antagonists (Delsing et al. Cardiovasc. Pharmacol. 2003 42(1):63-70) and modulators of peroxisome proliferator-activated receptors (PPARs; Lee et al. Endocrinology 2003 144:2201-2207).

A preferred formulation for use in the present invention is complexing the peptide or mimetic thereof or Y-Z or Q-Y-Z compound with a lipid. Also preferred as a formulation is encapsulation of the peptide or mimetic thereof or Y-Z or Q-Y-Z compound or mimetic thereof in a phospholipid vesicle. As demonstrated throughout the instant application, an exemplary phospholipid vesicle useful in the present invention is a liposome. Liposomes containing the peptide or mimetic thereof or Y-Z or Q-Y-Z compound or mimetic thereof of the present invention can be prepared in accordance with any of the well known methods such as described by Epstein et al. (Proc. Natl. Acad. Sci. USA 82: 3688-3692 (1985)), Hwang et al. (Proc. Natl. Acad. Sci. USA 77: 4030-4034 (1980)), EP 52,322, EP 36,676; EP 88,046; EP 143,949; EP 142,641; Japanese Pat. Appl. 83-118008, and EP 102,324, as well as U.S. Pat. Nos. 4,485,045 and 4,544,545, the contents of which are hereby incorporated by reference in their entirety. Preferred liposomes are of the small (about 200-800 Angstroms) unilamellar type in which the lipid content is greater than about 10 mol. percent cholesterol, preferably in a range of 10 to 40 mol. percent cholesterol, the selected proportion being adjusted for optimal peptide therapy. However, as will be understood by those of skill in the art upon reading this disclosure, phospholipid vesicles other than liposomes can also be used.

As demonstrated herein, another preferred formulation, comprises a peptide comprising a D amino acid and an aqueous vehicle suitable for intravenous or oral administration. Intravenous formulations expected to be useful in the present invention include, but are not limited to, sterile aqueous solutions (where water soluble) or dispersions and sterile powders for the extemporaneous preparation of sterile injectable solutions or dispersions. In all cases, the composition must be sterile and must be fluid to the extent that easy syringability exists. It must be stable under the conditions of manufacture and storage and must be preserved against the contaminating action of microorganisms such as bacteria and fungi. The vehicle can be a solvent or dispersion medium containing, for example, water, ethanol, polyol (for example, glycerol, propylene glycol, liquid polyethylene glycol, and the like), suitable mixtures thereof, and oils (e.g., vegetable oil). The proper fluidity can be maintained, for example, by the use of a coating such as lecithin, by the maintenance of the required particle size in the case of dispersion, and by the use of surfactants.

Prevention of the action of microorganisms can be achieved by various antibacterial and antifungal agents, for example, parabens, chlorobutanol, phenol, ascorbic acid, thimerosal, and the like. In some cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the peptide of the present invention in the required amount in an appropriate solvent with one or a combination of ingredients enumerated above, as required, followed by filter sterilization. Generally, dispersions are prepared by incorporating the peptide of the present invention into a sterile vehicle which contains a basic dispersion medium and the required other ingredients from those enumerated above. In the case of sterile powders for the preparation of sterile injectable solutions, the preferred methods of preparation are vacuum drying and freeze-drying which yield a powder of the active ingredient (i.e., the peptide) optionally plus any additional desired ingredient from a previously sterile-filtered solution thereof.

Solid dosage forms for oral administration of a peptide of the present invention include, but are not limited to, ingestible capsules, tablets, pills, lollipops, powders, granules, elixirs, suspensions, syrups, wafers, sublingual or buccal tablets, troches, and the like. In such solid dosage forms the peptide is mixed with at least one inert, pharmaceutically acceptable excipient or diluent or assimilable edible carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof, or incorporated directly into the subject's diet. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like. The percentage of the peptide in the compositions and preparations may, of course, be varied. The amount of the peptide in such therapeutically useful compositions is such that a suitable dosage will be obtained.

The solid dosage forms of tablets, dragees, capsules, pills, and granules can be prepared with coatings and shells such as enteric coatings and other coatings well-known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes. The peptides can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the peptide, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, ground nut corn, germ olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Suspensions, in addition to the peptide, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

The peptides, compounds and mimetics of these or pharmaceutical compositions of the present invention can also be administered via a coronary stent implanted into a patient. Coronary stents which elute a peptide, compound and mimetic of these or a pharmaceutical composition of the present invention can be prepared and implanted in accordance with well known techniques (See, for example, Woods et al. (2004) Annu. Rev. Med. 55:169-78); al-Lamce et al. (2003) Med. Device Technol. 2003 14:12-141 Lewis et al. 2002 J. Long Term Eff. Med. Implants 12:231-50; Tsuji et al. 2003 Int. J. Cardiovasc. Intervent. 5:13-6).

Pharmaceutical compositions of the present invention are useful in modifying the activity of a cholesterol-metabolizing enzyme, and in particular, the activity of cholesterol ester hydrolase and/or acyl CoA:cholesterol acyl transferase. In a preferred embodiment, the pharmaceutical compositions are used to modify enzymatic activity in macrophages. More preferably, the pharmaceutical compositions are used to modify enzymatic activity in vivo. More preferably, the pharmaceutical compositions are used to modify enzymatic activity in mammals and in particular humans.

Pharmaceutical compositions of the present invention are also useful in promoting the mobilization and efflux of stored cholesterol located in atherosclerotic plaques and/or sites of inflammation. In a preferred embodiment, the pharmaceutical compositions are used to promote the mobilization and efflux of stored cholesterol from macrophages and other tissues located in atherosclerotic plaques or sites of inflammation in vivo. More preferably, the pharmaceutical compositions are used to promoting the mobilization and efflux of stored cholesterol from macrophages and other tissues located in atherosclerotic plaques or sites of inflammation in mammals and in particular humans.

Accordingly, the compositions of the present invention can be administered to a subject, preferably a mammal, more preferably a human, to treat and/or prevent atherosclerosis. The compositions may be administered by various routes including, but not limited to, orally, intravenously, intramuscularly, intraperitoneally, topically, rectally, dermally, sublingually, buccally, intranasally or via inhalation. In a preferred embodiment, the composition administered comprises a peptide or mimetic thereof with one or more D amino acids. The formulation and route of administration as well as the dose and frequency of administration can be selected routinely by those skilled in the art based upon the severity of the condition being treated, as well as patient-specific factors such as age, weight and the like. The prolonged activity of synthetic peptides of the present invention in promoting cholesterol efflux from macrophages is indicative of the feasibility of daily, every other day or semi-weekly dosing regime for these pharmaceutical compositions.

In addition to the above-described in vitro and in vivo assays, efficacy of compositions of the present invention to treat and/or prevent atherosclerosis can also be demonstrated in an animal model such as the ApoE knockout mouse model of atherogenesis (Davis et al. Arterioscler Thromb Vasc Biol. 2001 21:2031-2038). These mice, when placed on an atherogenic diet, rapidly deposit lipid into their aortas. The ApoE knockout mice are a validated model of atherosclerosis and were used to demonstrate the effectiveness of Ezetimibe (Zetia™; Merck) in reducing atherosclerosis (Davis et al. Arterioscler Thromb Vasc Biol. 2001 21:2031-2038). The efficacy of compositions of the present invention, such as, e.g., those comprising one or more peptides of SEQ ID NO: 1, 4 or 6 or a mimetic thereof, in treating or preventing atherosclerosis can be demonstrated in similar fashion.

The in vivo effectiveness of a composition of the present invention, such as a composition comprising a peptide of SEQ ID NO:1, 4, 6, 7, 8, 9, 10, 11, 12, 13, 14, 24, 25, 26, 29, 30, 31 or 32 in preventing or reducing the degree of atherosclerosis, can be demonstrated in the above rodent model for atherogenesis. To demonstrate the ability of a composition of the present invention to cause regression of atherosclerosis, the rodent is placed on an atherogenic diet, such as described in Example 11, for two weeks. The animals are then divided into two groups, one group which continues on the diet for an additional two weeks, the other group which continues on the diet for the same period but also receives a composition of the present invention. The effects of a composition of the present invention on aortic atherosclerosis are assessed at the termination of the experiment, when the aorta is removed from the animals and opened longitudinally. The area of the endothelial surface occupied by lipid is measured. Histological sections of aorta are also prepared for microscopic analysis and total lipids are isolated to measure the quantity of cholesterol per wet weight of tissue.

This rodent model was used to examine the anti-atherogenic activities of SAA2.1 peptides (SEQ ID NO: 1 and 4 and a combination thereof) in vivo. Livers from SAA2.1 peptide-treated mice exhibited a more normal reddish color in comparison to the whitish color observed in fatty livers of untreated mice. These data are indicative of these SAA2.1 peptides modulating cholesterol metabolism within the liver, as well as modulating macrophage cholesterol metabolism.

Further, the ability of liposomal formulations containing peptides of the present invention to prevent and induce regression of aortic lesions in the ApoE knockout mice was examined.

Figure 7A:
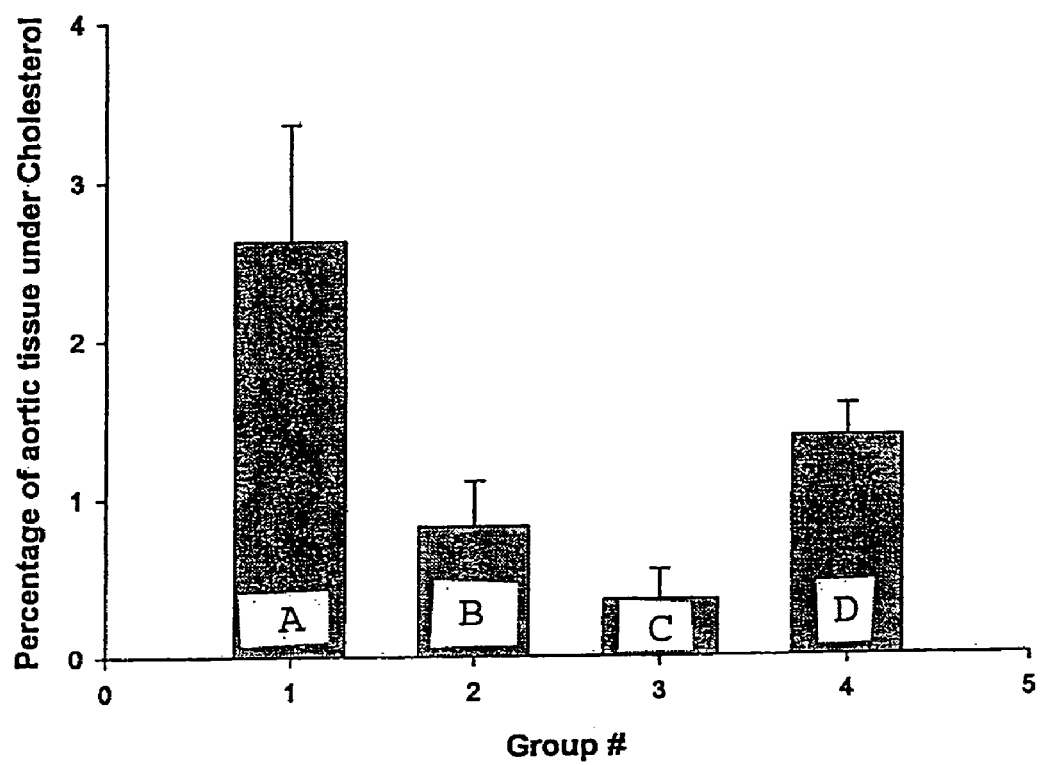
FIGS. 7A and 7B are bar graphs depicting the ability of liposomal formulations containing peptides of the present invention to reduce or cause regression of aortic lesions in ApoE knockout mice.
Figure 7B:
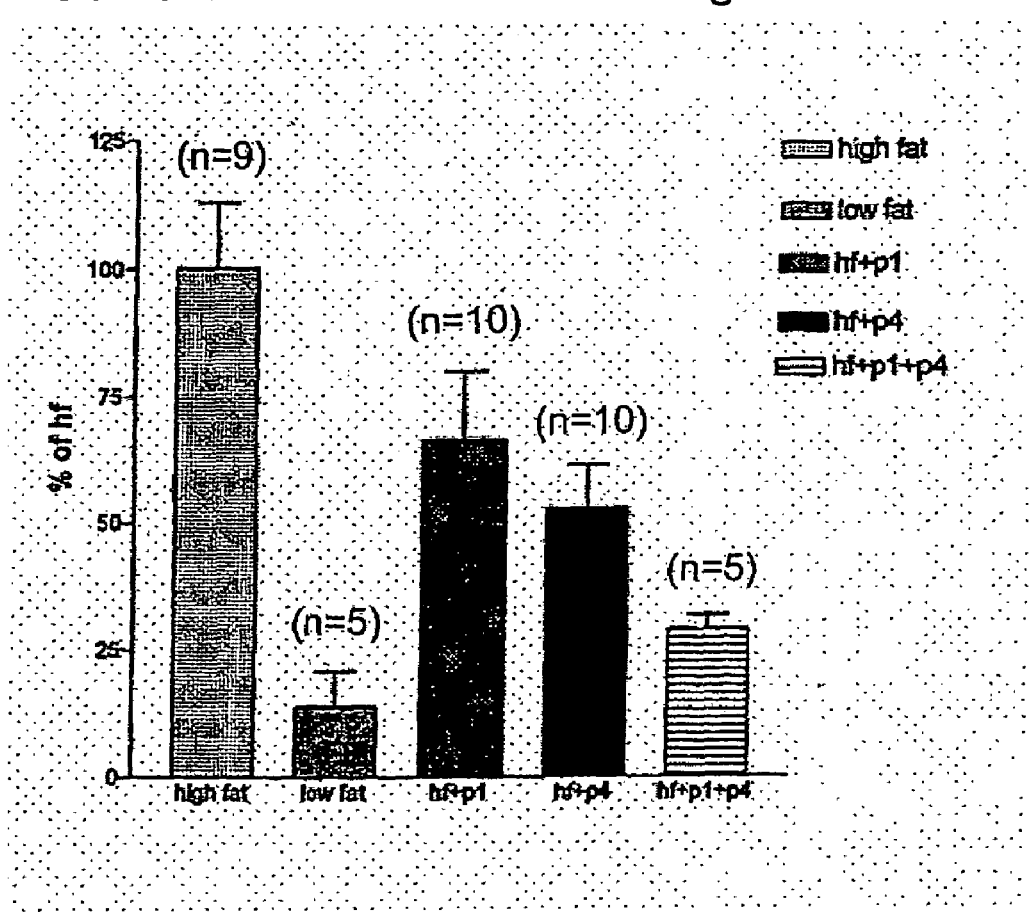

In regression experiments, ApoE knockout mice were placed on an atherogenic diet as described in Example 11 for four weeks, following which they were divided into two groups. One group continued on the diet for an additional two weeks. The other group continued on the diet for the same period but also received once every four days liposomes containing a peptide corresponding to amino acids 1-20 of murine SAA2.1 (SEQ ID NO:1; Group B of FIG. 7A and Group hf+p1 of FIG. 7B) or liposomes containing a peptide corresponding to amino acids 74-103 of murine SAA2.1 (SEQ ID NO:4; Group D of FIG. 7A and Group hf+p4 of FIG. 7B). The control group received high fat diet alone with no liposomes (Group A of FIG. 7A and Group high fat of FIG. 7B). An additional group was placed on a normal mouse chow diet (Group C of FIG. 7A and Group low fat of FIG. 7B). A further additional Group receiving liposomes containing a peptide corresponding to amino acids 1-20 of murine SAA2.1 (SEQ ID NO:1) and liposomes containing a peptide corresponding to amino acids 74-103 of murine SAA2.1 (SEQ ID NO:4) is depicted in FIG. 7B and is referred to as hf+p1+p4. FIG. 7B is inclusive of data present in FIG. 7A as well as data from a subsequent experiment performed under the same conditions. After the two weeks, the mice were killed and their aortas were dissected and stained with Oil Red O. Data of FIG. 7A depict the area stained with Oil Red O indicative of the actual lipid positive area as a percentage of the total aortic area viewed. Data of FIG. 7B depict the area stained with Oil Red O as a percentage relative to the high fat diet group (100%). As shown in these Figures, mice treated with a liposomal formulation containing a peptide of the present invention showed regression of aortic lesions as compared to control animals on the high fat diet.

Figure 8A:
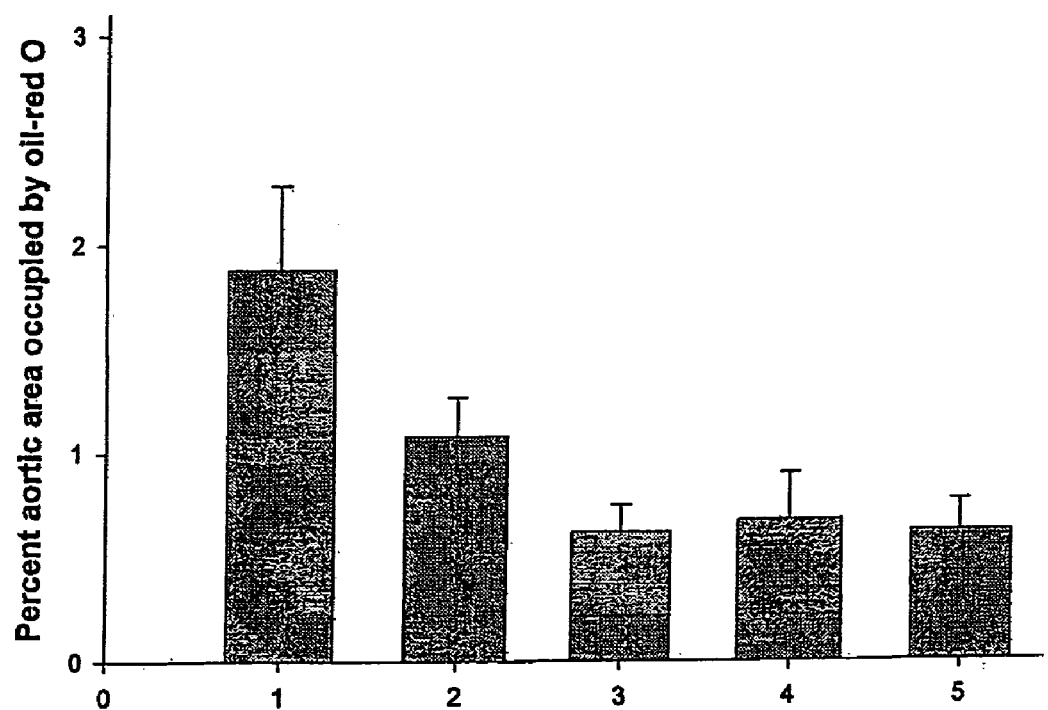
FIGS. 8A and 8B are bar graphs the ability of liposomal formulations containing peptides of the present invention to prevent aortic lesions in ApoE knockout mice.
Figure 8B:
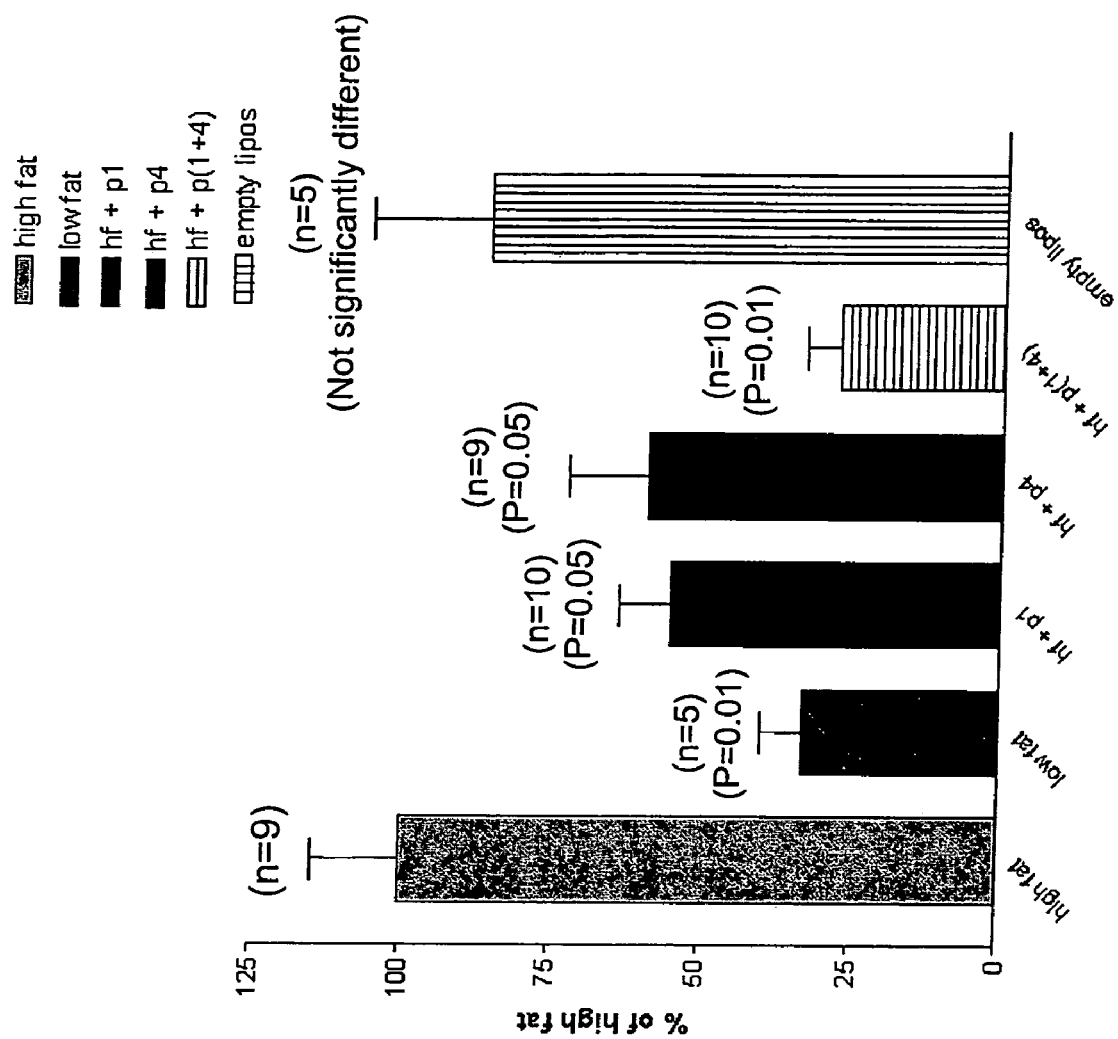

In prevention experiments, ApoE knockout mice were placed on a high fat diet and at the same time received once every four days liposomes containing a peptide corresponding to amino acids 1-20 of murine SAA2.1 (SEQ ID NO:1; Group 2 of FIG. 8A and Group hf+p1 of FIG. 8B), liposomes containing a peptide corresponding to amino acids 74-103 of murine SAA2.1 (SEQ ID NO:4; Group 4 of FIG. 8A and Group hf+p4 of FIG. 8B) or liposomes containing a peptide corresponding to amino acids 1-20 of murine SAA2.1 and a peptide corresponding to amino acids 74-103 of murine SAA2.1 (SEQ ID NO:1+SEQ ID NO:4; Group 5 of FIG. 8A and Group hf+p(1+4) of FIG. 8B). The control group received high fat diet alone with no liposomes (Group 1 of FIG. 8A and Group high fat of FIG. 8B). An additional group was placed on a normal mouse chow diet (Group 3 of FIG. 8A and Group low fat of FIG. 8B). In FIG. 8B an additional experimental group referred to as "empty lipos" was included which are animals that were treated with empty liposomes identical to the peptide containing liposomes but which are protein-peptide free. This group is different from the high fat and low fat (diet) groups that were not treated with liposomes. Data present in FIG. 8B is inclusive of data presented in FIG. 8A and a subsequent experiment performed under the same conditions. After 20 days, the mice were killed and their aortas were dissected and stained with Oil Red O. Data from these experiments are depicted in FIG. 8A and FIG. 8B. As shown therein, mice treated with a liposomal formulation containing a peptide of the present invention showed decreased aortic lesions as compared to the control animals.

These experiments in this well-accepted rodent model of atherosclerosis provide further evidence of pharmaceutical compositions of the present invention comprising an SAA peptide or mimetic modulating cholesterol metabolic pathways in various tissues and/or cells. Using techniques such as pharmacokinetic scaling, these studies in rodents can be used to predict disposition and define pharmacokinetic equivalence and to design dosage regimens in other species including humans (Mordenti, J. (1986) J. Pharmaceutical Sciences 75(11):1028-1040).

Administration of pharmaceutical compositions of the present invention is also expected to be useful in the treatment of coronary heart disease and cardiovascular disease and in the prevention or treatment of inflammation.

The invention is further illustrated by the following examples, which should not be construed as further limiting. The contents of all references, pending patent applications, and published patents cited throughout this application are hereby expressly incorporated by reference.

EXAMPLES

Example 1

Animals

Swiss-white CD1 6-8 week old female mice were obtained from Charles River, Montreal, Quebec. Mice were kept in a temperature controlled room on a 12 hour light/dark cycle. They were fed with Purina Lab Chow pellets and water ad libitum.

ApoE knockout mice were obtained from Jackson Laboratories, Maine, U.S.A.

Example 2

Chemicals

All chemicals were reagent grade and purchased from Fisher Scientific (Nepean, Ont.), Sigma (St. Louis, Mo.), ICN (Aurora, Ohio), or BioRad (Hercules, Calif.). Dulbecco's Modified Eagle Medium (DMEM) and fetal bovine serum (FBS) were purchased from Life Technologies (Burlington, Ont.). Radiolabeled [1-$^{14}$C]-oleic acid (52 mCi/mmol), [1,2,6,7-$^{3}$H(N)]-cholesterol (82 Ci/mmol), and cholesteryl-1,2,6,7-$^{3}$H(N)]-oleate (84 Ci/mmol) were obtained from DuPont NEN (Boston, Mass.).

Example 3

Peptides

The following peptides were synthesized by solid-phase chemistry:

| | |
|---|---|
| GFFSFVHEAFQGAGDMWRAY | (SEQ ID NO:1) |
| TDMKEANWKNSDKYFHARGNYDAAQRGPGG | (SEQ ID NO:2) |
| VWAAEKISDGREAFQEFFGRGHEDTIADQE | (SEQ ID NO:3) |
| DTIADQEANRHGRSGKDPNYYRPPGLPDKY | (SEQ ID NO:4) |
| GFFSFIGEAFQGAGDMWRAY | (SEQ ID NO:5) |
| RSFFSFLGEAFDGARDMWRAYSD | (SEQ ID NO:6) |
| RGFFSFIGEAFQGAGDMWRAY | (SEQ ID NO:7) |
| ADQEANRHGRSGKDPNYYRPPGLPDKY | (SEQ ID NO:8) |
| ADQEANRHGRSGKDPNYYRPPGLPAKY | (SEQ ID NO:9) |
| ADQAANKWGRSGRDPNHFR | (SEQ ID NO:11) |
| ADQAANEWGRSGKDPNHFR | (SEQ ID NO:12) |

Synthetic peptides corresponding to amino acid residues 1-20 (20-mer) (SEQ ID NO 30) and 78-96 (19-mer) (SEQ ID NO: 12) of the human SAA1.1 protein sequence, respectively, were also synthesized by Polypeptide Laboratories (PPL; Torrance Calif.). The 19-mer denoted as PPL4 in FIG. 14, enhances CEH activity and has the following sequence: ADQAANNEWGRSGKDPNHFR (SEQ ID NO:12) corresponding to amino acids 78-96 of human SAA1.1 or human SAA 2.1 (molecular mass of 2156.3 daltons). The 20-mer denoted as PPL5 in FIG. 15, inhibits ACAT activity and has the following human sequence: RSFFSFLGEAFDGARDMWRA (SEQ ID NO:30) (molecular mass of 2366.7 daltons). These human 19-mer and 20-mer sequences were also synthesized using D-form amino acid (Advanced Protein Technology Centre, The Hospital for Sick Children, Toronto).

Peptides corresponding to amino acid residues 77-103 of the murine SAA1.1 protein sequence (27-mer) were synthesized by solid-phase peptide chemistry using either L- or D-form amino acids (Protein Synthesis Laboratory at Queen's University, Kingston, Ontario, Canada). The peptide sequence of this mouse 27-mer is ADQEANRHGRSGKDP-NYYRPPGLPAKY (L-form; SEQ ID NO:9\D-form:SEQ ID NO:10) with a molecular mass of 3056.5 daltons.

The D-peptide corresponding to amino acid residues 78-104 of the human SAA1.1 protein sequence (27-mer)

(ADQAANEWGRSGKDPNHFRPAGLPEKY (D-form: SEQ ID NO:31)) was synthesized by Advanced Protein Technology Centre (The Hospital for Sick Children, Toronto). This human D-amino acid 27-mer sequence has a molecular mass of 3012.5 daltons.

Peptides h#1 and h#4 used in experiments set forth in FIG. 19 herein were synthesized by Dalton Chemical Laboratories Inc. (Toronto, Ontario, Canada).

Purities of the synthetic peptides were established by analytical high pressure liquid chromatography (HPLC) and ionspray mass spectrometry. The peptides were dialyzed against distilled water and lyophilized before use.

Example 4

Preparation of Red Blood Cell Membranes as a Source of Cholesterol

To mimic the ingestion of cell membrane fragments by macrophages at sites of tissue injury, red blood cell membrane fragments were prepared and used as a source of cholesterol in accordance with the procedure described by Ely et al. (Amyloid 2001 8:169-181). Similar quantities of cholesterol (as red blood cell membrane fragments) were used in all experiments. The concentration of cholesterol in the red blood cell membrane preparations was determined using the method of Allain and co-workers (Clin. Chem. 1974 20:470-475), with the aid of a Sigma cholesterol 20 reagent kit (Sigma Chemical Co., St. Louis, Mo.).

Example 5

Preparation of HDL, AP-HDL and Purification of apoA-1 and SAA Isoforms

HDL and AP-HDL were isolated from normal and inflamed mice, respectively, using sequential density flotation in accordance with procedure described by Ancsin and Kisilevsky (Amyloid 1999 6:37-47; J. Biol. Chem. 1999 274: 7172-7181). In this procedure, inflammation was induced by subcutaneous injection of 0.5 mL of 2% $AgNO_3$ under the loose skin of the upper back of the mice. Twenty-four hours later, after $CO_2$ narcosis, the animals were exsanguinated by cardiac puncture and the blood collected into 0.5% EDTA (final concentration). The plasma was then separated from the red blood cells by centrifugation. The induction of inflammation and SAA synthesis and the isolation of apoA-1, SAA1.1 and 2.1 from acute phase murine plasma were performed as described by Ancsin and Kisilevsky (J. Biol. Chem. 1999 274:7172-7181). Separation and purification of these proteins was accomplished by reverse phase high-pressure liquid chromatography as described by Ancsin and Kisilevsky (Amyloid 1999 6:37-47). The purity of the isolated proteins was established by mass spectrometry and N-terminal sequence analysis as described by Ancsin and Kisilevsky (Amyloid 1999 6:37-47 and J. Biol. Chem. 1999 274:7172-7181).

Example 6

Preparation and Characterization of Apolipoprotein-Lipid Complexes

ApoA-1, SAA1.1, SAA2.1, synthetic peptides corresponding to amino acid residues 1-20 of murine SAA1.1 and 2.1, respectively, and synthetic peptides corresponding to amino acid residues 21-50, 51-80 and 74-103 of murine SAA2.1 were reconstituted with lipids to form liposomes. These liposomes were made by the cholate dialysis procedure as described by Jonas et al. (J. Biol. Chem. 1989 264:4818-4825), using 1-palmitoyl-2-oleoylphosphatidylcholine/cholesterol/apolipoprotein/sodium cholate in the molar ratio 100/25/1/250. Cholesterol was included to stabilize the liposomes and give them a composition more similar to that of HDL. All preparations were done in 0.5 mL of buffer containing 10 mM Tris-HCl, pH 7.4, 0.15 M NaCl and 0.005% EDTA. The reaction mixture was stirred thoroughly and incubated for 12 to 16 hours at 4° C. At the end of the equilibration period the sample was dialyzed extensively in phosphate buffered saline at 4° C. After removing any unreacted or precipitated lipid by centrifugation at 15000×g, 15° C., for 1 hour, the liposomes were filtered on a 1.5×50 cm Sepharose CL-4B column. Following concentration, the liposomes were sterilized by filtration through a 0.45 µm Millipore filter and mixed at various concentrations with tissue culture medium. The chemical compositions of various protein-containing liposomes were obtained from protein determinations using the method of Lowry et al. (J. Biol. Chem. 1951 193:265-275), phospholipid determinations using a colorimetric kit (Wako Chemicals USA, Richmond, Va.), and enzymatic analyses of free cholesterol (Sigma cholesterol reagent kit, Sigma Chemical Co. St. Louis, Mo.).

Example 7

Cell Culture

J774 macrophages (from American Type Culture Collection, Manassas, Va.; ATCC #T1B-67) were maintained at 1 million cells per well and grown in 2 mL of DMEM supplemented with 10% FBS to 90% confluence. The medium was changed 3 times a week. In some experiments, nearly confluent mono-layers were cultured in the presence of chloroquine (100 µM) or 8-bromo-cAMP (0.3 mM).

Example 8

Cholesterol Loading and Determination of Cell Cholesterol Esterification

To load the cells with cholesterol, nearly confluent monolayers were washed 3 times with phosphate buffered saline containing 2 mg/mL fatty acid-free bovine serum albumin (PBS-BSA) and incubated for 5 hours in DMEM supplemented with 5% lipoprotein-depleted serum (LPDS) (d>1.25 g/mL) and 175 µg of red blood cell membrane cholesterol. For the purpose of pool equilibration of added cholesterol, cell cultures were rinsed twice with PBS-BSA and incubated overnight in DMEM containing 5% LPDS. The relative activity of acyl CoA:cholesterol acyl transferase was determined in cholesterol-laden cells that had been cultured in medium containing no liposomes, protein-free liposomes or liposomes containing 0.5 µM synthetic peptides corresponding to amino acid residues 1-20 (SEQ ID NO:1), 21-50 (SEQ ID NO:2), 51-80 (SEQ ID NO:3) or 74-103 (SEQ ID NO:4) of murine SAA2.1, respectively. Following 3 hours incubation with the above media, [$^{14}$C]-oleate was added and the cells were incubated for another 3 hour period (Mendez et al. J. Clin. Invest. 1994 94:1698-1705; Oram et al. Arterioscler. Thromb. 1991 11:403-414). Cells were chilled on ice and washed twice with PBS-BSA and twice with PBS. After addition of [$^3$H]-cholesteryl oleate (6000 dpm/well) as an internal standard, the lipids were extracted from the labeled cells and analyzed by thin-layer chromatography as described by Mendez et al. (J. Clin. Invest. 1994 94:1698-1705) and Oram et al. (Arterioscler. Thromb. 1991 11:403-414). The radioactivity in appropriate spots was measured to determine the incorporation of radioactivity into cholesteryl esters as a measure of acyl CoA:cholesterol acyl transferase activity.

Example 9

Rates of Hydrolysis of Cholesteryl Ester in J774 Cells

Newly confluent J774 cells were labeled with [$^{14}$C]-oleate during cholesterol loading with red blood cell membranes as described above. Cells were then incubated for up to 24 hours with 2 mL of DMEM containing 5% LPDS and 50 µg/mL of either native HDL, SAA-HDL, liposomes containing 2 µmoles of apoA-1, SAA1.1 or 2.1, or liposomes containing 0.5 µmol synthetic peptides corresponding to amino acid residues 1-20 (SEQ ID NO:1), 21-50 (SEQ ID NO:2), 51-80 (SEQ ID NO:3) and 74-103 (SEQ ID NO:4) of murine SAA2.1. To determine the rate of cholesteryl ester hydrolysis, 2 µg/mL of the acyl CoA:cholesterol acyl transferase inhibitor Sandoz 58-035 (propanimide, 3-(decyldimethylsilyl)-N-[2-(4-methylphenyl)-1-phenylethyl]-(9Cl) was added during incubation with lipoproteins or liposomes to prevent re-esterification of liberated [$^{14}$C]-oleate and free cholesterol. To examine whether or not the rate of cholesteryl ester hydrolysis involved the lysosomal cholesteryl ester hydrolase, the cells were cultured in the presence of 50 µg/mL of either native HDL and chloroquine or SAA-HDL and chloroquine (100 µM). Chloroquine is an agent that neutralizes the lysosomal proton gradient. At various time points, cellular lipids were extracted and analyzed for cholesteryl ester radioactivity as described above.

Example 10

Cholesterol Efflux in Tissue Culture and in Vivo

J774 cells were loaded with cholesterol and incubated for 3 hours with 0.5 µCi/mL [$^3$H]-cholesterol, followed by an overnight equilibration period. Cells were washed four times with PBS/BSA prior to the efflux studies. Cells were then incubated at 37° C. with DMEM/BSA and containing 5% LPDS and 50 µg/mL of either native HDL, SAA-HDL, liposomes containing 2 µmoles of apoA-1, SAA1.1 or 2.1, or liposomes containing 0.5 µmol synthetic peptides corresponding to amino acid residues 1-20 (SEQ ID NO:1), 21-50 (SEQ ID NO:2), 51-80 (SEQ ID NO:3) or 74-103 (SEQ ID NO:4) of murine SAA2.1 plus 2 µg/mL of the acyl CoA:cholesterol acyl transferase inhibitor Sandoz 58-035. The efflux media were collected at 0, 1, 2, 4, 8, 16 and 24 hours, centrifuged to remove cell debris, and then used to measure the exported counts. The cell layers were then washed twice with ice-cold PBS/BSA and twice with PBS. A portion of the cells was lysed in 0.1N NaOH to estimate both the remaining radioactivity and the cellular protein content. Cellular lipids were extracted from the remaining portion of the cells and analyzed by thin-layer chromatography as described by Mendez et al. (J. Clin. Invest. 1994 94:1698-1705) and Oram et al. (Arterioscler. Thromb. 1991 11:403-414). The radioactivity in appropriate spots was measured to determine total cellular cholesterol counts. Efflux of radioactive label to the medium was calculated as the percentage of total counts (cell+medium counts) in each well.

To examine whether cholesterol export from J774 cells to medium containing liposomes containing 2 µM murine apoA-1, SAA1.1 or SAA2.1 is a cAMP-dependent process, the radio-labeled cholesterol-laden cells were incubated overnight with 8-Br-cAMP (0.3 mM), prior to the addition of liposomes containing 2 µM murine apoA-1, SAA1.1 or SAA2.1 to the culture medium. Cholesterol efflux to the medium was then determined at the indicated time points as described above. Efflux of radioactive label to the medium was calculated as a percentage of total counts in each well.

To determine cholesterol export in vivo, J774 macrophages were cholesterol-loaded with red blood cell membranes and [$^3$H]-cholesterol as described above. Cells were washed four times with PBS/BSA and then detached from the culture dishes. Five million cells in 200 µl DMEM were injected into control mice or inflamed mice through the tail vein. At various time points, approximately 25 µl of blood were collected from the tail vein of each animal into heparinized capillary tubes and then centrifuged for 5 minutes in an Adams Autocrit Centrifuge to separate red blood cells from plasma. Cholesterol efflux was determined by measuring the appearance of [$^3$H]-cholesterol in plasma by scintillation spectrometry.

To study whether export of cholesterol from J774 cells to plasma is mediated by the ABCA1 transporter pathway, or due to the endogenous destruction of the injected cells, radiolabeled cholesterol-laden cells were incubated overnight with 400 µM (final concentration) of 4,4'-diiso-thiocyanotostilbene-2,2'-disulfonic acid (DIDS), and washed free of DIDS prior to their injection into un-inflamed and inflamed mice. Inflammation, in the form of a small sterile abscess, was induced in the back by the subcutaneous injection of 0.5 mL of a 2% solution of AgNO$_3$ as described by Kisilevsky et al. (Nat. Med. 1995 1:143-148).

Example 11

Assessing Efficacy of Peptides by Determination of Regression of Atherosclerosis The efficacy of SAA2.1 peptides in regression of atherosclerosis was examined. The peptides tested included SEQ ID NO:1 and SEQ ID NO:4. The peptides were injected intravenously once every four (4) days during atherogenic induction for a period of 2 weeks (i.e. four doses at 6 mg/kg).

To determine if these peptides cause regression of atherosclerosis, the animals were placed on an atherogenic diet (Paigen's Atherogenic Rodent Diet: Purina 5015 with cocoa butter, cholesterol and cholic acid (CI3002, Research Diets, Inc.)) for two weeks, following which they were divided into two groups of 5 animals each. One group continued on the diet for an additional two weeks. The other group continued on the diet for the same period but also received the liposome-containing peptides (4 doses, as described above).

To assess the effects of the peptides on aortic atherosclerosis, at the termination of the experiment, the aorta was removed from the animals and opened longitudinally. The endothelial surface was stained with Oil Red O and the area occupied by lipid was measured by image analysis. Furthermore, histological sections of aorta were prepared for microscopic analysis and total lipids were isolated to measure the quantity of cholesterol per wet weight of tissue. Blood was collected to measure total plasma cholesterol levels.

Livers from SAA2.1 peptide (SEQ ID NOs 1 and 4)-treated and untreated mice were also collected. Total liver tissue cholesterol and LDL levels are to be analyzed. Preliminary examination of the SAA2.1 peptide-treated livers showed that they had a more normal reddish color in comparison to the whitish color observed in livers of untreated mice. These data are the first to suggest that these SAA2.1 peptides modulate cholesterol metabolism within the liver, as well as modulating macrophage cholesterol metabolism. This further suggests that these SAA peptides may modulate cholesterol metabolic pathways in additional tissues/cells.

Example 12

Assessing Efficacy of Peptides by Determination of Prevention of Atherosclerosis The efficacy of SAA2.1 peptides in preventing atherosclerosis was examined. The peptides tested included SEQ ID NO:1 and SEQ ID NO:4 and an equimolar combination of both peptides. Liposomes containing these peptides were injected intravenously into 8-12 week old ApoE knockout mice once every fours days during atherogenic induction for a period of 2-3 weeks (five doses at 6 mg/kg for prevention experiments).

Animals were divided into 5 groups (5 animals per group). The negative control group was placed on a normal chow diet, while the other four groups received an atherogenic diet (Paigen's Atherogenic Rodent diet, as described in Example 11). Among these groups, one group continued on the high fat diet for three weeks. The other groups continued on the high fat diet for the same period but also received either liposomes containing peptide SEQ ID NO: 1, liposomes containing peptide SEQ ID NO:4 or liposomes containing an equimolar combination of both of these peptides (5 doses as described in the preceding paragraph).

To assess the effects of the peptides on aortic atherosclerosis, at the termination of the experiment, the aorta was removed from the animals and opened longitudinally. The endothelial surface was stained with Oil Red O and the area occupied by lipid was measured by image analysis. Furthermore, histological sections of aorta were prepared for microscopic analysis and total lipids were isolated to measure the quantity of cholesterol per weight of tissue. Blood was isolated to measure total plasma cholesterol levels.

Example 13

Cholesterol Efflux in Tissue Culture Mediated by L-Amino Acid and D-Amino Acid Peptides Corresponding to Residues 77-103 of Murine SAA1.1

Macrophages loaded with [$^3$H]cholesterol were pre-incubated in the absence or presence of liposomes containing 0.5 µM cyanogen bromide-released peptides corresponding to amino acid residues 77-103 of murine SAA1.1 (SEQ ID NO:9), synthetic D-amino acid peptides of the corresponding sequence (SEQ ID NO:10), or synthetic peptides corresponding to the native L-amino acid residues 74-103 of murine SAA2.1 (SEQ ID NO:7). Following incubation, the cells were washed extensively with Dulbecco's modified Eagle medium (DMEM) containing 0.2% bovine serum albumin (BSA) to remove all radioactivity and liposomes in the pre-incubation medium. The chase efflux media consisted of DMEM/BSA alone or medium containing HDL (50 µg/mL). See FIG. 2. The results represent cholesterol efflux to the acceptor, HDL, in the medium from cells with various liposome pre-treatments. The efflux media were collected as 1, 2, 4, 8, 16 and 24 hours and analyzed for [$^3$H] cholesterol. Total [$^3$H] cholesterol was $(1.8-2.1) \times 10^6$ dpm/mg cell protein.

Example 14

Cholesterol Efflux in Human Monocytic Cell Line, THP-1

Studies were carried out to determine whether murine SAA2.1 increases cholesterol export from a human derived monocytic cell line, THP-1 (obtained from American Type Culture Collection, Manassas, Va.; ATCC#TIB-202). Human monocytes were cultured in T-75 flasks with 30 ml RPMI 1640 medium containing 2 mM L-glutamine, 4.5 g/L glucose, 10 mM HEPES, 1.0 mM sodium private and supplemented with 0.05 mM 2-mercaptoethanol and 10% fetal bovine serum. Subsequently, five million cells were placed in each well of a 6-well tissue culture plate. The monocytes were differentiated into macrophages by treatment with phorbol myristate acetate (100 nM). THP-1 macrophages were enriched with cholesterol by incubating with red blood cells membrane fragments (175 µg as cholesterol) that had been previously labelled with 0.5 µCi/mL[$^3$H]-cholesterol at 37° C. for 6 hours in 0.2% bovine serum albumin, followed by an overnight equilibration period. Cells were washed four times with PBS/BSA prior to efflux studies. Cells were then incubated at 37° C. with 2 mL RPMI-BSA containing 5% LPDS and 50 µg/mL of either native HDL, SAA-HDL, liposomes containing 2 µmoles of apoA-I, SAA1.1 or 2.1, or liposomes containing 0.5 µmoles synthetic peptides corresponding to amino acid residues 1-20 (SEQ ID NO:1), 21-50 (SEQ ID NO:2), 51-80 (SEQ ID NO:3) or 74-103 (SEQ ID NO:4) of murine SAA2.1. The efflux media were collected at 0, 1, 2, 4, 8, 16 and 24 hours, centrifuged to remove cell debris, and then used to measure the exported counts. The cell layers were then washed twice with ice-cold PBS/BSA and twice with PBS. A portion of the cells was lysed in 0.1N NaOH to estimate both the remaining radioactivity and the cellular protein content. Cellular lipids were extracted from the remaining portion of the cells and analyzed by thin-layer chromatography as described by Mendez et al. (J. Clin. Invest. 1994 94:1698-1705) and Oram et al. (Arterioscler. Thromb. 1991 11:403-414). The radioactivity in appropriate spots was measured to determine total cellular cholesterol counts. Efflux of radioactive label to the medium was calculated as the percentage of total counts (cell+medium counts) in each well.

Example 15

Increase in Cholesterol Efflux in Vivo with D-27mer

J774 cells cultured in 6-well plates were enriched with cholesterol by incubating with red blood cell (RBC) membrane fragments (175 µg as cholesterol) that had been previously labeled with 0.5 µCi/ml [$^3$H]-cholesterol at 37° C. for 24 hours in 0.2% bovine serum albumin (BSA). After loading with the labelled RBC membrane for 6 hours, cells were then washed with phosphate-buffered saline/BSA (PBS/BSA) three times followed by an 18 hour equilibration period during which monolayers were exposed to DMEM/BSA. To determine cholesterol export in vivo, J774 macrophages were cholesterol-loaded with RBC membranes and [$^3$H]-cholesterol as described previously above. Cells were washed four times with PBS/BSA and then detached from the culture dishes. Two hundred thousand cells in 100 µl PBS were injected into mice through the tail vein. At various time points thereafter, approximately 25 μl of blood were collected from the tail vein of each animal into heparinized capillary tubes. These tubes were then centrifuged for 5 minutes in an Adams Autocrit Centrifuge to separate red blood cells from plasma. Cholesterol efflux was determined by measuring the appearance of [$^3$H]-cholesterol in plasma by scintillation spectrometry. To study whether export of cholesterol from J774 cells to plasma is influenced by the D-27mer peptide (ADQEAN-RHGRSGKDPNYYRPPGLPAKY (D-form; SEQ ID NO:10), 24 hours after injection of [$^3$H]-cholesterol-loaded J774 macrophages into mice, the same animals received, by either intravenous injection or gavage, non-liposome formulated D-27 mer peptide. For intravenous injection, various dosages of the D-27mer peptide were used ranging from 0 to 600 μg per mouse. The amounts of D-27mer administered intravenously were 30 μg, 60 μg, 150 μg, 225 μg, 300 μg and 600 μg. All these amounts of D-peptides were dissolved in 100 μl of PBS and injected through the tail vein of each animal. For gavage experiments, the dosage of 600 μg per mouse was used.

The D-27mer peptide was dissolved in 500 μl of PBS prior to oral administration. Oral gavage was carried out using a ball ended feeding needle. Due to the delicacy of mice and the trauma which may be induced by improper gavage techniques, i.e. over or under insertion of the gavage needle, prior to administration of the peptide via gavage, the distance that the needle needed to be inserted into the mouse (usually from the nose to the first rib) was determined and marked on the needle. The mouse was restrained with the head and body extended as straight as possible to facilitate introduction of the gavage needle. The needle was introduced in the space between the left incisors and molars, and gently directed above the tongue into the esophagus. Once the desired position was attained, the D-27mer peptide (600 μg in 0.5 ml) was injected and the needle with syringe was withdrawn from the animal.

At various time points following either intravenous injection or oral gavage, approximately 25 μl of blood were collected from the tail vein of each animal and analyzed as described above.

Example: 16

Statistical Analysis

Unpaired Student's t tests were used to compare group means. A value of $P < 0.05$ was considered statistically significant. Histological sections of aorta were compared by ANOVA.

What is claimed is:

1. An isolated peptide which enhances cholesterol ester hydrolase activity, said isolated peptide comprising a formula:

$$X_1X_2X_3X_4X_5X_6X_7X_8X_9X_{10}X_{11}X_{12}X_{13}X_{14}X_{15}X_{16}X_{17}X_{18}$$ (SEQ ID NO:29)

wherein $X_1$ and $X_9$, $X_{12}$ or $X_{18}$ are amino acids capable of forming a salt bridge;

$X_6$ is lysine or an amino acid which is a conservative substitution thereof;

$X_2$, $X_3$, $X_4$, $X_5$, $X_7$, $X_8$, $X_{10}$, $X_{11}$, $X_{13}$, $X_{14}$, $X_{15}$, $X_{16}$, and $X_{17}$ are independently any amino acid; and one or more amino acids of said formula is a D amino acid;

wherein said isolated peptide exhibits at least 85% sequence identity to DQAANKWGRSGRDPNHFR (SEQ ID NO:26) calculated over the length of SEQ ID NO:26, notwithstanding any additional amino acids of said isolated peptide which may extend beyond the length of SEQ ID NO:26, and wherein the isolated peptide has less than 80 amino acid residues.

2. The isolated peptide of claim 1 wherein $X_2$ is glutamine or an amino acid which is a conservative substitution thereof;

$X_3$ and $X_4$ are independently alanine or an amino acid which is a conservative substitution thereof;

$X_5$ and $X_{15}$ are independently asparagine or an amino acid which is a conservative substitution thereof;

$X_7$ is tryptophan or an amino acid which is a conservative substitution thereof;

$X_8$ and $X_{11}$ are independently glycine or an amino acid which is a conservative substitution thereof;

$X_{10}$ is serine or an amino acid which is a conservative substitution thereof;

$X_{13}$ is aspartic acid or an amino acid which is a conservative substitution thereof;

$X_{14}$ is proline or an amino acid which is a conservative substitution thereof;

$X_{16}$ is histidine or an amino acid which is a conservative substitution thereof; and $X_{17}$ is phenylalanine or an amino acid which is a conservative substitution thereof.

3. The isolated peptide of claim 1 which has 18 to 79 amino acid residues.

4. The isolated peptide of claim 1 which has one or more conservative amino acid substitutions in the amino acid sequence of the peptide comprising:
ADQAANKWGRSGRDPNHFR (SEQ ID NO:11); or
DQAANKWGRSGRDPNHFR (SEQ ID NO:26),
and comprises one or more D amino acids.

5. A pharmaceutical composition comprising the isolated peptide of claim 1 and a pharmaceutically acceptable vehicle.

6. The pharmaceutical composition of claim 5 wherein the pharmaceutical composition is suitable for oral, intravenous, intramuscular or sublingual administration or administration via inhalation.

7. The pharmaceutical composition of claim 6 wherein the pharmaceutical composition is suitable for oral administration and comprises a sugar.

8. The pharmaceutical composition of claim 5 further comprising a second isolated peptide which inhibits acyl CoA:cholesterol acyl transferase activity, said second isolated peptide comprising a peptide with at least 90% sequence identity with
GFFSFVHEAFQGAGDMWRAY (SEQ ID NO:1);
RSFFSFLGEAFDGARDMWRAYSD (SEQ ID NO:6); or
RGFFSFIGEAFQGAGDMWRAY (SEQ ID NO:7).

9. The pharmaceutical composition of claim 8 wherein the isolated peptide which enhances cholesterol ester hydrolase activity comprises:
SEQ ID NO:26 or SEQ ID NO:11.

10. The pharmaceutical composition of claim 5 wherein the isolated peptide which enhances cholesterol ester hydrolase activity comprises
SEQ ID NO:26 or SEQ ID NO:11.

11. A compound having a formula:

Y-Z wherein Y comprises a peptide which enhances cholesterol ester hydrolase activity; said peptide comprising a formula:

$$X_1X_2X_3X_4X_5X_6X_7X_8X_9X_{10}X_{11}X_{12}X_{13}X_{14}X_{15}X_{16}X_{17}X_{18}$$ (SEQ ID NO:29)

wherein $X_1$ and $X_9$, $X_{12}$ or $X_{18}$ are amino acids capable of forming a salt bridge;

$X_6$ is glutamic acid or lysine or an amino acid which is a conservative substitution thereof;

$X_2$, $X_3$, $X_4$, $X_5$, $X_7$, $X_8$, $X_{10}$, $X_{11}$, $X_{13}$, $X_{14}$, $X_{15}$, $X_{16}$, and $X_{17}$ are independently any amino acid; and one or more amino acids of said formula is a D amino acid;

wherein said isolated peptide exhibits at least 85% sequence identity to DQAANKWGRSGRDPNHFR (SEQ ID NO:26) calculated over the length of SEQ ID NO:26, notwithstanding any additional amino acids of said isolated peptide which may extend beyond the length of SEQ ID NO:26; and the isolated peptide has less than 80 amino acid residues, and wherein Z is a component linked to Y and enhances the performance of Y, wherein Z is a liposome, a microsphere, a ligand for serum amyloid A (SAA) receptor or a targeting agent to atherosclerotic plaques.

12. A pharmaceutical composition comprising the compound of claim 11 and a pharmaceutically acceptable vehicle.

13. The pharmaceutical composition of claim 12 wherein the pharmaceutical composition is suitable for oral, intravenous, intramuscular or sublingual administration or administration via inhalation.

14. The pharmaceutical composition of claim 13 wherein the pharmaceutical composition is suitable for oral administration and comprises a sugar.

15. The pharmaceutical composition of claim 12 further comprising an isolated peptide which inhibits acyl CoA:cholesterol acyl transferase activity, said isolated peptide comprising a peptide with at least 90% sequence identity with
GFFSFVHEAFQGAGDMWRAY (SEQ ID NO:1);
RSFFSFLGEAFDGARDMWRAYSD (SEQ ID NO:6); or
RGFFSFIGEAFQGAGDMWRAY (SEQ ID NO:7).

16. An isolated peptide which enhances cholesterol ester hydrolase activity, said isolated peptide comprising
ADQEANRHGRSGKDPNYYRPPGLPAKY (D-form; SEQ ID NO:10),
wherein the isolated peptide has less than 80 amino acid residues.

17. An isolated peptide which enhances cholesterol ester hydrolase activity, said isolated peptide comprising the amino acid sequence of
DTIADQEANRHGRSGKDPNYYRPPGLPDKY (SEQ ID NO:4);

ADQEANRHGRSGKDPNYYRPPGLPDKY (SEQ ID NO:8);
ADQEANRHGRSGKDPNYYRPPGLPAKY (SEQ ID NO:9);
ADQEANRHGRSGKDPNYYR (SEQ ID NO:25);
ADQAANKWGRSGRDPNHFR (SEQ ID NO:11); or
DQAANKWGRSGRDPNHFR (SEQ ID NO:26),
wherein the amino acid sequence of SEQ ID NO: 4, 8, 9, 11, 25 or 26 comprises one or more D amino acids, and wherein the isolated peptide has less than 80 amino acid residues.

18. An isolated peptide consisting of the amino acid sequence of ADQAANEWGRSGKDPNHFR (SEQ ID NO:12) or ADQAANEWGRSGKDPNHFR (D-form; SEQ ID NO:32).

* * * * *

```
                           SEQUENCE LISTING

<160> NUMBER OF SEQ ID NOS: 46

<210> SEQ ID NO 1
<211> LENGTH: 20
<212> TYPE: PRT
<213> ORGANISM: Artificial sequence
<220> FEATURE:
<223> OTHER INFORMATION: Synthetic

<400> SEQUENCE: 1

Gly Phe Phe Ser Phe Val His Glu Ala Phe Gln Gly Ala Gly Asp Met
1               5                   10                  15

Trp Arg Ala Tyr
            20

<210> SEQ ID NO 2
<211> LENGTH: 30
<212> TYPE: PRT
<213> ORGANISM: Artificial sequence
<220> FEATURE:
<223> OTHER INFORMATION: Synthetic

<400> SEQUENCE: 2

Thr Asp Met Lys Glu Ala Asn Trp Lys Asn Ser Asp Lys Tyr Phe His
1               5                   10                  15

Ala Arg Gly Asn Tyr Asp Ala Ala Gln Arg Gly Pro Gly Gly
            20                  25                  30

<210> SEQ ID NO 3
<211> LENGTH: 30
<212> TYPE: PRT
<213> ORGANISM: Artificial sequence
<220> FEATURE:
<223> OTHER INFORMATION: Synthetic

<400> SEQUENCE: 3

Val Trp Ala Ala Glu Lys Ile Ser Asp Gly Arg Glu Ala Phe Gln Glu
```

```
                1               5                  10                  15
Phe Phe Gly Arg Gly His Glu Asp Thr Ile Ala Asp Gln Glu
            20                  25                  30

<210> SEQ ID NO 4
<211> LENGTH: 30
<212> TYPE: PRT
<213> ORGANISM: Artificial sequence
<220> FEATURE:
<223> OTHER INFORMATION: Synthetic

<400> SEQUENCE: 4

Asp Thr Ile Ala Asp Gln Glu Ala Asn Arg His Gly Arg Ser Gly Lys
1               5                  10                  15

Asp Pro Asn Tyr Tyr Arg Pro Pro Gly Leu Pro Asp Lys Tyr
            20                  25                  30

<210> SEQ ID NO 5
<211> LENGTH: 20
<212> TYPE: PRT
<213> ORGANISM: Artificial sequence
<220> FEATURE:
<223> OTHER INFORMATION: Synthetic

<400> SEQUENCE: 5

Gly Phe Phe Ser Phe Ile Gly Glu Ala Phe Gln Gly Ala Gly Asp Met
1               5                  10                  15

Trp Arg Ala Tyr
            20

<210> SEQ ID NO 6
<211> LENGTH: 23
<212> TYPE: PRT
<213> ORGANISM: Artificial sequence
<220> FEATURE:
<223> OTHER INFORMATION: Synthetic

<400> SEQUENCE: 6

Arg Ser Phe Phe Ser Phe Leu Gly Glu Ala Phe Asp Gly Ala Arg Asp
1               5                  10                  15

Met Trp Arg Ala Tyr Ser Asp
            20

<210> SEQ ID NO 7
<211> LENGTH: 21
<212> TYPE: PRT
<213> ORGANISM: Artificial sequence
<220> FEATURE:
<223> OTHER INFORMATION: Synthetic

<400> SEQUENCE: 7

Arg Gly Phe Phe Ser Phe Ile Gly Glu Ala Phe Gln Gly Ala Gly Asp
1               5                  10                  15

Met Trp Arg Ala Tyr
            20

<210> SEQ ID NO 8
<211> LENGTH: 27
<212> TYPE: PRT
<213> ORGANISM: Artificial sequence
<220> FEATURE:
<223> OTHER INFORMATION: Synthetic

<400> SEQUENCE: 8
```

Ala Asp Gln Glu Ala Asn Arg His Gly Arg Ser Gly Lys Asp Pro Asn
1               5                   10                  15

Tyr Tyr Arg Pro Pro Gly Leu Pro Asp Lys Tyr
            20                  25

<210> SEQ ID NO 9
<211> LENGTH: 27
<212> TYPE: PRT
<213> ORGANISM: Artificial sequence
<220> FEATURE:
<223> OTHER INFORMATION: Synthetic

<400> SEQUENCE: 9

Ala Asp Gln Glu Ala Asn Arg His Gly Arg Ser Gly Lys Asp Pro Asn
1               5                   10                  15

Tyr Tyr Arg Pro Pro Gly Leu Pro Ala Lys Tyr
            20                  25

<210> SEQ ID NO 10
<211> LENGTH: 27
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(27)
<223> OTHER INFORMATION: D amino acid

<400> SEQUENCE: 10

Ala Asp Gln Glu Ala Asn Arg His Gly Arg Ser Gly Lys Asp Pro Asn
1               5                   10                  15

Tyr Tyr Arg Pro Pro Gly Leu Pro Ala Lys Tyr
            20                  25

<210> SEQ ID NO 11
<211> LENGTH: 19
<212> TYPE: PRT
<213> ORGANISM: Artificial sequence
<220> FEATURE:
<223> OTHER INFORMATION: Synthetic

<400> SEQUENCE: 11

Ala Asp Gln Ala Ala Asn Lys Trp Gly Arg Ser Gly Arg Asp Pro Asn
1               5                   10                  15

His Phe Arg

<210> SEQ ID NO 12
<211> LENGTH: 19
<212> TYPE: PRT
<213> ORGANISM: Artificial sequence
<220> FEATURE:
<223> OTHER INFORMATION: Synthetic

<400> SEQUENCE: 12

Ala Asp Gln Ala Ala Asn Glu Trp Gly Arg Ser Gly Lys Asp Pro Asn
1               5                   10                  15

His Phe Arg

<210> SEQ ID NO 13
<211> LENGTH: 11
<212> TYPE: PRT
<213> ORGANISM: Artificial sequence
<220> FEATURE:
<223> OTHER INFORMATION: Synthetic

```
<220> FEATURE:
<221> NAME/KEY: MISC_FEATURE
<222> LOCATION: (1)..(1)
<223> OTHER INFORMATION: X=any amino acid
<220> FEATURE:
<221> NAME/KEY: MISC_FEATURE
<222> LOCATION: (4)..(4)
<223> OTHER INFORMATION: X=any amino acid
<220> FEATURE:
<221> NAME/KEY: MISC_FEATURE
<222> LOCATION: (6)..(6)
<223> OTHER INFORMATION: X=hydrophobic or nonpolar amino acid
<220> FEATURE:
<221> NAME/KEY: MISC_FEATURE
<222> LOCATION: (7)..(7)
<223> OTHER INFORMATION: X=histidine or conservative substitution
      thereof
<220> FEATURE:
<221> NAME/KEY: MISC_FEATURE
<222> LOCATION: (8)..(8)
<223> OTHER INFORMATION: X=any amino acid
<220> FEATURE:
<221> NAME/KEY: MISC_FEATURE
<222> LOCATION: (9)..(9)
<223> OTHER INFORMATION: X=any amino acid
<220> FEATURE:
<221> NAME/KEY: MISC_FEATURE
<222> LOCATION: (11)..(11)
<223> OTHER INFORMATION: X=any amino acid

<400> SEQUENCE: 13

Xaa Phe Phe Xaa Phe Xaa Xaa Xaa Xaa Phe Xaa
1               5                   10

<210> SEQ ID NO 14
<211> LENGTH: 12
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X=amino acid capable of forming salt bridge
<220> FEATURE:
<221> NAME/KEY: MISC_FEATURE
<222> LOCATION: (2)..(2)
<223> OTHER INFORMATION: X=any amino acid
<220> FEATURE:
<221> NAME/KEY: MISC_FEATURE
<222> LOCATION: (5)..(5)
<223> OTHER INFORMATION: X=any amino acid
<220> FEATURE:
<221> NAME/KEY: MISC_FEATURE
<222> LOCATION: (7)..(10)
<223> OTHER INFORMATION: X=any amino acid
<220> FEATURE:
<221> NAME/KEY: MISC_FEATURE
<222> LOCATION: (12)..(12)
<223> OTHER INFORMATION: X=amino acid capable of forming salt bridge

<400> SEQUENCE: 14

Xaa Xaa Phe Phe Xaa Phe Xaa Xaa Xaa Xaa Phe Xaa
1               5                   10

<210> SEQ ID NO 15
<211> LENGTH: 16
<212> TYPE: PRT
<213> ORGANISM: Artificial sequence
<220> FEATURE:
<223> OTHER INFORMATION: Synthetic

<400> SEQUENCE: 15

Gly Phe Phe Ser Phe Val His Glu Ala Phe Gln Gly Ala Gly Asp Met
```

<210> SEQ ID NO 16
<211> LENGTH: 16
<212> TYPE: PRT
<213> ORGANISM: Artificial sequence
<220> FEATURE:
<223> OTHER INFORMATION: Synthetic

<400> SEQUENCE: 16

Gly Phe Phe Ser Phe Ile Gly Glu Ala Phe Gln Gly Ala Gly Asp Met
1               5                   10                  15

<210> SEQ ID NO 17
<211> LENGTH: 18
<212> TYPE: PRT
<213> ORGANISM: Artificial sequence
<220> FEATURE:
<223> OTHER INFORMATION: Synthetic

<400> SEQUENCE: 17

Arg Ser Phe Phe Ser Phe Leu Gly Glu Ala Phe Asp Gly Ala Arg Asp
1               5                   10                  15

Met Trp

<210> SEQ ID NO 18
<211> LENGTH: 103
<212> TYPE: PRT
<213> ORGANISM: Mus musculis

<400> SEQUENCE: 18

Gly Phe Phe Ser Phe Ile Gly Glu Ala Phe Gln Gly Ala Gly Asp Met
1               5                   10                  15

Trp Arg Ala Tyr Thr Asp Met Lys Glu Ala Gly Trp Lys Asp Gly Asp
                20                  25                  30

Lys Tyr Phe His Ala Arg Gly Asn Tyr Asp Ala Ala Gln Arg Gly Pro
            35                  40                  45

Gly Gly Val Trp Ala Ala Glu Lys Ile Ser Asp Ala Arg Glu Ser Phe
        50                  55                  60

Gln Glu Phe Phe Gly Arg Gly His Glu Asp Thr Met Ala Asp Gln Glu
65                  70                  75                  80

Ala Asn Arg His Gly Arg Ser Gly Lys Asp Pro Asn Tyr Tyr Arg Pro
                85                  90                  95

Pro Gly Leu Pro Ala Lys Tyr
            100

<210> SEQ ID NO 19
<211> LENGTH: 103
<212> TYPE: PRT
<213> ORGANISM: Mus musculis

<400> SEQUENCE: 19

Gly Phe Phe Ser Phe Val His Glu Ala Phe Gln Gly Ala Gly Asp Met
1               5                   10                  15

Trp Arg Ala Tyr Thr Asp Met Lys Glu Ala Asn Trp Lys Asn Ser Asp
                20                  25                  30

Lys Tyr Phe His Ala Arg Gly Asn Tyr Asp Ala Ala Gln Arg Gly Pro
            35                  40                  45

Gly Gly Val Trp Ala Ala Glu Lys Ile Ser Asp Gly Arg Glu Ala Phe
        50                  55                  60

```
Gln Glu Phe Phe Gly Arg Gly His Glu Asp Thr Ile Ala Asp Gln Glu
65                  70                  75                  80

Ala Asn Arg His Gly Arg Ser Gly Lys Asp Pro Asn Tyr Tyr Arg Pro
                85                  90                  95

Pro Gly Leu Pro Asp Lys Tyr
            100

<210> SEQ ID NO 20
<211> LENGTH: 104
<212> TYPE: PRT
<213> ORGANISM: Homo sapien

<400> SEQUENCE: 20

Arg Ser Phe Phe Ser Phe Leu Gly Glu Ala Phe Asp Gly Ala Arg Asp
1               5                   10                  15

Met Trp Arg Ala Tyr Ser Asp Met Arg Glu Ala Asn Tyr Ile Gly Ser
                20                  25                  30

Asp Lys Tyr Phe His Ala Arg Gly Asn Tyr Asp Ala Ala Lys Arg Gly
                35                  40                  45

Pro Gly Gly Val Trp Ala Ala Glu Ala Ile Ser Asp Ala Arg Glu Asn
            50                  55                  60

Ile Gln Arg Phe Phe Gly His Gly Ala Glu Asp Ser Leu Ala Asp Gln
65                  70                  75                  80

Ala Ala Asn Glu Trp Gly Arg Ser Gly Lys Asp Pro Asn His Phe Arg
                85                  90                  95

Pro Ala Gly Leu Pro Glu Lys Tyr
            100

<210> SEQ ID NO 21
<211> LENGTH: 104
<212> TYPE: PRT
<213> ORGANISM: Homo sapien

<400> SEQUENCE: 21

Arg Ser Phe Phe Ser Phe Leu Gly Glu Ala Phe Asp Gly Ala Arg Asp
1               5                   10                  15

Met Trp Arg Ala Tyr Ser Asp Met Arg Glu Ala Asn Tyr Ile Gly Ser
                20                  25                  30

Asp Lys Tyr Phe His Ala Arg Gly Asn Tyr Asp Ala Ala Lys Arg Gly
                35                  40                  45

Pro Gly Gly Ala Trp Ala Ala Glu Val Ile Ser Asn Ala Arg Glu Asn
            50                  55                  60

Ile Gln Arg Leu Thr Gly His Gly Ala Glu Asp Ser Leu Ala Asp Gln
65                  70                  75                  80

Ala Ala Asn Lys Trp Gly Arg Ser Gly Arg Asp Pro Asn His Phe Arg
                85                  90                  95

Pro Ala Gly Leu Pro Glu Lys Tyr
            100

<210> SEQ ID NO 22
<211> LENGTH: 80
<212> TYPE: PRT
<213> ORGANISM: Artificial sequence
<220> FEATURE:
<223> OTHER INFORMATION: Synthetic

<400> SEQUENCE: 22

Lys Glu Ala Gly Trp Lys Asp Gly Asp Lys Tyr Phe His Ala Arg Gly
1               5                   10                  15
```

Asn Tyr Asp Ala Ala Gln Arg Gly Pro Gly Gly Val Trp Ala Ala Glu
            20                  25                  30

Lys Ile Ser Asp Ala Arg Glu Ser Phe Gln Glu Phe Gly Arg Gly
        35                  40                  45

His Glu Asp Thr Met Ala Asp Gln Glu Ala Asn Arg His Gly Arg Ser
    50                  55                  60

Gly Lys Asp Pro Asn Tyr Tyr Arg Pro Gly Leu Pro Ala Lys Tyr
65                  70                  75                  80

<210> SEQ ID NO 23
<211> LENGTH: 80
<212> TYPE: PRT
<213> ORGANISM: Artificial sequence
<220> FEATURE:
<223> OTHER INFORMATION: Synthetic

<400> SEQUENCE: 23

Lys Glu Ala Asn Trp Lys Asn Ser Asp Lys Tyr Phe His Ala Arg Gly
1               5                   10                  15

Asn Tyr Asp Ala Ala Gln Arg Gly Pro Gly Gly Val Trp Ala Ala Glu
            20                  25                  30

Lys Ile Ser Asp Gly Arg Glu Ala Phe Gln Glu Phe Gly Arg Gly
        35                  40                  45

His Glu Asp Thr Ile Ala Asp Gln Glu Ala Asn Arg His Gly Arg Ser
    50                  55                  60

Gly Lys Asp Pro Asn Tyr Tyr Arg Pro Gly Leu Pro Asp Lys Tyr
65                  70                  75                  80

<210> SEQ ID NO 24
<211> LENGTH: 27
<212> TYPE: PRT
<213> ORGANISM: Artificial sequence
<220> FEATURE:
<223> OTHER INFORMATION: Synthetic

<400> SEQUENCE: 24

Ala Asp Gln Ala Ala Asn Glu Trp Gly Arg Ser Gly Lys Asp Pro Asn
1               5                   10                  15

His Phe Arg Pro Ala Gly Leu Pro Glu Lys Tyr
            20                  25

<210> SEQ ID NO 25
<211> LENGTH: 19
<212> TYPE: PRT
<213> ORGANISM: Artificial sequence
<220> FEATURE:
<223> OTHER INFORMATION: Synthetic

<400> SEQUENCE: 25

Ala Asp Gln Glu Ala Asn Arg His Gly Arg Ser Gly Lys Asp Pro Asn
1               5                   10                  15

Tyr Tyr Arg

<210> SEQ ID NO 26
<211> LENGTH: 18
<212> TYPE: PRT
<213> ORGANISM: Artificial sequence
<220> FEATURE:
<223> OTHER INFORMATION: Synthetic

<400> SEQUENCE: 26

```
Asp Gln Ala Ala Asn Lys Trp Gly Arg Ser Gly Arg Asp Pro Asn His
1               5                   10                  15

Phe Arg

<210> SEQ ID NO 27
<211> LENGTH: 17
<212> TYPE: PRT
<213> ORGANISM: Artificial sequence
<220> FEATURE:
<223> OTHER INFORMATION: Synthetic

<400> SEQUENCE: 27

Gln Ala Ala Asn Lys Trp Gly Arg Ser Gly Arg Asp Pro Asn His Phe
1               5                   10                  15

Arg

<210> SEQ ID NO 28
<211> LENGTH: 16
<212> TYPE: PRT
<213> ORGANISM: Artificial sequence
<220> FEATURE:
<223> OTHER INFORMATION: Synthetic

<400> SEQUENCE: 28

Ala Ala Asn Lys Trp Gly Arg Ser Gly Arg Asp Pro Asn His Phe Arg
1               5                   10                  15

<210> SEQ ID NO 29
<211> LENGTH: 18
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: X=amino acid capable of forming salt bridge
<220> FEATURE:
<221> NAME/KEY: MISC_FEATURE
<222> LOCATION: (2)..(5)
<223> OTHER INFORMATION: X=any amino acid
<220> FEATURE:
<221> NAME/KEY: MISC_FEATURE
<222> LOCATION: (6)..(6)
<223> OTHER INFORMATION: X=glutamic acid or lysine or conservative
      substitution thereof
<220> FEATURE:
<221> NAME/KEY: MISC_FEATURE
<222> LOCATION: (7)..(8)
<223> OTHER INFORMATION: X=any amino acid
<220> FEATURE:
<221> NAME/KEY: MISC_FEATURE
<222> LOCATION: (9)..(9)
<223> OTHER INFORMATION: X=amino acid capable of forming salt bridge
<220> FEATURE:
<221> NAME/KEY: MISC_FEATURE
<222> LOCATION: (10)..(11)
<223> OTHER INFORMATION: X=any amino acid
<220> FEATURE:
<221> NAME/KEY: MISC_FEATURE
<222> LOCATION: (12)..(12)
<223> OTHER INFORMATION: X=amino acid capable of forming salt bridge
<220> FEATURE:
<221> NAME/KEY: MISC_FEATURE
<222> LOCATION: (13)..(17)
<223> OTHER INFORMATION: X=any amino acid
<220> FEATURE:
<221> NAME/KEY: MISC_FEATURE
<222> LOCATION: (18)..(18)
<223> OTHER INFORMATION: X=amino acid capable of forming salt bridge

<400> SEQUENCE: 29
```

```
Xaa Xaa Xaa Xaa Xaa Xaa Xaa Xaa Xaa Xaa Xaa Xaa Xaa Xaa Xaa
1               5                   10                  15

Xaa Xaa

<210> SEQ ID NO 30
<211> LENGTH: 20
<212> TYPE: PRT
<213> ORGANISM: Artificial sequence
<220> FEATURE:
<223> OTHER INFORMATION: Synthetic

<400> SEQUENCE: 30

Arg Ser Phe Phe Ser Phe Leu Gly Glu Ala Phe Asp Gly Ala Arg Asp
1               5                   10                  15

Met Trp Arg Ala
            20

<210> SEQ ID NO 31
<211> LENGTH: 27
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(27)
<223> OTHER INFORMATION: D amino acid

<400> SEQUENCE: 31

Ala Asp Gln Ala Ala Asn Glu Trp Gly Arg Ser Gly Lys Asp Pro Asn
1               5                   10                  15

His Phe Arg Pro Ala Gly Leu Pro Glu Lys Tyr
            20                  25

<210> SEQ ID NO 32
<211> LENGTH: 19
<212> TYPE: PRT
<213> ORGANISM: Artificial sequence
<220> FEATURE:
<223> OTHER INFORMATION: Synthetic
<220> FEATURE:
<221> NAME/KEY: MISC_FEATURE
<222> LOCATION: (1)..(19)
<223> OTHER INFORMATION: D amino acid

<400> SEQUENCE: 32

Ala Asp Gln Ala Ala Asn Glu Trp Gly Arg Ser Gly Lys Asp Pro Asn
1               5                   10                  15

His Phe Arg

<210> SEQ ID NO 33
<211> LENGTH: 103
<212> TYPE: PRT
<213> ORGANISM: Mus musculis

<400> SEQUENCE: 33

Gly Phe Phe Ser Phe Ile Gly Glu Ala Phe Gln Gly Ala Gly Asp Met
1               5                   10                  15

Trp Arg Ala Tyr Thr Asp Met Lys Glu Ala Gly Trp Lys Asp Gly Asp
            20                  25                  30

Lys Tyr Phe His Ala Arg Gly Asn Tyr Asp Ala Ala Gln Arg Gly Pro
        35                  40                  45

Gly Gly Val Trp Ala Ala Glu Lys Ile Ser Asp Ala Arg Glu Ser Phe
```

-continued

```
                50                  55                  60
Gln Glu Phe Phe Gly Arg Gly His Glu Asp Thr Met Ala Asp Gln Glu
 65                  70                  75                  80

Ala Asn Arg His Gly Arg Ser Gly Lys Asp Pro Asn Tyr Tyr Arg Pro
                 85                  90                  95

Pro Gly Leu Pro Asp Lys Tyr
            100

<210> SEQ ID NO 34
<211> LENGTH: 103
<212> TYPE: PRT
<213> ORGANISM: Mus musculis

<400> SEQUENCE: 34

Gly Phe Phe Ser Phe Ile Ser Glu Ala Phe Gln Gly Ala Gly Asp Met
 1               5                  10                  15

Trp Arg Ala Tyr Thr Asp Met Arg Glu Ala Gly Trp Lys Asp Gly Asp
                 20                  25                  30

Arg Tyr Phe His Ala Arg Gly Asn Tyr Asp Ala Ala Gln Arg Gly Pro
             35                  40                  45

Gly Gly Val Trp Ala Ala Glu Lys Ile Ser Asp Ala Arg Glu Ser Phe
         50                  55                  60

Gln Glu Phe Phe Gly Arg Gly His Glu Asp Thr Met Ala Asp Gln Glu
 65                  70                  75                  80

Ala Asn Arg His Gly Arg Ser Gly Lys Asp Pro Asn Tyr Tyr Arg Pro
                 85                  90                  95

Pro Gly Leu Pro Ala Lys Tyr
            100

<210> SEQ ID NO 35
<211> LENGTH: 103
<212> TYPE: PRT
<213> ORGANISM: Mus musculis

<400> SEQUENCE: 35

Gly Phe Phe Ser Phe Ile Ser Glu Ala Phe Gln Gly Ala Gly Asp Met
 1               5                  10                  15

Trp Arg Ala Tyr Thr Asp Met Lys Glu Ala Gly Trp Lys Asp Gly Asp
                 20                  25                  30

Lys Tyr Phe His Ala Arg Gly Asn Tyr Asp Ala Ala Gln Arg Gly Pro
             35                  40                  45

Gly Gly Val Trp Ala Ala Glu Lys Ile Ser Asp Ala Arg Glu Gly Phe
         50                  55                  60

Gln Glu Phe Phe Gly Arg Gly His Glu Asp Thr Met Ala Asp Gln Glu
 65                  70                  75                  80

Ala Asn Arg His Gly Arg Ser Gly Lys Asp Pro Asn Tyr Tyr Arg Pro
                 85                  90                  95

Pro Gly Leu Pro Ala Lys Tyr
            100

<210> SEQ ID NO 36
<211> LENGTH: 103
<212> TYPE: PRT
<213> ORGANISM: Mus musculis

<400> SEQUENCE: 36

Gly Phe Phe Ser Phe Val His Glu Ala Phe Gln Gly Ala Gly Asp Met
 1               5                  10                  15
```

```
Trp Arg Ala Tyr Thr Asp Met Lys Glu Ala Gly Trp Lys Asp Gly Asp
            20                  25                  30

Lys Tyr Phe His Ala Arg Gly Asn Tyr Asp Ala Ala Gln Arg Gly Pro
        35                  40                  45

Gly Gly Val Trp Ala Ala Glu Lys Ile Ser Asp Ala Arg Glu Ser Phe
    50                  55                  60

Gln Glu Phe Phe Gly Arg Gly His Glu Asp Thr Met Ala Asp Gln Glu
65                  70                  75                  80

Ala Asn Arg His Gly Arg Ser Gly Lys Asp Pro Asn Tyr Tyr Arg Pro
                85                  90                  95

Pro Gly Leu Pro Ala Lys Tyr
            100
```

```
<210> SEQ ID NO 37
<211> LENGTH: 103
<212> TYPE: PRT
<213> ORGANISM: Mus musculis

<400> SEQUENCE: 37

Gly Phe Phe Ser Phe Ile Gly Glu Ala Phe Gln Gly Ala Gly Asp Met
1               5                   10                  15

Trp Arg Ala Tyr Thr Asp Met Lys Glu Ala Gly Trp Lys Asp Gly Asp
            20                  25                  30

Lys Tyr Phe His Ala Arg Gly Asn Tyr Asp Ala Ala Gln Arg Gly Pro
        35                  40                  45

Gly Gly Val Trp Ala Ala Glu Lys Ile Ser Asp Ala Arg Glu Ser Phe
    50                  55                  60

Gln Glu Phe Phe Gly Arg Gly His Glu Asp Thr Met Ala Asp Gln Glu
65                  70                  75                  80

Ala Asn Arg His Gly Arg Ser Gly Lys Asp Pro Asn Tyr Tyr Arg Pro
                85                  90                  95

Pro Gly Leu Pro Asp Lys Tyr
            100
```

```
<210> SEQ ID NO 38
<211> LENGTH: 103
<212> TYPE: PRT
<213> ORGANISM: Mus musculis

<400> SEQUENCE: 38

Gly Phe Phe Ser Phe Val His Glu Ala Phe Leu Gly Ala Gly Asp Met
1               5                   10                  15

Trp Arg Ala Tyr Thr Asp Met Lys Glu Ala Gly Trp Lys Asp Gly Asp
            20                  25                  30

Lys Tyr Phe His Ala Arg Gly Asn Tyr Asp Ala Ala Gln Arg Gly Pro
        35                  40                  45

Gly Gly Val Trp Ala Ala Glu Lys Ile Ser Asp Ala Arg Glu Ala Phe
    50                  55                  60

Gln Glu Phe Phe Gly Arg Gly His Glu Asp Thr Met Ala Asp Gln Glu
65                  70                  75                  80

Ala Asn Arg His Gly Arg Ser Gly Lys Asp Pro Asn Tyr Tyr Arg Pro
                85                  90                  95

Pro Gly Leu Pro Asp Lys Tyr
            100
```

```
<210> SEQ ID NO 39
```

```
<211> LENGTH: 104
<212> TYPE: PRT
<213> ORGANISM: Mus musculis

<400> SEQUENCE: 39

Gln Arg Trp Val Gln Phe Met Lys Glu Ala Gly Gln Gly Ser Arg Asp
1               5                   10                  15

Met Trp Arg Ala Tyr Ser Asp Met Lys Lys Ala Gly Trp Lys Asp Ser
            20                  25                  30

Asp Lys Tyr Phe His Ala Arg Gly Asn Tyr Asp Ala Ala Arg Arg Gly
        35                  40                  45

Pro Gly Gly Ala Trp Ala Ala Lys Val Ile Ser Asp Ala Arg Glu Ser
    50                  55                  60

Val Gln Lys Phe Thr Gly His Gly Ala Glu Asp Ser Arg Ala Asp Gln
65                  70                  75                  80

Phe Ala Asn Glu Trp Gly Arg Ser Gly Lys Asp Pro Asn His Phe Arg
                85                  90                  95

Pro Ala Gly Leu Lys Arg Lys Tyr
            100

<210> SEQ ID NO 40
<211> LENGTH: 111
<212> TYPE: PRT
<213> ORGANISM: Mus musculis

<400> SEQUENCE: 40

Asp Phe Trp Tyr Phe Phe Arg Glu Ala Phe Gln Gly Thr Trp Asp Leu
1               5                   10                  15

Trp Arg Ala Tyr Arg Asp Asn Leu Glu Ala Asn Tyr Gln Asn Ala Asp
            20                  25                  30

Gln Tyr Phe Tyr Ala Arg Gly Asn Tyr Glu Ala Gln Arg Gly Ser
        35                  40                  45

Gly Gly Ile Trp Ala Ala Lys Ile Ile Ser Thr Ser Arg Lys Tyr Phe
    50                  55                  60

Gln Gly Leu Leu Asn Arg Tyr Tyr Phe Gly Ile Arg Asn His Gly Leu
65                  70                  75                  80

Glu Thr Leu Gln Ala Thr Gln Lys Ala Glu Glu Trp Gly Arg Ser Gly
                85                  90                  95

Lys Asn Pro Asn His Phe Arg Pro Glu Gly Leu Glu Ala Phe Tyr
            100                 105                 110

<210> SEQ ID NO 41
<211> LENGTH: 104
<212> TYPE: PRT
<213> ORGANISM: Homo sapien

<400> SEQUENCE: 41

Arg Ser Phe Phe Ser Phe Leu Gly Glu Ala Phe Asp Gly Ala Arg Asp
1               5                   10                  15

Met Trp Arg Ala Tyr Ser Asp Met Arg Glu Ala Asn Tyr Ile Gly Ser
            20                  25                  30

Asp Lys Tyr Phe His Ala Arg Gly Asn Tyr Asp Ala Ala Lys Arg Gly
        35                  40                  45

Pro Gly Gly Ala Trp Ala Ala Glu Val Ile Ser Asp Ala Arg Glu Asn
    50                  55                  60

Ile Gln Arg Phe Phe Gly His Asp Ala Glu Asp Ser Leu Ala Asp Gln
65                  70                  75                  80
```

```
Ala Ala Asn Glu Trp Gly Arg Ser Gly Lys Asp Pro Asn His Phe Arg
            85                  90                  95

Pro Ala Gly Leu Pro Glu Lys Tyr
            100

<210> SEQ ID NO 42
<211> LENGTH: 104
<212> TYPE: PRT
<213> ORGANISM: Homo sapien

<400> SEQUENCE: 42

Arg Ser Phe Phe Ser Phe Leu Gly Glu Ala Phe Asp Gly Ala Arg Asp
1               5                   10                  15

Met Trp Arg Ala Tyr Ser Asp Met Arg Glu Ala Asn Tyr Ile Gly Ser
            20                  25                  30

Asp Lys Tyr Phe His Ala Arg Gly Asn Tyr Asp Ala Ala Lys Arg Gly
        35                  40                  45

Pro Gly Gly Ala Trp Ala Ala Glu Ala Ile Ser Asp Ala Arg Glu Asn
    50                  55                  60

Ile Gln Arg Phe Gly His Gly Ala Glu Asp Ser Leu Ala Asp Gln
65                  70                  75                  80

Ala Ala Asn Glu Trp Gly Arg Ser Gly Lys Asp Pro Asn His Phe Arg
            85                  90                  95

Pro Ala Gly Leu Pro Glu Lys Tyr
            100

<210> SEQ ID NO 43
<211> LENGTH: 104
<212> TYPE: PRT
<213> ORGANISM: Homo sapien

<400> SEQUENCE: 43

Arg Ser Phe Phe Ser Phe Leu Gly Glu Ala Phe Asp Gly Ala Arg Asp
1               5                   10                  15

Met Trp Arg Ala Tyr Ser Asp Met Arg Glu Ala Asn Tyr Ile Gly Ser
            20                  25                  30

Asp Lys Tyr Phe His Ala Arg Gly Asn Tyr Asp Ala Ala Lys Arg Gly
        35                  40                  45

Pro Gly Gly Ala Trp Ala Ala Glu Val Ile Ser Asn Ala Arg Glu Asn
    50                  55                  60

Ile Gln Arg Phe Gly His Gly Ala Glu Asp Ser Leu Ala Asp Gln
65                  70                  75                  80

Ala Ala Asn Glu Trp Gly Arg Ser Gly Lys Asp Pro Asn His Phe Arg
            85                  90                  95

Pro Ala Gly Leu Pro Glu Lys Tyr
            100

<210> SEQ ID NO 44
<211> LENGTH: 104
<212> TYPE: PRT
<213> ORGANISM: Homo sapien

<400> SEQUENCE: 44

Arg Ser Phe Phe Ser Phe Leu Gly Glu Ala Phe Asp Gly Ala Arg Asp
1               5                   10                  15

Met Trp Arg Ala Tyr Ser Asp Met Arg Glu Ala Asn Tyr Ile Gly Ser
            20                  25                  30

Asp Lys Tyr Phe His Ala Arg Gly Asn Tyr Asp Ala Ala Lys Arg Gly
```

```
                35                  40                  45

Pro Gly Gly Ala Trp Ala Ala Glu Val Ile Ser Asp Ala Arg Glu Asn
        50                  55                  60

Ile Gln Arg Phe Phe Gly His Gly Ala Glu Asp Ser Leu Ala Asp Gln
65                  70                  75                  80

Ala Ala Asn Glu Trp Gly Arg Ser Gly Lys Asp Pro Asn His Phe Arg
                85                  90                  95

Pro Ala Gly Leu Pro Glu Lys Tyr
            100

<210> SEQ ID NO 45
<211> LENGTH: 104
<212> TYPE: PRT
<213> ORGANISM: Homo sapien

<400> SEQUENCE: 45

Arg Ser Phe Phe Ser Phe Leu Gly Glu Ala Phe Asp Gly Ala Arg Asp
1               5                   10                  15

Met Trp Arg Ala Tyr Ser Asp Met Arg Glu Ala Asn Tyr Ile Gly Ser
                20                  25                  30

Asp Lys Tyr Phe His Ala Arg Gly Asn Tyr Asp Ala Ala Lys Arg Gly
                35                  40                  45

Pro Gly Gly Ala Trp Ala Ala Glu Val Ile Ser Asn Ala Arg Glu Asn
        50                  55                  60

Ile Gln Arg Leu Thr Gly Arg Gly Ala Glu Asp Ser Leu Ala Asp Gln
65                  70                  75                  80

Ala Ala Asn Lys Trp Gly Arg Ser Gly Arg Asp Pro Asn His Phe Arg
                85                  90                  95

Pro Ala Gly Leu Pro Glu Lys Tyr
            100

<210> SEQ ID NO 46
<211> LENGTH: 112
<212> TYPE: PRT
<213> ORGANISM: Homo sapien

<400> SEQUENCE: 46

Glu Ser Trp Arg Ser Phe Phe Lys Glu Ala Leu Gln Gly Val Gly Asp
1               5                   10                  15

Met Gly Arg Ala Tyr Met Asp Ile Met Ile Ser Met His Gln Asn Ser
                20                  25                  30

Asn Arg Tyr Leu Tyr Ala Arg Gly Asn Tyr Asp Ala Ala Gln Arg Gly
                35                  40                  45

Pro Gly Gly Val Trp Ala Ala Lys Leu Ile Ser Arg Ser Arg Val Tyr
        50                  55                  60

Leu Gln Gly Leu Asp Tyr Tyr Leu Phe Gly Asn Ser Ile Ser Thr Val
65                  70                  75                  80

Leu Glu Asp Ser Lys Ser Asn Glu Lys Ala Glu Glu Trp Gly Arg Ser
                85                  90                  95

Gly Lys Asp Pro Asp Arg Phe Arg Pro Asp Gly Leu Pro Lys Lys Tyr
            100                 105                 110
```